US009023351B2

(12) United States Patent
Kahnert et al.

(10) Patent No.: US 9,023,351 B2
(45) Date of Patent: May 5, 2015

(54) ANTI-MESOTHELIN ANTIBODIES AND USES THEREOF

(75) Inventors: Antje Kahnert, Wuppertal (DE); David Light, San Mateo, CA (US); Doug Schneider, Lafayette, CA (US); Renate Parry, Oakland, CA (US); Noboru Satozawa, Chiba (JP); Tara Renee Heitner Hansen, København (DK); Stefan Steidl, München (DE); Ulrike Schubert, München (DE)

(73) Assignee: Bayer Intellectual Property GmbH, Monheim (DE)

( * ) Notice: Subject to any disclaimer, the term of this patent is extended or adjusted under 35 U.S.C. 154(b) by 918 days.

(21) Appl. No.: 12/744,849

(22) PCT Filed: Nov. 19, 2008

(86) PCT No.: PCT/EP2008/009756
§ 371 (c)(1),
(2), (4) Date: Oct. 20, 2010

(87) PCT Pub. No.: WO2009/068204
PCT Pub. Date: Jun. 4, 2009

(65) Prior Publication Data
US 2011/0027268 A1    Feb. 3, 2011

Related U.S. Application Data

(60) Provisional application No. 61/004,378, filed on Nov. 26, 2007.

(51) Int. Cl.
*C12P 21/08* (2006.01)
*C07K 16/30* (2006.01)

(52) U.S. Cl.
CPC .............. *C07K 16/30* (2013.01); *C07K 2317/21* (2013.01); *C07K 2317/56* (2013.01); *C07K 2317/92* (2013.01)
USPC ...................................................... 424/133.1

(58) Field of Classification Search
None
See application file for complete search history.

(56) References Cited

U.S. PATENT DOCUMENTS

| 6,809,184 B1 | 10/2004 | Pastan et al. | |
| 2006/0204506 A1* | 9/2006 | Ebel et al. | 424/155.1 |

FOREIGN PATENT DOCUMENTS

| WO | 9429451 A2 | 12/1994 |
| WO | 9708320 A1 | 3/1997 |
| WO | 97/25068 A2 | 7/1997 |
| WO | 99/28471 A2 | 6/1999 |
| WO | 2006/099141 A2 | 9/2006 |
| WO | 2006124641 A2 | 11/2006 |
| WO | 2006130458 A2 | 12/2006 |

OTHER PUBLICATIONS

Mariuzza et al. (Annu. Rev. Biophys. Biophys. Chem. 1987; 16: 139-159).*
Gussow et al. (Methods in Enzymology. 1991; 203: 99-121).*
MacCallum et al. (J. Mol. Biol. Oct. 11, 1996; 262 (5): 732-745).*
Rudikoff et al (Proc. Natl. Acad. Sci. USA 1982 vol. 79: p. 1979-1983).*
Holm et al. (Mol. Immunol. Feb. 2007; 44 (6): 1075-1084).*
Onda, M. et al.; "New monoclonal antibodies to mesothelin useful for immunohistochemistry, fluorescence-activated cell sorting, Western blotting, and ELISA;" Clin. Cancer Res., vol. 11, No. 16, pp. 5840-5846, Aug. 15, 2005.
Chang, K. et al.; "Molecular cloning of mesothelin, a differentiation antigen present on mesothelium, mesotheliomas, and ovarian cancer;" Proc. Natl. Acad. Sci., vol. 93, pp. 136-140, Jan. 9, 1996.
Hassan, R. et al.; "Mesothelin targeted cancer immunotherapy;" European Journal of Cancer, vol. 44, No. 1, pp. 46-53, Oct. 22, 2007.
Heather L. Beyer, Ryan D. Geschwindt, Curtis L. Glover, Ly Tran, Ingegerd Hellstrom, Karl-Erik Hellstrom, M. Craig Miller, Thorsten Verch, W. Jeffrey Allard, Harvey I. Pass, Niranjan Y. Sardesai, "MesomarkTM: A Potential Test for Malignant Pleural Mesothelioma," Clinical Chemistry, vol. 53, No. 4, pp. 666-672 (Apr. 2007).
Ingegerd Hellstrom, John Raycraft, Sandra Kanan, Niranjan Y. Sardesai, Thorsten Verch, Yi Yang, and Karl Erik Hellstrom, "Mesothelin Variant 1 Is Released from Tumor Cells as a Diagnostic Marker," Cancer Epidemiol Biomarkers Prey, vol. 15, No. 5, pp. 1014-1020 (May 2006).
Nathalie Scholler, Barbara Garvik, Martha Hayden-Ledbetter, Toni Kline, Nicole Urban, "Development of a CA125-mesothelin cell adhesion assay as a screening tool for biologics discovery," Cancer Letters, vol. 247, No. 1, pp. 130-136 (Mar. 2007).
English Translation of Final Rejection for Japanese Patent Application 2010-535269 (corresponding to the present application) mailed on Mar. 4, 2014.

\* cited by examiner

*Primary Examiner* — Brad Duffy
(74) *Attorney, Agent, or Firm* — Thomas C. Blankinship

(57) ABSTRACT

The present invention provides recombinant antigen-binding regions and antibodies and functional fragments containing such antigen-binding regions that are specific for the membrane-anchored, 4O.kDa mesothelin polypeptide, which is overexpressed in several tumors, such as pancreatic and ovarian tumors, mesothelioma and lung cancer cells. These antibodies, accordingly, can be used to treat these and other disorders and conditions. Antibodies of the invention also can be used in the diagnostics field, as well as for further investigating the role of mesothelin in the progression of disorders associated with cancer. The invention also provides nucleic acid sequences encoding the foregoing antibodies, vectors containing the same, pharmaceutical compositions and kits with instructions for use.

5 Claims, 4 Drawing Sheets

SEQUENCE LISTING

<160> NUMBER OF SEQ ID NOS: 371

<210> SEQ ID NO 1
<211> LENGTH: 10
<212> TYPE: PRT
<213> ORGANISM: Homo sapiens

<400> SEQUENCE: 1

Gly Tyr Ser Phe Thr Asn Tyr Trp Ile Gly
1               5                   10

<210> SEQ ID NO 2
<211> LENGTH: 10

```
<212> TYPE: PRT
<213> ORGANISM: Homo sapiens

<400> SEQUENCE: 2

Gly Phe Thr Phe Ser Asp Tyr Ala Met Ser
1               5                   10

<210> SEQ ID NO 3
<211> LENGTH: 10
<212> TYPE: PRT
<213> ORGANISM: Homo sapiens

<400> SEQUENCE: 3

Gly Tyr Thr Phe Thr Gly Asn Tyr Ile Asn
1               5                   10

<210> SEQ ID NO 4
<211> LENGTH: 10
<212> TYPE: PRT
<213> ORGANISM: Homo sapiens

<400> SEQUENCE: 4

Gly Gly Thr Phe Ser Ser Tyr Tyr Phe Ser
1               5                   10

<210> SEQ ID NO 5
<211> LENGTH: 10
<212> TYPE: PRT
<213> ORGANISM: Homo sapiens

<400> SEQUENCE: 5

Gly Tyr Ser Phe Thr Ser Tyr Trp Ile Gly
1               5                   10

<210> SEQ ID NO 6
<211> LENGTH: 10
<212> TYPE: PRT
<213> ORGANISM: Homo sapiens

<400> SEQUENCE: 6

Gly Gly Ser Ile Ser Asn Tyr Tyr Trp Ser
1               5                   10

<210> SEQ ID NO 7
<211> LENGTH: 10
<212> TYPE: PRT
<213> ORGANISM: Homo sapiens

<400> SEQUENCE: 7

Gly Phe Thr Phe Ser Ser Tyr Gly Met Ser
1               5                   10

<210> SEQ ID NO 8
<211> LENGTH: 10
<212> TYPE: PRT
<213> ORGANISM: Homo sapiens

<400> SEQUENCE: 8

Gly Phe Thr Phe Ser Asn Ser Trp Met Ser
1               5                   10

<210> SEQ ID NO 9
<211> LENGTH: 10
<212> TYPE: PRT
<213> ORGANISM: Homo sapiens
```

<400> SEQUENCE: 9

Gly Gly Thr Phe Ser Asn Tyr Ser Ile Ser
1               5                   10

<210> SEQ ID NO 10
<211> LENGTH: 10
<212> TYPE: PRT
<213> ORGANISM: Homo sapiens

<400> SEQUENCE: 10

Gly Tyr Thr Phe Thr Ser Tyr Ala Leu His
1               5                   10

<210> SEQ ID NO 11
<211> LENGTH: 12
<212> TYPE: PRT
<213> ORGANISM: Homo sapiens

<400> SEQUENCE: 11

Gly Asp Ser Val Ser Ser Arg Ser Ala Ala Trp Gly
1               5                   10

<210> SEQ ID NO 12
<211> LENGTH: 10
<212> TYPE: PRT
<213> ORGANISM: Homo sapiens

<400> SEQUENCE: 12

Gly Gly Thr Phe Ser Asn Tyr Ser Leu His
1               5                   10

<210> SEQ ID NO 13
<211> LENGTH: 10
<212> TYPE: PRT
<213> ORGANISM: Homo sapiens

<400> SEQUENCE: 13

Gly Phe Thr Phe Ser Ser Tyr Ala Met Asn
1               5                   10

<210> SEQ ID NO 14
<211> LENGTH: 10
<212> TYPE: PRT
<213> ORGANISM: Homo sapiens

<400> SEQUENCE: 14

Gly Tyr Thr Phe Thr Ile Tyr Asp Met His
1               5                   10

<210> SEQ ID NO 15
<211> LENGTH: 12
<212> TYPE: PRT
<213> ORGANISM: Homo sapiens

<400> SEQUENCE: 15

Gly Asp Ser Val Ser Ser Asn Ser Ala Ala Trp Gly
1               5                   10

<210> SEQ ID NO 16
<211> LENGTH: 9
<212> TYPE: PRT
<213> ORGANISM: Homo sapiens

<400> SEQUENCE: 16

Gly Tyr Ser Phe Asn Thr Ser Trp Ile
1               5

<210> SEQ ID NO 17
<211> LENGTH: 12
<212> TYPE: PRT
<213> ORGANISM: Homo sapiens

<400> SEQUENCE: 17

Gly Asp Ser Val Ser Ser Asn Ser Ala Ala Trp Ser
1               5                   10

<210> SEQ ID NO 18
<211> LENGTH: 10
<212> TYPE: PRT
<213> ORGANISM: Homo sapiens

<400> SEQUENCE: 18

Gly Tyr Ser Phe Thr Thr Tyr Trp Ile Gly
1               5                   10

<210> SEQ ID NO 19
<211> LENGTH: 12
<212> TYPE: PRT
<213> ORGANISM: Homo sapiens

<400> SEQUENCE: 19

Gly Asp Ser Val Ser Ser Asn Ser Ala Ser Trp Ser
1               5                   10

<210> SEQ ID NO 20
<211> LENGTH: 10
<212> TYPE: PRT
<213> ORGANISM: Homo sapiens

<400> SEQUENCE: 20

Gly Phe Thr Phe Ser Thr Tyr Ala Met Ser
1               5                   10

<210> SEQ ID NO 21
<211> LENGTH: 10
<212> TYPE: PRT
<213> ORGANISM: Homo sapiens

<400> SEQUENCE: 21

Gly Phe Thr Phe Ser Arg Tyr Ala Ile Ser
1               5                   10

<210> SEQ ID NO 22
<211> LENGTH: 10
<212> TYPE: PRT
<213> ORGANISM: Homo sapiens

<400> SEQUENCE: 22

Gly Gly Thr Phe Ser Ser Tyr Tyr Ile Ser
1               5                   10

<210> SEQ ID NO 23
<211> LENGTH: 10
<212> TYPE: PRT
<213> ORGANISM: Homo sapiens

<400> SEQUENCE: 23

Gly Gly Thr Phe Ser Ser His Ala Ile Ser

<210> SEQ ID NO 24
<211> LENGTH: 12
<212> TYPE: PRT
<213> ORGANISM: Homo sapiens

<400> SEQUENCE: 24

Gly Asp Ser Val Ser Ser Asn Thr Ala Ala Trp Ser
1               5                   10

<210> SEQ ID NO 25
<211> LENGTH: 12
<212> TYPE: PRT
<213> ORGANISM: Homo sapiens

<400> SEQUENCE: 25

Gly Phe Ser Leu Ser Ser Ser Gly Val Gly Val Ser
1               5                   10

<210> SEQ ID NO 26
<211> LENGTH: 12
<212> TYPE: PRT
<213> ORGANISM: Homo sapiens

<400> SEQUENCE: 26

Gly Asp Ser Val Ser Ser Ser Ala Ala Trp Ser
1               5                   10

<210> SEQ ID NO 27
<211> LENGTH: 9
<212> TYPE: PRT
<213> ORGANISM: Homo sapiens

<400> SEQUENCE: 27

Gly Phe Thr Phe Ser Ser His Tyr Ser
1               5

<210> SEQ ID NO 28
<211> LENGTH: 10
<212> TYPE: PRT
<213> ORGANISM: Homo sapiens

<400> SEQUENCE: 28

Gly Gly Thr Phe Ser Asn Tyr Thr Ile Ser
1               5                   10

<210> SEQ ID NO 29
<211> LENGTH: 9
<212> TYPE: PRT
<213> ORGANISM: Homo sapiens

<400> SEQUENCE: 29

Gly Phe Thr Phe Ser Ser Tyr Tyr Ser
1               5

<210> SEQ ID NO 30
<211> LENGTH: 10
<212> TYPE: PRT
<213> ORGANISM: Homo sapiens

<400> SEQUENCE: 30

Gly Phe Thr Phe Ser Asn Tyr Gly Ile His
1               5                   10

<210> SEQ ID NO 31
<211> LENGTH: 20
<212> TYPE: PRT
<213> ORGANISM: Homo sapiens

<400> SEQUENCE: 31

Trp Met Gly Val Ile Met Pro Ser Asp Ser Tyr Thr Arg Tyr Ser Pro
1               5                   10                  15
Ser Phe Gln Gly
            20

<210> SEQ ID NO 32
<211> LENGTH: 20
<212> TYPE: PRT
<213> ORGANISM: Homo sapiens

<400> SEQUENCE: 32

Trp Met Gly Phe Ile Trp Pro Val Asp Ser Trp Thr Gln Tyr Ser Pro
1               5                   10                  15
Ser Phe Gln Gly
            20

<210> SEQ ID NO 33
<211> LENGTH: 20
<212> TYPE: PRT
<213> ORGANISM: Homo sapiens

<400> SEQUENCE: 33

Trp Met Gly Ile Ile Trp Pro Ile Asp Ser Phe Thr Gln Tyr Ser Pro
1               5                   10                  15
Ser Phe Gln Gly
            20

<210> SEQ ID NO 34
<211> LENGTH: 20
<212> TYPE: PRT
<213> ORGANISM: Homo sapiens

<400> SEQUENCE: 34

Trp Val Ser Ala Ile Met Tyr Asp Ser Ser Thr Phe Tyr Ala Asp
1               5                   10                  15
Ser Val Lys Gly
            20

<210> SEQ ID NO 35
<211> LENGTH: 20
<212> TYPE: PRT
<213> ORGANISM: Homo sapiens

<400> SEQUENCE: 35

Trp Met Gly Ile Ile Asn Pro His Gly Gly Asp Thr Lys Tyr Ala Gln
1               5                   10                  15
Lys Phe Gln Gly
            20

<210> SEQ ID NO 36
<211> LENGTH: 20
<212> TYPE: PRT
<213> ORGANISM: Homo sapiens

<400> SEQUENCE: 36

Trp Met Gly Ile Ile Asn Pro Thr Lys Gly Trp Thr Leu Tyr Ala Gln

```
1               5                   10                  15
Lys Phe Gln Gly
            20

<210> SEQ ID NO 37
<211> LENGTH: 20
<212> TYPE: PRT
<213> ORGANISM: Homo sapiens

<400> SEQUENCE: 37

Trp Met Gly Ile Ile Asn Pro Thr Lys Gly Trp Thr Leu Tyr Ala Gln
1               5                   10                  15
Lys Phe Gln Gly
            20

<210> SEQ ID NO 38
<211> LENGTH: 20
<212> TYPE: PRT
<213> ORGANISM: Homo sapiens

<400> SEQUENCE: 38

Trp Met Gly Gly Ile Ile Pro Lys Phe Gly Ser Ala Asn Tyr Ala Gln
1               5                   10                  15
Lys Phe Gln Gly
            20

<210> SEQ ID NO 39
<211> LENGTH: 20
<212> TYPE: PRT
<213> ORGANISM: Homo sapiens

<400> SEQUENCE: 39

Trp Met Gly Ile Ile Asp Pro Gly Asp Ser Arg Thr Arg Tyr Ser Pro
1               5                   10                  15
Ser Phe Gln Gly
            20

<210> SEQ ID NO 40
<211> LENGTH: 19
<212> TYPE: PRT
<213> ORGANISM: Homo sapiens

<400> SEQUENCE: 40

Trp Ile Gly Glu Ile Tyr His Ser Gly Gly Thr Tyr Tyr Asn Pro Ser
1               5                   10                  15
Leu Lys Gly

<210> SEQ ID NO 41
<211> LENGTH: 20
<212> TYPE: PRT
<213> ORGANISM: Homo sapiens

<400> SEQUENCE: 41

Trp Val Ser Gly Ile Ser Tyr Ser Ser Ser Ala Thr Tyr Tyr Ala Asp
1               5                   10                  15
Ser Val Lys Gly
            20

<210> SEQ ID NO 42
<211> LENGTH: 20
<212> TYPE: PRT
<213> ORGANISM: Homo sapiens
```

<400> SEQUENCE: 42

Trp Val Ser Ala Ile Thr Tyr Trp Gly Ser Asn Thr Tyr Tyr Ala Asp
1               5                   10                  15

Ser Val Lys Gly
            20

<210> SEQ ID NO 43
<211> LENGTH: 20
<212> TYPE: PRT
<213> ORGANISM: Homo sapiens

<400> SEQUENCE: 43

Trp Met Gly Arg Ile Ile Pro Asn Phe Gly Thr Ala Asn Tyr Ala Gln
1               5                   10                  15

Lys Phe Gln Gly
            20

<210> SEQ ID NO 44
<211> LENGTH: 20
<212> TYPE: PRT
<213> ORGANISM: Homo sapiens

<400> SEQUENCE: 44

Trp Met Gly Ile Ile Asn Pro Gln Asn Gly Gly Thr Asn Tyr Ala Gln
1               5                   10                  15

Lys Phe Gln Gly
            20

<210> SEQ ID NO 45
<211> LENGTH: 20
<212> TYPE: PRT
<213> ORGANISM: Homo sapiens

<400> SEQUENCE: 45

Trp Met Gly Ile Ile Asp Pro Arg Glu Ser Phe Thr Arg Tyr Ser Pro
1               5                   10                  15

Ser Phe Gln Gly
            20

<210> SEQ ID NO 46
<211> LENGTH: 21
<212> TYPE: PRT
<213> ORGANISM: Homo sapiens

<400> SEQUENCE: 46

Trp Leu Gly Arg Ile Gly Tyr Arg Ser Lys Trp Met Asn Asp Tyr Ala
1               5                   10                  15

Val Ser Val Lys Ser
            20

<210> SEQ ID NO 47
<211> LENGTH: 20
<212> TYPE: PRT
<213> ORGANISM: Homo sapiens

<400> SEQUENCE: 47

Trp Met Gly Gly Ile Val Pro Ile Phe Gly Thr Ala Asn Tyr Ala Gln
1               5                   10                  15

Lys Phe Gln Gly
            20

```
<210> SEQ ID NO 48
<211> LENGTH: 20
<212> TYPE: PRT
<213> ORGANISM: Homo sapiens

<400> SEQUENCE: 48

Trp Val Ser Gly Ile Ser Gly Asn Gly Ser Asn Thr Tyr Tyr Ala Asp
1               5                   10                  15

Ser Val Lys Gly
            20

<210> SEQ ID NO 49
<211> LENGTH: 20
<212> TYPE: PRT
<213> ORGANISM: Homo sapiens

<400> SEQUENCE: 49

Trp Met Gly Tyr Ile Ser Pro Tyr Ser Gly Asp Thr Asn Tyr Ala Gln
1               5                   10                  15

Lys Phe Gln Gly
            20

<210> SEQ ID NO 50
<211> LENGTH: 21
<212> TYPE: PRT
<213> ORGANISM: Homo sapiens

<400> SEQUENCE: 50

Trp Leu Gly Arg Ile Ser Tyr Arg Ser Arg Tyr Asn Asn Tyr Ala
1               5                   10                  15

Val Ser Val Lys Ser
            20

<210> SEQ ID NO 51
<211> LENGTH: 20
<212> TYPE: PRT
<213> ORGANISM: Homo sapiens

<400> SEQUENCE: 51

Trp Met Gly Ile Ile His Pro Gly His Ser Tyr Thr Arg Tyr Ser Pro
1               5                   10                  15

Ser Phe Gln Gly
            20

<210> SEQ ID NO 52
<211> LENGTH: 22
<212> TYPE: PRT
<213> ORGANISM: Homo sapiens

<400> SEQUENCE: 52

Trp Leu Gly Arg Ile Tyr Tyr Arg Ser Lys Lys Trp Tyr Asn Asp Tyr
1               5                   10                  15

Ala Val Ser Val Lys Ser
            20

<210> SEQ ID NO 53
<211> LENGTH: 21
<212> TYPE: PRT
<213> ORGANISM: Homo sapiens

<400> SEQUENCE: 53

Trp Leu Gly Arg Ile Gln Tyr Arg Ser Lys Trp Tyr Asn Ala Tyr Ala
```

```
1               5                   10                  15
Val Ser Val Lys Ser
            20

<210> SEQ ID NO 54
<211> LENGTH: 20
<212> TYPE: PRT
<213> ORGANISM: Homo sapiens

<400> SEQUENCE: 54

Trp Met Gly Phe Ile Tyr Pro Asp Lys Ser Tyr Thr Asn Tyr Ser Pro
1               5                   10                  15

Ser Phe Gln Gly
            20

<210> SEQ ID NO 55
<211> LENGTH: 21
<212> TYPE: PRT
<213> ORGANISM: Homo sapiens

<400> SEQUENCE: 55

Trp Leu Gly Arg Ile Tyr Tyr Arg Ser Gln Trp Tyr Asn Asp Tyr Ala
1               5                   10                  15

Val Ser Val Lys Ser
            20

<210> SEQ ID NO 56
<211> LENGTH: 20
<212> TYPE: PRT
<213> ORGANISM: Homo sapiens

<400> SEQUENCE: 56

Trp Val Ser Phe Ile Ser Gly Tyr Gly Ser Ser Thr Tyr Tyr Ala Asp
1               5                   10                  15

Ser Val Lys Gly
            20

<210> SEQ ID NO 57
<211> LENGTH: 20
<212> TYPE: PRT
<213> ORGANISM: Homo sapiens

<400> SEQUENCE: 57

Trp Val Ser Ser Ile Ser Gly Gly Gly Ser Lys Thr Phe Tyr Ala Asp
1               5                   10                  15

Ser Val Lys Gly
            20

<210> SEQ ID NO 58
<211> LENGTH: 20
<212> TYPE: PRT
<213> ORGANISM: Homo sapiens

<400> SEQUENCE: 58

Trp Met Gly Gly Ile Ile Pro Lys Phe Gly Thr Ala Asn Tyr Ala Gln
1               5                   10                  15

Lys Phe Gln Gly
            20

<210> SEQ ID NO 59
<211> LENGTH: 20
<212> TYPE: PRT
```

<213> ORGANISM: Homo sapiens

<400> SEQUENCE: 59

Trp Met Gly Asn Ile Met Pro Ile Phe Gly Val Ala Asn Tyr Ala Gln
1               5                   10                  15

Lys Phe Gln Gly
            20

<210> SEQ ID NO 60
<211> LENGTH: 21
<212> TYPE: PRT
<213> ORGANISM: Homo sapiens

<400> SEQUENCE: 60

Trp Leu Gly Arg Ile Arg Tyr Arg Ser Lys Trp Tyr Asn Asp Tyr Ala
1               5                   10                  15

Val Ser Val Lys Ser
            20

<210> SEQ ID NO 61
<211> LENGTH: 19
<212> TYPE: PRT
<213> ORGANISM: Homo sapiens

<400> SEQUENCE: 61

Trp Leu Ala Leu Ile Asp Trp Asp Asp Lys Ser Tyr Ser Thr Ser
1               5                   10                  15

Leu Lys Thr

<210> SEQ ID NO 62
<211> LENGTH: 21
<212> TYPE: PRT
<213> ORGANISM: Homo sapiens

<400> SEQUENCE: 62

Trp Leu Gly Arg Ile Gly Gln Arg Ser Lys Trp Tyr Asn Asp Tyr Ala
1               5                   10                  15

Val Ser Val Lys Ser
            20

<210> SEQ ID NO 63
<211> LENGTH: 20
<212> TYPE: PRT
<213> ORGANISM: Homo sapiens

<400> SEQUENCE: 63

Trp Val Ser Thr Ile Ser Ser Asn Gly Ser Tyr Thr Tyr Tyr Ala Asp
1               5                   10                  15

Ser Val Lys Gly
            20

<210> SEQ ID NO 64
<211> LENGTH: 20
<212> TYPE: PRT
<213> ORGANISM: Homo sapiens

<400> SEQUENCE: 64

Trp Met Gly Asn Ile Ile Pro Ala Phe Gly Tyr Ala Asn Tyr Ala Gln
1               5                   10                  15

Lys Phe Gln Gly
            20

<210> SEQ ID NO 65
<211> LENGTH: 20
<212> TYPE: PRT
<213> ORGANISM: Homo sapiens

<400> SEQUENCE: 65

Trp Val Ser Asn Ile Ser Gly Asn Gly Ser Ser Thr Tyr Tyr Ala Asp
1               5                   10                  15
Ser Val Lys Gly
            20

<210> SEQ ID NO 66
<211> LENGTH: 20
<212> TYPE: PRT
<213> ORGANISM: Homo sapiens

<400> SEQUENCE: 66

Trp Val Ser Tyr Ile Arg Ser Gly Ser Ser Asp Thr Tyr Tyr Ala Asp
1               5                   10                  15
Ser Val Lys Gly
            20

<210> SEQ ID NO 67
<211> LENGTH: 12
<212> TYPE: PRT
<213> ORGANISM: Homo sapiens

<400> SEQUENCE: 67

Tyr Gly His Gly Met Tyr Gly Gly Ala Leu Asp Val
1               5                   10

<210> SEQ ID NO 68
<211> LENGTH: 12
<212> TYPE: PRT
<213> ORGANISM: Homo sapiens

<400> SEQUENCE: 68

Ile Asn Tyr Ile Tyr Lys Gly Val His Phe Asp Tyr
1               5                   10

<210> SEQ ID NO 69
<211> LENGTH: 10
<212> TYPE: PRT
<213> ORGANISM: Homo sapiens

<400> SEQUENCE: 69

Trp His His Gly Thr Trp Ile Phe Asp Tyr
1               5                   10

<210> SEQ ID NO 70
<211> LENGTH: 6
<212> TYPE: PRT
<213> ORGANISM: Homo sapiens

<400> SEQUENCE: 70

Arg Thr Ser Met Asp Tyr
1               5

<210> SEQ ID NO 71
<211> LENGTH: 11
<212> TYPE: PRT
<213> ORGANISM: Homo sapiens

<400> SEQUENCE: 71

```
Gly Gln Leu Tyr Gly Gly Thr Tyr Met Asp Gly
1               5                   10
```

<210> SEQ ID NO 72
<211> LENGTH: 8
<212> TYPE: PRT
<213> ORGANISM: Homo sapiens

<400> SEQUENCE: 72

```
Pro Met Asp Asn Leu Pro Asp Ile
1               5
```

<210> SEQ ID NO 73
<211> LENGTH: 7
<212> TYPE: PRT
<213> ORGANISM: Homo sapiens

<400> SEQUENCE: 73

```
Tyr Leu Tyr Tyr Phe Asp Val
1               5
```

<210> SEQ ID NO 74
<211> LENGTH: 6
<212> TYPE: PRT
<213> ORGANISM: Homo sapiens

<400> SEQUENCE: 74

```
Thr Lys Phe Phe Ala Asn
1               5
```

<210> SEQ ID NO 75
<211> LENGTH: 6
<212> TYPE: PRT
<213> ORGANISM: Homo sapiens

<400> SEQUENCE: 75

```
Gly Ile Tyr Phe Ala Phe
1               5
```

<210> SEQ ID NO 76
<211> LENGTH: 11
<212> TYPE: PRT
<213> ORGANISM: Homo sapiens

<400> SEQUENCE: 76

```
Lys His Lys Tyr Arg Ile Gly Ser Met Asp Val
1               5                   10
```

<210> SEQ ID NO 77
<211> LENGTH: 8
<212> TYPE: PRT
<213> ORGANISM: Homo sapiens

<400> SEQUENCE: 77

```
Tyr Met Lys Gly Gly Tyr Asp Tyr
1               5
```

<210> SEQ ID NO 78
<211> LENGTH: 8
<212> TYPE: PRT
<213> ORGANISM: Homo sapiens

<400> SEQUENCE: 78

```
Met Gln Gly Phe Gln Leu Asp Tyr
```

```
<210> SEQ ID NO 79
<211> LENGTH: 6
<212> TYPE: PRT
<213> ORGANISM: Homo sapiens

<400> SEQUENCE: 79

Thr Tyr Thr Phe Ala Val
1               5

<210> SEQ ID NO 80
<211> LENGTH: 7
<212> TYPE: PRT
<213> ORGANISM: Homo sapiens

<400> SEQUENCE: 80

Lys Trp Leu Phe Tyr Asp Tyr
1               5

<210> SEQ ID NO 81
<211> LENGTH: 5
<212> TYPE: PRT
<213> ORGANISM: Homo sapiens

<400> SEQUENCE: 81

Gly Trp Gln Asp Phe
1               5

<210> SEQ ID NO 82
<211> LENGTH: 14
<212> TYPE: PRT
<213> ORGANISM: Homo sapiens

<400> SEQUENCE: 82

Tyr Tyr Ser Asp His Phe Gly Leu Tyr Pro Tyr Phe Asp Tyr
1               5                   10

<210> SEQ ID NO 83
<211> LENGTH: 18
<212> TYPE: PRT
<213> ORGANISM: Homo sapiens

<400> SEQUENCE: 83

Gly Asp Gly Gly Pro Ser Ser Gln Gly Asn Tyr Phe Gly Trp Val Tyr
1               5                   10                  15

Asp Val

<210> SEQ ID NO 84
<211> LENGTH: 12
<212> TYPE: PRT
<213> ORGANISM: Homo sapiens

<400> SEQUENCE: 84

Asn Tyr Ser Gly Pro Met Tyr Tyr Gly Asp Val
1               5                   10

<210> SEQ ID NO 85
<211> LENGTH: 11
<212> TYPE: PRT
<213> ORGANISM: Homo sapiens

<400> SEQUENCE: 85

Gly Phe His Gly Ser Thr Met Tyr Phe Asp Val
```

<210> SEQ ID NO 86
<211> LENGTH: 8
<212> TYPE: PRT
<213> ORGANISM: Homo sapiens

<400> SEQUENCE: 86

Gly Leu Gly Gly Ser Phe Asp Val
1               5

<210> SEQ ID NO 87
<211> LENGTH: 11
<212> TYPE: PRT
<213> ORGANISM: Homo sapiens

<400> SEQUENCE: 87

Gly Trp Ile Thr Gly Trp Arg Ile Phe Asp Tyr
1               5                   10

<210> SEQ ID NO 88
<211> LENGTH: 11
<212> TYPE: PRT
<213> ORGANISM: Homo sapiens

<400> SEQUENCE: 88

Lys Met Tyr Trp Trp Ser Asp Gly Phe Asp Tyr
1               5                   10

<210> SEQ ID NO 89
<211> LENGTH: 12
<212> TYPE: PRT
<213> ORGANISM: Homo sapiens

<400> SEQUENCE: 89

Tyr Pro Gly Pro Thr Gly His Val Phe Phe Asp Ile
1               5                   10

<210> SEQ ID NO 90
<211> LENGTH: 12
<212> TYPE: PRT
<213> ORGANISM: Homo sapiens

<400> SEQUENCE: 90

Tyr Pro Gly Pro Thr Gly His Val Phe Phe Asp Ile
1               5                   10

<210> SEQ ID NO 91
<211> LENGTH: 6
<212> TYPE: PRT
<213> ORGANISM: Homo sapiens

<400> SEQUENCE: 91

Glu Met Arg Leu Ala Tyr
1               5

<210> SEQ ID NO 92
<211> LENGTH: 14
<212> TYPE: PRT
<213> ORGANISM: Homo sapiens

<400> SEQUENCE: 92

Gly Tyr His Gln Gly Leu Tyr Gly Asn His Met Phe Asp Val
1               5                   10

```
<210> SEQ ID NO 93
<211> LENGTH: 8
<212> TYPE: PRT
<213> ORGANISM: Homo sapiens

<400> SEQUENCE: 93

Ile Gln Gly Trp Asn Tyr Asp Val
1               5

<210> SEQ ID NO 94
<211> LENGTH: 8
<212> TYPE: PRT
<213> ORGANISM: Homo sapiens

<400> SEQUENCE: 94

Ser Arg Phe Gly Tyr Phe Asp Val
1               5

<210> SEQ ID NO 95
<211> LENGTH: 10
<212> TYPE: PRT
<213> ORGANISM: Homo sapiens

<400> SEQUENCE: 95

Phe Val Ala Arg Leu Asn Val Phe Asp Tyr
1               5                   10

<210> SEQ ID NO 96
<211> LENGTH: 6
<212> TYPE: PRT
<213> ORGANISM: Homo sapiens

<400> SEQUENCE: 96

Lys Phe Thr Phe Asp Val
1               5

<210> SEQ ID NO 97
<211> LENGTH: 10
<212> TYPE: PRT
<213> ORGANISM: Homo sapiens

<400> SEQUENCE: 97

Leu Ile Ala Thr Leu Gly Thr Phe Asp Tyr
1               5                   10

<210> SEQ ID NO 98
<211> LENGTH: 11
<212> TYPE: PRT
<213> ORGANISM: Homo sapiens

<400> SEQUENCE: 98

Thr Ala Pro Ala Gly His Gly Val Phe Ala Asn
1               5                   10

<210> SEQ ID NO 99
<211> LENGTH: 12
<212> TYPE: PRT
<213> ORGANISM: Homo sapiens

<400> SEQUENCE: 99

Arg Ala Ser Gln Ser Val Arg Ser Arg Leu Ala
1               5                   10

<210> SEQ ID NO 100
```

```
<211> LENGTH: 11
<212> TYPE: PRT
<213> ORGANISM: Homo sapiens

<400> SEQUENCE: 100

Arg Ala Ser Gln Ile Val Ser Gly Tyr Leu Ala
1               5                   10

<210> SEQ ID NO 101
<211> LENGTH: 13
<212> TYPE: PRT
<213> ORGANISM: Homo sapiens

<400> SEQUENCE: 101

Ser Gly Ser Ser Ser Asn Ile Gly Ser Asn Tyr Val Ser
1               5                   10

<210> SEQ ID NO 102
<211> LENGTH: 14
<212> TYPE: PRT
<213> ORGANISM: Homo sapiens

<400> SEQUENCE: 102

Thr Gly Thr Ser Ser Asp Val Gly Gly Tyr Asn Tyr Val Ser
1               5                   10

<210> SEQ ID NO 103
<211> LENGTH: 14
<212> TYPE: PRT
<213> ORGANISM: Homo sapiens

<400> SEQUENCE: 103

Thr Gly Thr Ser Ser Asp Ile Gly Gly Tyr Asn Ser Val Ser
1               5                   10

<210> SEQ ID NO 104
<211> LENGTH: 11
<212> TYPE: PRT
<213> ORGANISM: Homo sapiens

<400> SEQUENCE: 104

Arg Ala Ser Gln Asn Ile Gly Ser Tyr Leu Asn
1               5                   10

<210> SEQ ID NO 105
<211> LENGTH: 14
<212> TYPE: PRT
<213> ORGANISM: Homo sapiens

<400> SEQUENCE: 105

Thr Gly Thr Ser Ser Asp Val Gly Ala Ser Asp Thr Val Thr
1               5                   10

<210> SEQ ID NO 106
<211> LENGTH: 16
<212> TYPE: PRT
<213> ORGANISM: Homo sapiens

<400> SEQUENCE: 106

Arg Ser Ser Gln Ser Leu Leu His Ser Asn Gly Tyr Thr Tyr Leu Ser
1               5                   10                  15

<210> SEQ ID NO 107
<211> LENGTH: 13
<212> TYPE: PRT
```

<213> ORGANISM: Homo sapiens

<400> SEQUENCE: 107

Ser Gly Ser Ser Ser Asn Ile Gly Pro Asn Tyr Val Ser
1               5                   10

<210> SEQ ID NO 108
<211> LENGTH: 12
<212> TYPE: PRT
<213> ORGANISM: Homo sapiens

<400> SEQUENCE: 108

Arg Ala Ser Gln Ser Leu Thr Ser Asn Gln Leu Ala
1               5                   10

<210> SEQ ID NO 109
<211> LENGTH: 14
<212> TYPE: PRT
<213> ORGANISM: Homo sapiens

<400> SEQUENCE: 109

Thr Gly Thr Ser Ser Asp Val Gly Gly Asn Asn Phe Val Ser
1               5                   10

<210> SEQ ID NO 110
<211> LENGTH: 11
<212> TYPE: PRT
<213> ORGANISM: Homo sapiens

<400> SEQUENCE: 110

Arg Ala Ser Gln Thr Ile Ser Ser Ala Leu Ala
1               5                   10

<210> SEQ ID NO 111
<211> LENGTH: 14
<212> TYPE: PRT
<213> ORGANISM: Homo sapiens

<400> SEQUENCE: 111

Thr Gly Thr Ser Ser Asp Val Gly Asn Phe Asn Tyr Val Asn
1               5                   10

<210> SEQ ID NO 112
<211> LENGTH: 12
<212> TYPE: PRT
<213> ORGANISM: Homo sapiens

<400> SEQUENCE: 112

Arg Ala Ser Gln Ser Val Thr Ser Asn Tyr Leu Ala
1               5                   10

<210> SEQ ID NO 113
<211> LENGTH: 11
<212> TYPE: PRT
<213> ORGANISM: Homo sapiens

<400> SEQUENCE: 113

Arg Ala Ser Gln Ser Ile Asn Arg Ser Leu Thr
1               5                   10

<210> SEQ ID NO 114
<211> LENGTH: 14
<212> TYPE: PRT
<213> ORGANISM: Homo sapiens

<400> SEQUENCE: 114

Thr Gly Thr Ser Ser Asp Ile Gly Gly Phe Asn Tyr Val Ser
1               5                   10

<210> SEQ ID NO 115
<211> LENGTH: 11
<212> TYPE: PRT
<213> ORGANISM: Homo sapiens

<400> SEQUENCE: 115

Ser Gly Asp Asn Ile Pro Asn Phe Tyr Val His
1               5                   10

<210> SEQ ID NO 116
<211> LENGTH: 14
<212> TYPE: PRT
<213> ORGANISM: Homo sapiens

<400> SEQUENCE: 116

Thr Gly Thr Ser Ser Asp Ile Gly Arg Tyr His Tyr Val Ser
1               5                   10

<210> SEQ ID NO 117
<211> LENGTH: 13
<212> TYPE: PRT
<213> ORGANISM: Homo sapiens

<400> SEQUENCE: 117

Ser Gly Ser Ser Ser Asn Ile Gly Asn Asn Ser Val Asn
1               5                   10

<210> SEQ ID NO 118
<211> LENGTH: 14
<212> TYPE: PRT
<213> ORGANISM: Homo sapiens

<400> SEQUENCE: 118

Thr Gly Thr Ser Ser Asp Val Gly Asp Tyr Asn Tyr Val Ser
1               5                   10

<210> SEQ ID NO 119
<211> LENGTH: 14
<212> TYPE: PRT
<213> ORGANISM: Homo sapiens

<400> SEQUENCE: 119

Thr Gly Thr Ser Ser Asp Val Gly Asp Tyr Asn Tyr Val Ser
1               5                   10

<210> SEQ ID NO 120
<211> LENGTH: 11
<212> TYPE: PRT
<213> ORGANISM: Homo sapiens

<400> SEQUENCE: 120

Ser Gly Asp Asn Leu Arg Ser Lys Tyr Ala His
1               5                   10

<210> SEQ ID NO 121
<211> LENGTH: 11
<212> TYPE: PRT
<213> ORGANISM: Homo sapiens

<400> SEQUENCE: 121

Ser Gly Asp Asn Ile Gly Ser Lys Val Ala Thr
1               5                   10

<210> SEQ ID NO 122
<211> LENGTH: 14
<212> TYPE: PRT
<213> ORGANISM: Homo sapiens

<400> SEQUENCE: 122

Thr Gly Thr Ser Ser Asp Ile Gly His Phe Asn Tyr Val Ser
1               5                   10

<210> SEQ ID NO 123
<211> LENGTH: 13
<212> TYPE: PRT
<213> ORGANISM: Homo sapiens

<400> SEQUENCE: 123

Ser Gly Ser Ser Ser Asn Ile Gly Ser His Thr Val Asn
1               5                   10

<210> SEQ ID NO 124
<211> LENGTH: 13
<212> TYPE: PRT
<213> ORGANISM: Homo sapiens

<400> SEQUENCE: 124

Ser Gly Ser Ser Ser Asn Ile Gly Asn Asn Arg Val Ser
1               5                   10

<210> SEQ ID NO 125
<211> LENGTH: 14
<212> TYPE: PRT
<213> ORGANISM: Homo sapiens

<400> SEQUENCE: 125

Thr Gly Thr Ser Ser Asp Ile Gly Thr Tyr Asn His Val Ser
1               5                   10

<210> SEQ ID NO 126
<211> LENGTH: 14
<212> TYPE: PRT
<213> ORGANISM: Homo sapiens

<400> SEQUENCE: 126

Thr Gly Ser Ser Ser Asn Ile Gly Ile Gly Tyr Asp Val Asn
1               5                   10

<210> SEQ ID NO 127
<211> LENGTH: 14
<212> TYPE: PRT
<213> ORGANISM: Homo sapiens

<400> SEQUENCE: 127

Thr Gly Thr Ser Ser Asp Leu Gly Gly Tyr Tyr Val Ser
1               5                   10

<210> SEQ ID NO 128
<211> LENGTH: 13
<212> TYPE: PRT
<213> ORGANISM: Homo sapiens

<400> SEQUENCE: 128

Ser Gly Ser Ser Ser Asn Ile Gly Asn Tyr Arg Val Ser
1               5                   10

```
<210> SEQ ID NO 129
<211> LENGTH: 11
<212> TYPE: PRT
<213> ORGANISM: Homo sapiens

<400> SEQUENCE: 129

Leu Leu Ile Tyr Gly Ala Ser Lys Arg Ala Thr
1               5                   10

<210> SEQ ID NO 130
<211> LENGTH: 11
<212> TYPE: PRT
<213> ORGANISM: Homo sapiens

<400> SEQUENCE: 130

Leu Leu Ile Tyr Gly Ala Ser Ser Arg Ala Thr
1               5                   10

<210> SEQ ID NO 131
<211> LENGTH: 11
<212> TYPE: PRT
<213> ORGANISM: Homo sapiens

<400> SEQUENCE: 131

Leu Leu Ile Tyr Asn Asp Asn Gln Arg Pro Ser
1               5                   10

<210> SEQ ID NO 132
<211> LENGTH: 11
<212> TYPE: PRT
<213> ORGANISM: Homo sapiens

<400> SEQUENCE: 132

Leu Met Ile Tyr Ser Val Ser Lys Arg Pro Ser
1               5                   10

<210> SEQ ID NO 133
<211> LENGTH: 11
<212> TYPE: PRT
<213> ORGANISM: Homo sapiens

<400> SEQUENCE: 133

Leu Met Ile Tyr Gly Val Asn Asn Arg Pro Ser
1               5                   10

<210> SEQ ID NO 134
<211> LENGTH: 11
<212> TYPE: PRT
<213> ORGANISM: Homo sapiens

<400> SEQUENCE: 134

Leu Leu Ile Tyr Asn Ser Ser Thr Leu Gln Ser
1               5                   10

<210> SEQ ID NO 135
<211> LENGTH: 11
<212> TYPE: PRT
<213> ORGANISM: Homo sapiens

<400> SEQUENCE: 135

Leu Met Ile Tyr Ala Val Asn Lys Arg Pro Ser
1               5                   10
```

```
<210> SEQ ID NO 136
<211> LENGTH: 11
<212> TYPE: PRT
<213> ORGANISM: Homo sapiens

<400> SEQUENCE: 136

Leu Leu Ile Tyr Leu Gly Ser Lys Arg Ala Ser
1               5                   10

<210> SEQ ID NO 137
<211> LENGTH: 11
<212> TYPE: PRT
<213> ORGANISM: Homo sapiens

<400> SEQUENCE: 137

Leu Leu Ile His Gly Asn Ala Asn Arg Pro Ser
1               5                   10

<210> SEQ ID NO 138
<211> LENGTH: 11
<212> TYPE: PRT
<213> ORGANISM: Homo sapiens

<400> SEQUENCE: 138

Leu Leu Ile Tyr Asp Ser Ser Asn Arg Ala Thr
1               5                   10

<210> SEQ ID NO 139
<211> LENGTH: 11
<212> TYPE: PRT
<213> ORGANISM: Homo sapiens

<400> SEQUENCE: 139

Leu Met Ile Tyr Tyr Gly Asp Ser Arg Pro Ser
1               5                   10

<210> SEQ ID NO 140
<211> LENGTH: 11
<212> TYPE: PRT
<213> ORGANISM: Homo sapiens

<400> SEQUENCE: 140

Leu Leu Ile Tyr Gly Ala Ser Thr Leu Gln Ser
1               5                   10

<210> SEQ ID NO 141
<211> LENGTH: 11
<212> TYPE: PRT
<213> ORGANISM: Homo sapiens

<400> SEQUENCE: 141

Leu Met Ile Tyr Ser Val Ser Ser Arg Pro Ser
1               5                   10

<210> SEQ ID NO 142
<211> LENGTH: 11
<212> TYPE: PRT
<213> ORGANISM: Homo sapiens

<400> SEQUENCE: 142

Leu Leu Ile Tyr Gly Ser Ser Ser Arg Ala Thr
1               5                   10

<210> SEQ ID NO 143
<211> LENGTH: 11
```

```
<212> TYPE: PRT
<213> ORGANISM: Homo sapiens

<400> SEQUENCE: 143

Leu Leu Ile Tyr Ala Ala Ser Asn Leu Gln Ser
1               5                   10

<210> SEQ ID NO 144
<211> LENGTH: 11
<212> TYPE: PRT
<213> ORGANISM: Homo sapiens

<400> SEQUENCE: 144

Leu Met Ile Tyr Asp Val Ser Asn Arg Pro Ser
1               5                   10

<210> SEQ ID NO 145
<211> LENGTH: 11
<212> TYPE: PRT
<213> ORGANISM: Homo sapiens

<400> SEQUENCE: 145

Leu Val Ile Tyr Glu Asp Ser Asp Arg Pro Ser
1               5                   10

<210> SEQ ID NO 146
<211> LENGTH: 11
<212> TYPE: PRT
<213> ORGANISM: Homo sapiens

<400> SEQUENCE: 146

Val Met Ile Tyr Ser Val Ser Lys Arg Pro Ser
1               5                   10

<210> SEQ ID NO 147
<211> LENGTH: 10
<212> TYPE: PRT
<213> ORGANISM: Homo sapiens

<400> SEQUENCE: 147

Leu Leu Ile Tyr Asn Asn Gln Arg Pro Ser
1               5                   10

<210> SEQ ID NO 148
<211> LENGTH: 11
<212> TYPE: PRT
<213> ORGANISM: Homo sapiens

<400> SEQUENCE: 148

Leu Met Ile Tyr Arg Val Asp Asn Arg Pro Ser
1               5                   10

<210> SEQ ID NO 149
<211> LENGTH: 11
<212> TYPE: PRT
<213> ORGANISM: Homo sapiens

<400> SEQUENCE: 149

Leu Leu Ile Tyr Ser Asn Ser Gln Arg Pro Ser
1               5                   10

<210> SEQ ID NO 150
<211> LENGTH: 11
<212> TYPE: PRT
<213> ORGANISM: Homo sapiens
```

```
<400> SEQUENCE: 150

Leu Val Ile Tyr Ser Lys Asp Asn Arg Pro Ser
1               5                   10

<210> SEQ ID NO 151
<211> LENGTH: 11
<212> TYPE: PRT
<213> ORGANISM: Homo sapiens

<400> SEQUENCE: 151

Leu Val Ile Tyr Tyr Asp Asn Asp Arg Pro Ser
1               5                   10

<210> SEQ ID NO 152
<211> LENGTH: 11
<212> TYPE: PRT
<213> ORGANISM: Homo sapiens

<400> SEQUENCE: 152

Leu Met Ile Tyr Ser Val Asn Asn Arg Pro Ser
1               5                   10

<210> SEQ ID NO 153
<211> LENGTH: 11
<212> TYPE: PRT
<213> ORGANISM: Homo sapiens

<400> SEQUENCE: 153

Leu Met Ile Tyr Ser Val Ile Ser Arg Pro Ser
1               5                   10

<210> SEQ ID NO 154
<211> LENGTH: 11
<212> TYPE: PRT
<213> ORGANISM: Homo sapiens

<400> SEQUENCE: 154

Leu Leu Ile Tyr Asp Val Asn Lys Arg Pro Ser
1               5                   10

<210> SEQ ID NO 155
<211> LENGTH: 11
<212> TYPE: PRT
<213> ORGANISM: Homo sapiens

<400> SEQUENCE: 155

Leu Leu Ile Tyr Gly Asn Asn Lys Arg Pro Ser
1               5                   10

<210> SEQ ID NO 156
<211> LENGTH: 11
<212> TYPE: PRT
<213> ORGANISM: Homo sapiens

<400> SEQUENCE: 156

Leu Met Ile Tyr Asn Val Asn Lys Arg Pro Ser
1               5                   10

<210> SEQ ID NO 157
<211> LENGTH: 11
<212> TYPE: PRT
<213> ORGANISM: Homo sapiens

<400> SEQUENCE: 157
```

Leu Leu Ile Tyr Lys Asn Thr Asn Arg Pro Ser
1               5                   10

<210> SEQ ID NO 158
<211> LENGTH: 11
<212> TYPE: PRT
<213> ORGANISM: Homo sapiens

<400> SEQUENCE: 158

Leu Met Ile Tyr Asn Val Asn Asn Arg Pro Ser
1               5                   10

<210> SEQ ID NO 159
<211> LENGTH: 11
<212> TYPE: PRT
<213> ORGANISM: Homo sapiens

<400> SEQUENCE: 159

Val Met Ile Tyr Gly Val Thr Lys Arg Pro Ser
1               5                   10

<210> SEQ ID NO 160
<211> LENGTH: 8
<212> TYPE: PRT
<213> ORGANISM: Homo sapiens

<400> SEQUENCE: 160

Gln Gln Tyr Tyr Asp Phe Pro Pro
1               5

<210> SEQ ID NO 161
<211> LENGTH: 9
<212> TYPE: PRT
<213> ORGANISM: Homo sapiens

<400> SEQUENCE: 161

Gln Gln Tyr Ser His Asp Pro Ser Gly
1               5

<210> SEQ ID NO 162
<211> LENGTH: 8
<212> TYPE: PRT
<213> ORGANISM: Homo sapiens

<400> SEQUENCE: 162

Gln Gln Phe Tyr Ser Lys Pro Ile
1               5

<210> SEQ ID NO 163
<211> LENGTH: 9
<212> TYPE: PRT
<213> ORGANISM: Homo sapiens

<400> SEQUENCE: 163

Gln Gln Tyr Ser Gln Asp Pro Ser Ser
1               5

<210> SEQ ID NO 164
<211> LENGTH: 9
<212> TYPE: PRT
<213> ORGANISM: Homo sapiens

<400> SEQUENCE: 164

Gln Gln Trp Ser Leu Arg Ser Pro Phe

```
1               5

<210> SEQ ID NO 165
<211> LENGTH: 9
<212> TYPE: PRT
<213> ORGANISM: Homo sapiens

<400> SEQUENCE: 165

Ser Thr Tyr Asp Arg Arg Thr Phe Ser
1               5

<210> SEQ ID NO 166
<211> LENGTH: 10
<212> TYPE: PRT
<213> ORGANISM: Homo sapiens

<400> SEQUENCE: 166

Ser Ser Trp Asp Arg Ala Asp Gly Ser Tyr
1               5                   10

<210> SEQ ID NO 167
<211> LENGTH: 10
<212> TYPE: PRT
<213> ORGANISM: Homo sapiens

<400> SEQUENCE: 167

Gly Ala Trp Ala His Met Ser Leu Gly Lys
1               5                   10

<210> SEQ ID NO 168
<211> LENGTH: 10
<212> TYPE: PRT
<213> ORGANISM: Homo sapiens

<400> SEQUENCE: 168

Ala Thr Trp Asp His Ser Gln Met Gly Lys
1               5                   10

<210> SEQ ID NO 169
<211> LENGTH: 10
<212> TYPE: PRT
<213> ORGANISM: Homo sapiens

<400> SEQUENCE: 169

Ser Ser Tyr Asp Ile Glu Ser Ala Thr Pro
1               5                   10

<210> SEQ ID NO 170
<211> LENGTH: 8
<212> TYPE: PRT
<213> ORGANISM: Homo sapiens

<400> SEQUENCE: 170

Gln Gln Tyr Tyr Asn Phe Ser Phe
1               5

<210> SEQ ID NO 171
<211> LENGTH: 8
<212> TYPE: PRT
<213> ORGANISM: Homo sapiens

<400> SEQUENCE: 171

Gln Gln Arg Ser Asn Met Pro Ile
1               5
```

-continued

<210> SEQ ID NO 172
<211> LENGTH: 8
<212> TYPE: PRT
<213> ORGANISM: Homo sapiens

<400> SEQUENCE: 172

Ala Ser Arg Asp Ser Ser Ser Met
1               5

<210> SEQ ID NO 173
<211> LENGTH: 8
<212> TYPE: PRT
<213> ORGANISM: Homo sapiens

<400> SEQUENCE: 173

Gln Gln Tyr Tyr Asp Ser Ser Ser
1               5

<210> SEQ ID NO 174
<211> LENGTH: 10
<212> TYPE: PRT
<213> ORGANISM: Homo sapiens

<400> SEQUENCE: 174

Gln Ser Tyr Asp Phe Phe Thr Asn Ser Ser
1               5                   10

<210> SEQ ID NO 175
<211> LENGTH: 8
<212> TYPE: PRT
<213> ORGANISM: Homo sapiens

<400> SEQUENCE: 175

Gln Gln Tyr Gly Ser Phe Pro Ala
1               5

<210> SEQ ID NO 176
<211> LENGTH: 10
<212> TYPE: PRT
<213> ORGANISM: Homo sapiens

<400> SEQUENCE: 176

Gln Ser Trp Asp Ala Pro Met Gly Met Trp
1               5                   10

<210> SEQ ID NO 177
<211> LENGTH: 8
<212> TYPE: PRT
<213> ORGANISM: Homo sapiens

<400> SEQUENCE: 177

Gln Gln Tyr Tyr Ser Tyr Ser Val
1               5

<210> SEQ ID NO 178
<211> LENGTH: 9
<212> TYPE: PRT
<213> ORGANISM: Homo sapiens

<400> SEQUENCE: 178

Gly Ala Tyr Thr Thr Asp Thr Leu Ser
1               5

<210> SEQ ID NO 179

```
<211> LENGTH: 8
<212> TYPE: PRT
<213> ORGANISM: Homo sapiens

<400> SEQUENCE: 179

Gln Gln Tyr Ser Asp Ile Pro Ala
1               5

<210> SEQ ID NO 180
<211> LENGTH: 8
<212> TYPE: PRT
<213> ORGANISM: Homo sapiens

<400> SEQUENCE: 180

Leu Gln Val Tyr Asn Leu Pro Leu
1               5

<210> SEQ ID NO 181
<211> LENGTH: 10
<212> TYPE: PRT
<213> ORGANISM: Homo sapiens

<400> SEQUENCE: 181

Ser Thr Tyr Asp Asp Gln Gln Asp Ala
1               5                   10

<210> SEQ ID NO 182
<211> LENGTH: 10
<212> TYPE: PRT
<213> ORGANISM: Homo sapiens

<400> SEQUENCE: 182

Gln Ser Tyr Asp Lys Pro Thr Phe Ser Gly
1               5                   10

<210> SEQ ID NO 183
<211> LENGTH: 10
<212> TYPE: PRT
<213> ORGANISM: Homo sapiens

<400> SEQUENCE: 183

Ser Ala Tyr Asp Thr Asn Asn Tyr Leu Ser
1               5                   10

<210> SEQ ID NO 184
<211> LENGTH: 7
<212> TYPE: PRT
<213> ORGANISM: Homo sapiens

<400> SEQUENCE: 184

Gln Ala Tyr Ala Ser Asn Ile
1               5

<210> SEQ ID NO 185
<211> LENGTH: 8
<212> TYPE: PRT
<213> ORGANISM: Homo sapiens

<400> SEQUENCE: 185

Gln Ser Trp Val Gly Pro Ser Thr
1               5

<210> SEQ ID NO 186
<211> LENGTH: 9
<212> TYPE: PRT
```

<213> ORGANISM: Homo sapiens

<400> SEQUENCE: 186

Gln Ser Tyr Asp His Asn Ser Tyr Thr
1               5

<210> SEQ ID NO 187
<211> LENGTH: 8
<212> TYPE: PRT
<213> ORGANISM: Homo sapiens

<400> SEQUENCE: 187

Ser Ser Trp Ala His Asp His Lys
1               5

<210> SEQ ID NO 188
<211> LENGTH: 10
<212> TYPE: PRT
<213> ORGANISM: Homo sapiens

<400> SEQUENCE: 188

Gln Ser Tyr Asp Gly Gln Met Ser Thr Ser
1               5                   10

<210> SEQ ID NO 189
<211> LENGTH: 10
<212> TYPE: PRT
<213> ORGANISM: Homo sapiens

<400> SEQUENCE: 189

Ser Thr Tyr Asp His Thr Ser Ser Gly Phe
1               5                   10

<210> SEQ ID NO 190
<211> LENGTH: 8
<212> TYPE: PRT
<213> ORGANISM: Homo sapiens

<400> SEQUENCE: 190

Ala Ser Phe Thr Phe Pro Ser Leu
1               5

<210> SEQ ID NO 191
<211> LENGTH: 10
<212> TYPE: PRT
<213> ORGANISM: Homo sapiens

<400> SEQUENCE: 191

Ala Ser Trp Asp Ser Val Gln Val Ser Pro
1               5                   10

<210> SEQ ID NO 192
<211> LENGTH: 9
<212> TYPE: PRT
<213> ORGANISM: Homo sapiens

<400> SEQUENCE: 192

Ser Ala Trp Asp Leu Leu Glu Val Tyr
1               5

<210> SEQ ID NO 193
<211> LENGTH: 8
<212> TYPE: PRT
<213> ORGANISM: Homo sapiens -continued

<400> SEQUENCE: 193

Ser Ala Tyr Ala Pro Ser Ala Val
1               5

<210> SEQ ID NO 194
<211> LENGTH: 10
<212> TYPE: PRT
<213> ORGANISM: Homo sapiens

<400> SEQUENCE: 194

Ser Ser Tyr Asp Ser Phe His His Gly Ile
1               5                   10

<210> SEQ ID NO 195
<211> LENGTH: 10
<212> TYPE: PRT
<213> ORGANISM: Homo sapiens

<400> SEQUENCE: 195

Ser Ser Tyr Asp Tyr Val Ser Ser Asp Thr
1               5                   10

<210> SEQ ID NO 196
<211> LENGTH: 10
<212> TYPE: PRT
<213> ORGANISM: Homo sapiens

<400> SEQUENCE: 196

Gln Thr Tyr Asp Glu His Gly Phe His Ile
1               5                   10

<210> SEQ ID NO 197
<211> LENGTH: 10
<212> TYPE: PRT
<213> ORGANISM: Homo sapiens

<400> SEQUENCE: 197

Ser Thr Tyr Thr Gly Leu Pro Phe Thr Thr
1               5                   10

<210> SEQ ID NO 198
<211> LENGTH: 121
<212> TYPE: PRT
<213> ORGANISM: Homo sapiens

<400> SEQUENCE: 198

Gln Val Glu Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Val Ile Met Pro Ser Asp Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Gly His Gly Met Tyr Gly Gly Ala Leu Asp Val Trp Gly
            100                 105                 110

Gln Gly Thr Leu Val Thr Val Ser Ser

```
                          115                 120

<210> SEQ ID NO 199
<211> LENGTH: 121
<212> TYPE: PRT
<213> ORGANISM: Homo sapiens

<400> SEQUENCE: 199

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Phe Ile Trp Pro Val Asp Ser Trp Thr Gln Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Gly His Gly Met Tyr Gly Gly Ala Leu Asp Val Trp Gly
            100                 105                 110

Gln Gly Thr Leu Val Thr Val Ser Ser
            115                 120

<210> SEQ ID NO 200
<211> LENGTH: 121
<212> TYPE: PRT
<213> ORGANISM: Homo sapiens

<400> SEQUENCE: 200

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Phe Ile Trp Pro Val Asp Ser Trp Thr Gln Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Gly His Gly Met Tyr Gly Gly Ala Leu Asp Val Trp Gly
            100                 105                 110

Gln Gly Thr Leu Val Thr Val Ser Ser
            115                 120

<210> SEQ ID NO 201
<211> LENGTH: 121
<212> TYPE: PRT
<213> ORGANISM: Homo sapiens

<400> SEQUENCE: 201

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30
```

Trp Ile Gly Trp Val Arg Gln Met Pro Gly Lys Gly Leu Glu Trp Met
            35                  40                  45

Gly Ile Ile Trp Pro Ile Asp Ser Phe Thr Gln Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Gly His Gly Met Tyr Gly Gly Ala Leu Asp Val Trp Gly
                100                 105                 110

Gln Gly Thr Leu Val Thr Val Ser Ser
            115                 120

<210> SEQ ID NO 202
<211> LENGTH: 121
<212> TYPE: PRT
<213> ORGANISM: Homo sapiens

<400> SEQUENCE: 202

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
            35                  40                  45

Gly Val Ile Met Pro Ser Asp Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Gly His Gly Met Tyr Gly Gly Ala Leu Asp Val Trp Gly
                100                 105                 110

Gln Gly Thr Leu Val Thr Val Ser Ser
            115                 120

<210> SEQ ID NO 203
<211> LENGTH: 121
<212> TYPE: PRT
<213> ORGANISM: Homo sapiens

<400> SEQUENCE: 203

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
            35                  40                  45

Gly Val Ile Met Pro Ser Asp Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Gly His Gly Met Tyr Gly Gly Ala Leu Asp Val Trp Gly
                100                 105                 110

```
Gln Gly Thr Leu Val Thr Val Ser Ser
        115                 120

<210> SEQ ID NO 204
<211> LENGTH: 121
<212> TYPE: PRT
<213> ORGANISM: Homo sapiens

<400> SEQUENCE: 204

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Val Ile Met Pro Ser Asp Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Gly His Gly Met Tyr Gly Gly Ala Leu Asp Val Trp Gly
            100                 105                 110

Gln Gly Thr Leu Val Thr Val Ser Ser
        115                 120

<210> SEQ ID NO 205
<211> LENGTH: 121
<212> TYPE: PRT
<213> ORGANISM: Homo sapiens

<400> SEQUENCE: 205

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Ala Ile Met Tyr Asp Ser Ser Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Tyr Ile Tyr Lys Gly Val His Phe Asp Tyr Trp Gly
            100                 105                 110

Gln Gly Thr Leu Val Thr Val Ser Ser
        115                 120

<210> SEQ ID NO 206
<211> LENGTH: 119
<212> TYPE: PRT
<213> ORGANISM: Homo sapiens

<400> SEQUENCE: 206

Gln Val Glu Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Gly Asn
            20                  25                  30

Tyr Ile Asn Trp Val Arg Gln Ala Pro Gly Gln Gly Leu Glu Trp Met
        35                  40                  45

Gly Ile Ile Asn Pro His Gly Gly Asp Thr Lys Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp His His Gly Thr Trp Ile Phe Asp Tyr Trp Gly Gln Gly
            100                 105                 110

Thr Leu Val Thr Val Ser Ser
            115

<210> SEQ ID NO 207
<211> LENGTH: 119
<212> TYPE: PRT
<213> ORGANISM: Homo sapiens

<400> SEQUENCE: 207

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Asn
            20                  25                  30

Tyr Ile Asn Trp Val Arg Gln Ala Pro Gly Gln Gly Leu Glu Trp Met
        35                  40                  45

Gly Ile Ile Asn Pro Thr Lys Gly Trp Thr Leu Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp His His Gly Thr Trp Ile Phe Asp Tyr Trp Gly Gln Gly
            100                 105                 110

Thr Leu Val Thr Val Ser Ser
            115

<210> SEQ ID NO 208
<211> LENGTH: 121
<212> TYPE: PRT
<213> ORGANISM: Homo sapiens

<400> SEQUENCE: 208

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Phe Ile Trp Pro Ser Asp Ser Trp Thr Ser Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Gly His Gly Met Tyr Gly Ala Leu Asp Val Trp Gly
            100                 105                 110
Gln Gly Thr Leu Val Thr Val Ser Ser
        115                 120

<210> SEQ ID NO 209
<211> LENGTH: 119
<212> TYPE: PRT
<213> ORGANISM: Homo sapiens

<400> SEQUENCE: 209

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Asn
            20                  25                  30

Tyr Ile Asn Trp Val Arg Gln Ala Pro Gly Gln Gly Leu Glu Trp Met
        35                  40                  45

Gly Ile Ile Asn Pro His Gly Gly Asp Thr Lys Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp His His Gly Thr Trp Ile Phe Asp Tyr Trp Gly Gln Gly
            100                 105                 110

Thr Leu Val Thr Val Ser Ser
        115

<210> SEQ ID NO 210
<211> LENGTH: 115
<212> TYPE: PRT
<213> ORGANISM: Homo sapiens

<400> SEQUENCE: 210

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Tyr Phe Ser Trp Val Arg Gln Ala Pro Gly Gln Gly Leu Glu Trp Met
        35                  40                  45

Gly Gly Ile Ile Pro Lys Phe Gly Ser Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Thr Ser Met Asp Tyr Trp Gly Gln Gly Thr Leu Val Thr
            100                 105                 110

Val Ser Ser
        115

<210> SEQ ID NO 211
<211> LENGTH: 115
<212> TYPE: PRT
<213> ORGANISM: Homo sapiens

<400> SEQUENCE: 211

Gln Val Gln Leu Val Gln Ser Gly Ala Glu Val Lys Lys Pro Gly Ser

```
            1               5                  10                 15
          Ser Val Lys Val Ser Cys Lys Ala Ser Gly Gly Thr Phe Ser Ser Tyr
                        20                  25                  30

Tyr Phe Ser Trp Val Arg Gln Ala Pro Gly Gln Gly Leu Glu Trp Met
                        35                  40                  45

Gly Gly Ile Ile Pro Lys Phe Gly Ser Ala Asn Tyr Ala Gln Lys Phe
                        50                  55                  60

Gln Gly Arg Val Thr Ile Thr Ala Asp Glu Ser Thr Ser Thr Ala Tyr
          65                  70                  75                  80

Met Glu Leu Ser Ser Leu Arg Ser Glu Asp Thr Ala Val Tyr Tyr Cys
                        85                  90                  95

Ala Arg Arg Thr Ser Met Asp Tyr Trp Gly Gln Gly Thr Leu Val Thr
                        100                 105                 110

Val Ser Ser
                        115

<210> SEQ ID NO 212
<211> LENGTH: 120
<212> TYPE: PRT
<213> ORGANISM: Homo sapiens

<400> SEQUENCE: 212

Gln Val Glu Leu Val Gln Ser Gly Ala Glu Val Lys Lys Pro Gly Glu
          1               5                  10                 15

Ser Leu Lys Ile Ser Cys Lys Gly Ser Gly Tyr Ser Phe Thr Ser Tyr
                        20                  25                  30

Trp Ile Gly Trp Val Arg Gln Ala Pro Gly Lys Gly Leu Glu Trp Met
                        35                  40                  45

Gly Ile Ile Asp Pro Gly Asp Ser Arg Thr Arg Tyr Ser Pro Ser Phe
                        50                  55                  60

Gln Gly Gln Val Thr Ile Ser Ala Asp Lys Ser Ile Ser Thr Ala Tyr
          65                  70                  75                  80

Leu Gln Trp Ser Ser Leu Lys Ala Ser Asp Thr Ala Met Tyr Tyr Cys
                        85                  90                  95

Ala Arg Gly Gln Leu Tyr Gly Gly Thr Tyr Met Asp Tyr Trp Gly Gln
                        100                 105                 110

Gly Thr Leu Val Thr Val Ser Ser
                        115                 120

<210> SEQ ID NO 213
<211> LENGTH: 121
<212> TYPE: PRT
<213> ORGANISM: Homo sapiens

<400> SEQUENCE: 213

Gln Val Gln Leu Val Glu Ser Gly Gly Gly Leu Val Gln Pro Gly Gly
          1               5                  10                 15

Ser Leu Arg Leu Ser Cys Ala Ala Ser Gly Phe Thr Phe Ser Asp Tyr
                        20                  25                  30

Ala Met Ser Trp Val Arg Gln Ala Pro Gly Lys Gly Leu Glu Trp Val
                        35                  40                  45

Ser Ala Ile Met Tyr Asp Ser Ser Thr Phe Tyr Ala Asp Ser Val
                        50                  55                  60

Lys Gly Arg Phe Thr Ile Ser Arg Asp Asn Ser Lys Asn Thr Leu Tyr
          65                  70                  75                  80

Leu Gln Met Asn Ser Leu Arg Ala Glu Asp Thr Ala Val Tyr Tyr Cys
```

```
                        85                  90                  95
Ala Arg Ile Asn Tyr Ile Tyr Lys Gly Val His Phe Asp Tyr Trp Gly
                100                 105                 110

Gln Gly Thr Leu Val Thr Val Ser Ser
            115                 120
```

<210> SEQ ID NO 214
<211> LENGTH: 116
<212> TYPE: PRT
<213> ORGANISM: Homo sapiens

<400> SEQUENCE: 214

```
Gln Val Gln Leu Gln Glu Ser Gly Pro Gly Leu Val Lys Pro Gly Glu
1               5                   10                  15

Thr Leu Ser Leu Thr Cys Thr Val Ser Gly Gly Ser Ile Ser Asn Tyr
            20                  25                  30

Tyr Trp Ser Trp Ile Arg Gln Ala Pro Gly Lys Gly Leu Glu Trp Ile
        35                  40                  45

Gly Glu Ile Tyr His Ser Gly Thr Tyr Tyr Asn Pro Ser Leu Lys
    50                  55                  60

Gly Arg Val Thr Ile Ser Val Asp Thr Ser Lys Asn Gln Phe Ser Leu
65                  70                  75                  80

Lys Leu Ser Ser Val Thr Ala Glu Asp Thr Ala Val Tyr Tyr Cys Ala
                85                  90                  95

Arg Pro Met Asp Asn Leu Pro Asp Ile Trp Gly Gln Gly Thr Leu Val
                100                 105                 110

Thr Val Ser Ser
        115
```

<210> SEQ ID NO 215
<211> LENGTH: 116
<212> TYPE: PRT
<213> ORGANISM: Homo sapiens

<400> SEQUENCE: 215

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ser Gly Ile Ser Tyr Ser Ser Ala Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Leu Tyr Tyr Phe Asp Val Trp Gly Gln Gly Thr Leu Val
                100                 105                 110

Thr Val Ser Ser
        115
```

<210> SEQ ID NO 216
<211> LENGTH: 115
<212> TYPE: PRT
<213> ORGANISM: Homo sapiens

<400> SEQUENCE: 216

```
Gln Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Asn Ser
            20                  25                  30

Trp Met Ser Trp Val Arg Gln Ala Pro Gly Lys Gly Leu Glu Trp Val
        35                  40                  45

Ser Ala Ile Thr Tyr Trp Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Lys Phe Phe Ala Asn Trp Gly Gln Gly Thr Leu Val Thr
                100                 105                 110

Val Ser Ser
        115

<210> SEQ ID NO 217
<211> LENGTH: 115
<212> TYPE: PRT
<213> ORGANISM: Homo sapiens

<400> SEQUENCE: 217

Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Asn Tyr
            20                  25                  30

Ser Ile Ser Trp Val Arg Gln Ala Pro Gly Gln Gly Leu Glu Trp Met
        35                  40                  45

Gly Arg Ile Ile Pro Asn Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ile Tyr Phe Ala Phe Trp Gly Gln Gly Thr Leu Val Thr
                100                 105                 110

Val Ser Ser
        115

<210> SEQ ID NO 218
<211> LENGTH: 120
<212> TYPE: PRT
<213> ORGANISM: Homo sapiens

<400> SEQUENCE: 218

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Leu His Trp Val Arg Gln Ala Pro Gly Gln Gly Leu Glu Trp Met
        35                  40                  45

Gly Ile Ile Asn Pro Gln Asn Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80
```

Met Glu Leu Ser Ser Leu Arg Ser Glu Asp Thr Ala Val Tyr Tyr Cys
             85                  90                  95

Ala Arg Lys His Lys Tyr Arg Ile Gly Ser Met Asp Val Trp Gly Gln
            100                 105                 110

Gly Thr Leu Val Thr Val Ser Ser
        115                 120

<210> SEQ ID NO 219
<211> LENGTH: 117
<212> TYPE: PRT
<213> ORGANISM: Homo sapiens

<400> SEQUENCE: 219

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Ile Ile Asp Pro Arg Glu Ser Phe Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Met Lys Gly Gly Tyr Asp Tyr Trp Gly Gln Gly Thr Leu
            100                 105                 110

Val Thr Val Ser Ser
        115

<210> SEQ ID NO 220
<211> LENGTH: 120
<212> TYPE: PRT
<213> ORGANISM: Homo sapiens

<400> SEQUENCE: 220

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Arg
            20                  25                  30

Ser Ala Ala Trp Gly Trp Ile Arg Gln Ser Pro Gly Arg Gly Leu Glu
        35                  40                  45

Trp Leu Gly Arg Ile Gly Tyr Arg Ser Lys Trp Met Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Met Gln Gly Phe Gln Leu Asp Tyr Trp Gly Gln
            100                 105                 110

Gly Thr Leu Val Thr Val Ser Ser
        115                 120

<210> SEQ ID NO 221
<211> LENGTH: 115
<212> TYPE: PRT
<213> ORGANISM: Homo sapiens

<400> SEQUENCE: 221

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ser Leu His Trp Val Arg Gln Ala Pro Gly Gln Gly Leu Glu Trp Met
        35                  40                  45

Gly Gly Ile Val Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Tyr Thr Phe Ala Val Trp Gly Gln Gly Thr Leu Val Thr
            100                 105                 110

Val Ser Ser
        115

<210> SEQ ID NO 222
<211> LENGTH: 116
<212> TYPE: PRT
<213> ORGANISM: Homo sapiens

<400> SEQUENCE: 222

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Gly Ile Ser Gly Asn Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Lys Trp Leu Phe Tyr Asp Tyr Trp Gly Gln Gly Thr Leu Val
            100                 105                 110

Thr Val Ser Ser
        115

<210> SEQ ID NO 223
<211> LENGTH: 114
<212> TYPE: PRT
<213> ORGANISM: Homo sapiens

<400> SEQUENCE: 223

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ile Tyr
            20                  25                  30

Asp Met His Trp Val Arg Gln Ala Pro Gly Gln Gly Leu Glu Trp Met
        35                  40                  45

Gly Tyr Ile Ser Pro Tyr Ser Gly Asp Thr Asn Tyr Ala Gln Lys Phe
    50                  55                  60

```
Gln Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Trp Gln Asp Phe Trp Gly Gln Gly Thr Leu Val Thr Val
            100                 105                 110

Ser Ser
```

<210> SEQ ID NO 224
<211> LENGTH: 126
<212> TYPE: PRT
<213> ORGANISM: Homo sapiens

<400> SEQUENCE: 224

```
Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
             20                  25                  30

Ser Ala Ala Trp Gly Trp Ile Arg Gln Ser Pro Gly Arg Gly Leu Glu
         35                  40                  45

Trp Leu Gly Arg Ile Ser Tyr Arg Ser Arg Trp Tyr Asn Asn Tyr Ala
 50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
             85                  90                  95

Tyr Tyr Cys Ala Arg Tyr Tyr Ser Asp His Phe Gly Leu Tyr Pro Tyr
            100                 105                 110

Phe Asp Tyr Trp Gly Gln Gly Thr Leu Val Thr Val Ser Ser
        115                 120                 125
```

<210> SEQ ID NO 225
<211> LENGTH: 126
<212> TYPE: PRT
<213> ORGANISM: Homo sapiens

<400> SEQUENCE: 225

```
Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Asn Thr Ser
             20                  25                  30

Trp Ile Trp Val Arg Gln Met Pro Gly Lys Gly Leu Glu Trp Met Gly
         35                  40                  45

Ile Ile His Pro Gly His Ser Tyr Thr Arg Tyr Ser Pro Ser Phe Gln
 50                  55                  60

Gly Gln Val Thr Ile Ser Ala Asp Lys Ser Ile Ser Thr Ala Tyr Leu
 65                  70                  75                  80

Gln Trp Ser Ser Leu Lys Ala Ser Asp Thr Ala Met Tyr Tyr Cys Ala
             85                  90                  95

Arg Gly Asp Gly Gly Pro Ser Ser Gln Gly Asn Tyr Phe Gly Trp Val
            100                 105                 110

Tyr Asp Val Trp Gly Gln Gly Thr Leu Val Thr Val Ser Ser
        115                 120                 125
```

<210> SEQ ID NO 226
<211> LENGTH: 125
<212> TYPE: PRT

```
<213> ORGANISM: Homo sapiens

<400> SEQUENCE: 226

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Ser Trp Ile Arg Gln Ser Pro Gly Arg Gly Leu Glu
        35                  40                  45

Trp Leu Gly Arg Ile Tyr Tyr Arg Ser Lys Lys Trp Tyr Asn Asp Tyr
    50                  55                  60

Ala Val Ser Val Lys Ser Arg Ile Thr Ile Asn Pro Asp Thr Ser Lys
65                  70                  75                  80

Asn Gln Phe Ser Leu Gln Leu Asn Ser Val Thr Pro Glu Asp Thr Ala
                85                  90                  95

Val Tyr Tyr Cys Ala Arg Asn Tyr Ser Gly Pro Met Tyr Tyr Tyr Gly
            100                 105                 110

Asp Val Trp Gly Gln Gly Thr Leu Val Thr Val Ser Ser
            115                 120                 125

<210> SEQ ID NO 227
<211> LENGTH: 123
<212> TYPE: PRT
<213> ORGANISM: Homo sapiens

<400> SEQUENCE: 227

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Ser Trp Ile Arg Gln Ser Pro Gly Arg Gly Leu Glu
        35                  40                  45

Trp Leu Gly Arg Ile Gln Tyr Arg Ser Lys Trp Tyr Asn Ala Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Phe His Gly Ser Thr Met Tyr Phe Asp Val
            100                 105                 110

Trp Gly Gln Gly Thr Leu Val Thr Val Ser Ser
            115                 120

<210> SEQ ID NO 228
<211> LENGTH: 117
<212> TYPE: PRT
<213> ORGANISM: Homo sapiens

<400> SEQUENCE: 228

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Thr Tyr
            20                  25                  30

Trp Ile Gly Trp Val Arg Gln Ala Pro Gly Lys Gly Leu Glu Trp Met
        35                  40                  45

Gly Phe Ile Tyr Pro Asp Lys Ser Tyr Thr Asn Tyr Ser Pro Ser Phe
    50                  55                  60
```

```
Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gly Leu Gly Gly Ser Phe Asp Val Trp Gly Gln Gly Thr Leu
            100                 105                 110

Val Thr Val Ser Ser
            115

<210> SEQ ID NO 229
<211> LENGTH: 123
<212> TYPE: PRT
<213> ORGANISM: Homo sapiens

<400> SEQUENCE: 229

Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asn
             20                  25                  30

Ser Ala Ser Trp Ser Trp Ile Arg Gln Ser Pro Gly Arg Gly Leu Glu
         35                  40                  45

Trp Leu Gly Arg Ile Tyr Tyr Arg Ser Gln Trp Tyr Asn Asp Tyr Ala
 50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Gly Trp Ile Thr Gly Trp Arg Ile Phe Asp Tyr
            100                 105                 110

Trp Gly Gln Gly Thr Leu Val Thr Val Ser Ser
            115                 120

<210> SEQ ID NO 230
<211> LENGTH: 120
<212> TYPE: PRT
<213> ORGANISM: Homo sapiens

<400> SEQUENCE: 230

Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Thr Tyr
             20                  25                  30

Ala Met Ser Trp Val Arg Gln Ala Pro Gly Lys Gly Leu Glu Trp Val
         35                  40                  45

Ser Phe Ile Ser Gly Tyr Gly Ser Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Lys Met Tyr Trp Trp Ser Asp Gly Phe Asp Tyr Trp Gly Gln
            100                 105                 110

Gly Thr Leu Val Thr Val Ser Ser
            115                 120

<210> SEQ ID NO 231
```

```
<211> LENGTH: 121
<212> TYPE: PRT
<213> ORGANISM: Homo sapiens

<400> SEQUENCE: 231

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Ile Ser Trp Val Arg Gln Ala Pro Gly Lys Gly Leu Glu Trp Val
        35                  40                  45

Ser Ser Ile Ser Gly Gly Gly Ser Lys Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Pro Gly Pro Thr Gly His Val Phe Phe Asp Ile Trp Gly
            100                 105                 110

Gln Gly Thr Leu Val Thr Val Ser Ser
        115                 120

<210> SEQ ID NO 232
<211> LENGTH: 116
<212> TYPE: PRT
<213> ORGANISM: Homo sapiens

<400> SEQUENCE: 232

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Tyr Ile Ser Trp Val Arg Gln Ala Pro Gly Gln Gly Leu Glu Trp Met
        35                  40                  45

Gly Gly Ile Ile Pro Lys Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Ile Gly Ile Tyr Asp Ser Trp Gly Gln Gly Thr Leu Val
            100                 105                 110

Thr Val Ser Ser
        115

<210> SEQ ID NO 233
<211> LENGTH: 115
<212> TYPE: PRT
<213> ORGANISM: Homo sapiens

<400> SEQUENCE: 233

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser His
            20                  25                  30

Ala Ile Ser Trp Val Arg Gln Ala Pro Gly Gln Gly Leu Glu Trp Met
        35                  40                  45
```

Gly Asn Ile Met Pro Ile Phe Gly Val Ala Asn Tyr Ala Gln Lys Phe
         50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Met Arg Leu Ala Tyr Trp Gly Gln Gly Thr Leu Val Thr
            100                 105                 110

Val Ser Ser
        115

<210> SEQ ID NO 234
<211> LENGTH: 126
<212> TYPE: PRT
<213> ORGANISM: Homo sapiens

<400> SEQUENCE: 234

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
             20                  25                  30

Thr Ala Ala Trp Ser Trp Ile Arg Gln Ser Pro Gly Arg Gly Leu Glu
         35                  40                  45

Trp Leu Gly Arg Ile Arg Tyr Arg Ser Lys Trp Tyr Asn Asp Tyr Ala
 50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Gly Tyr His Gln Gly Leu Tyr Gly Asn His Met
            100                 105                 110

Phe Asp Val Trp Gly Gln Gly Thr Leu Val Thr Val Ser Ser
            115                 120                 125

<210> SEQ ID NO 235
<211> LENGTH: 118
<212> TYPE: PRT
<213> ORGANISM: Homo sapiens

<400> SEQUENCE: 235

Gln Val Gln Leu Lys Glu Ser Gly Pro Ala Leu Val Lys Pro Thr Gln
 1               5                  10                  15

Thr Leu Thr Leu Thr Cys Thr Phe Ser Gly Phe Ser Leu Ser Ser Ser
             20                  25                  30

Gly Val Gly Val Ser Trp Ile Arg Gln Pro Pro Gly Lys Ala Leu Glu
         35                  40                  45

Trp Leu Ala Leu Ile Asp Trp Asp Asp Lys Ser Tyr Ser Thr Ser
 50                  55                  60

Leu Lys Thr Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Ile Gln Gly Trp Asn Tyr Asp Val Trp Gly Gln Gly Thr
            100                 105                 110

Leu Val Thr Val Ser Ser
        115

<210> SEQ ID NO 236
<211> LENGTH: 120
<212> TYPE: PRT
<213> ORGANISM: Homo sapiens

<400> SEQUENCE: 236

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Ser
            20                  25                  30

Ser Ala Ala Trp Ser Trp Ile Arg Gln Ser Pro Gly Arg Gly Leu Glu
        35                  40                  45

Trp Leu Gly Arg Ile Gly Gln Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Ser Arg Phe Gly Tyr Phe Asp Val Trp Gly Gln
            100                 105                 110

Gly Thr Leu Val Thr Val Ser Ser
        115                 120
```

<210> SEQ ID NO 237
<211> LENGTH: 118
<212> TYPE: PRT
<213> ORGANISM: Homo sapiens

<400> SEQUENCE: 237

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Tyr Ser Trp Val Arg Gln Ala Pro Gly Lys Gly Leu Glu Trp Val Ser
        35                  40                  45

Thr Ile Ser Ser Asn Gly Ser Tyr Thr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Phe Val Ala Arg Leu Asn Val Phe Asp Tyr Trp Gly Gln Gly Thr
            100                 105                 110

Leu Val Thr Val Ser Ser
        115
```

<210> SEQ ID NO 238
<211> LENGTH: 115
<212> TYPE: PRT
<213> ORGANISM: Homo sapiens

<400> SEQUENCE: 238

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Thr Ile Ser Trp Val Arg Gln Ala Pro Gly Gln Gly Leu Glu Trp Met
```

```
                35                  40                  45
Gly Asn Ile Ile Pro Ala Phe Gly Tyr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Lys Phe Thr Phe Asp Val Trp Gly Gln Gly Thr Leu Val Thr
                100                 105                 110

Val Ser Ser
        115

<210> SEQ ID NO 239
<211> LENGTH: 118
<212> TYPE: PRT
<213> ORGANISM: Homo sapiens

<400> SEQUENCE: 239

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Tyr Ser Trp Val Arg Gln Ala Pro Gly Lys Gly Leu Glu Trp Val Ser
        35                  40                  45

Asn Ile Ser Gly Asn Gly Ser Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Leu Ile Ala Thr Leu Gly Thr Phe Asp Tyr Trp Gly Gln Gly Thr
                100                 105                 110

Leu Val Thr Val Ser Ser
        115

<210> SEQ ID NO 240
<211> LENGTH: 120
<212> TYPE: PRT
<213> ORGANISM: Homo sapiens

<400> SEQUENCE: 240

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30

Gly Ile His Trp Val Arg Gln Ala Pro Gly Lys Gly Leu Glu Trp Val
        35                  40                  45

Ser Tyr Ile Arg Ser Gly Ser Ser Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Ala Pro Ala Gly His Gly Val Phe Ala Asn Trp Gly Gln
                100                 105                 110

Gly Thr Leu Val Thr Val Ser Ser
```

```
                 115                 120

<210> SEQ ID NO 241
<211> LENGTH: 110
<212> TYPE: PRT
<213> ORGANISM: Homo sapiens

<400> SEQUENCE: 241

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Arg Leu Ala Trp Tyr Gln Gln Lys Pro Gly Gln Ala Pro Arg Leu Leu
        35                  40                  45

Ile Tyr Gly Ala Ser Lys Arg Ala Thr Gly Val Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Gln Gln Tyr Tyr Asp Phe Pro
                85                  90                  95

Pro Thr Phe Gly Gln Gly Thr Lys Val Glu Ile Lys Arg Thr
            100                 105                 110

<210> SEQ ID NO 242
<211> LENGTH: 111
<212> TYPE: PRT
<213> ORGANISM: Homo sapiens

<400> SEQUENCE: 242

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Arg Leu Ala Trp Tyr Gln Gln Lys Pro Gly Gln Ala Pro Arg Leu Leu
        35                  40                  45

Ile Tyr Gly Ala Ser Lys Arg Ala Thr Gly Val Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Ser His Asp Pro
                85                  90                  95

Ser Gly Thr Phe Gly Gln Gly Thr Lys Val Glu Ile Lys Arg Thr
            100                 105                 110

<210> SEQ ID NO 243
<211> LENGTH: 110
<212> TYPE: PRT
<213> ORGANISM: Homo sapiens

<400> SEQUENCE: 243

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Arg Leu Ala Trp Tyr Gln Gln Lys Pro Gly Gln Ala Pro Arg Leu Leu
        35                  40                  45

Ile Tyr Gly Ala Ser Lys Arg Ala Thr Gly Val Pro Ala Arg Phe Ser
50                  55                  60
```

```
Gly Ser Gly Ser Gly Thr Asp Phe Thr Leu Thr Ile Ser Ser Leu Glu
 65                  70                  75                  80

Pro Glu Asp Phe Ala Thr Tyr Tyr Cys Gln Gln Tyr Tyr Asp Phe Pro
                 85                  90                  95

Pro Thr Phe Gly Gln Gly Thr Lys Val Glu Ile Lys Arg Thr
            100                 105                 110

<210> SEQ ID NO 244
<211> LENGTH: 110
<212> TYPE: PRT
<213> ORGANISM: Homo sapiens

<400> SEQUENCE: 244

Asp Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Arg Ser Ser
                20                  25                  30

Arg Leu Ala Trp Tyr Gln Gln Lys Pro Gly Gln Ala Pro Arg Leu Leu
            35                  40                  45

Ile Tyr Gly Ala Ser Lys Arg Ala Thr Gly Val Pro Ala Arg Phe Ser
 50                  55                  60

Gly Ser Gly Ser Gly Thr Asp Phe Thr Leu Thr Ile Ser Ser Leu Glu
 65                  70                  75                  80

Pro Glu Asp Phe Ala Thr Tyr Tyr Cys Gln Gln Tyr Tyr Asp Phe Pro
                 85                  90                  95

Pro Thr Phe Gly Gln Gly Thr Lys Val Glu Ile Lys Arg Thr
            100                 105                 110

<210> SEQ ID NO 245
<211> LENGTH: 110
<212> TYPE: PRT
<213> ORGANISM: Homo sapiens

<400> SEQUENCE: 245

Asp Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Arg Ser Ser
                20                  25                  30

Arg Leu Ala Trp Tyr Gln Gln Lys Pro Gly Gln Ala Pro Arg Leu Leu
            35                  40                  45

Ile Tyr Gly Ala Ser Lys Arg Ala Thr Gly Val Pro Ala Arg Phe Ser
 50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Gln Gln Phe Tyr Ser Lys Pro
                 85                  90                  95

Ile Thr Phe Gly Gln Gly Thr Lys Val Glu Ile Lys Arg Thr
            100                 105                 110

<210> SEQ ID NO 246
<211> LENGTH: 111
<212> TYPE: PRT
<213> ORGANISM: Homo sapiens

<400> SEQUENCE: 246

Asp Ile Val Leu Thr Gln Ser Pro Ala Thr Leu Ser Leu Ser Pro Gly
 1               5                  10                  15
```

-continued

Glu Arg Ala Thr Leu Ser Cys Arg Ala Ser Gln Ser Val Arg Ser Ser
            20                  25                  30

Arg Leu Ala Trp Tyr Gln Gln Lys Pro Gly Gln Ala Pro Arg Leu Leu
        35                  40                  45

Ile Tyr Gly Ala Ser Lys Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Ser His Asp Pro
                85                  90                  95

Ser Gly Thr Phe Gly Gln Gly Thr Lys Val Glu Ile Lys Arg Thr
            100                 105                 110

<210> SEQ ID NO 247
<211> LENGTH: 111
<212> TYPE: PRT
<213> ORGANISM: Homo sapiens

<400> SEQUENCE: 247

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Arg Leu Ala Trp Tyr Gln Gln Lys Pro Gly Gln Ala Pro Arg Leu Leu
        35                  40                  45

Ile Tyr Gly Ala Ser Lys Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Ser Gln Asp Pro
                85                  90                  95

Ser Ser Thr Phe Gly Gln Gly Thr Lys Val Glu Ile Lys Arg Thr
            100                 105                 110

<210> SEQ ID NO 248
<211> LENGTH: 110
<212> TYPE: PRT
<213> ORGANISM: Homo sapiens

<400> SEQUENCE: 248

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ile Val Ser Gly Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Val Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Trp Ser Leu Arg Ser Pro
                85                  90                  95

Phe Thr Phe Gly Gln Gly Thr Lys Val Glu Ile Lys Arg Thr
            100                 105                 110

<210> SEQ ID NO 249
<211> LENGTH: 111

```
<212> TYPE: PRT
<213> ORGANISM: Homo sapiens

<400> SEQUENCE: 249

Asp Ile Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Asn Asp Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Ser Thr Tyr Asp Arg Arg Thr
                85                  90                  95

Phe Ser Val Phe Gly Gly Gly Thr Lys Leu Thr Val Leu Gly Gln
            100                 105                 110

<210> SEQ ID NO 250
<211> LENGTH: 111
<212> TYPE: PRT
<213> ORGANISM: Homo sapiens

<400> SEQUENCE: 250

Asp Ile Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Asn Asp Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Ser Thr Tyr Asp Arg Arg Thr
                85                  90                  95

Phe Ser Val Phe Gly Gly Gly Thr Lys Leu Thr Val Leu Gly Gln
            100                 105                 110

<210> SEQ ID NO 251
<211> LENGTH: 110
<212> TYPE: PRT
<213> ORGANISM: Homo sapiens

<400> SEQUENCE: 251

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Arg Leu Ala Trp Tyr Gln Gln Lys Pro Gly Gln Ala Pro Arg Leu Leu
        35                  40                  45

Ile Tyr Gly Ala Ser Lys Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Gln Gln Tyr Tyr Asp Phe Pro
```

```
                    85                  90                  95

Pro Thr Phe Gly Gln Gly Thr Lys Val Glu Ile Lys Arg Thr
                100                 105                 110

<210> SEQ ID NO 252
<211> LENGTH: 112
<212> TYPE: PRT
<213> ORGANISM: Homo sapiens

<400> SEQUENCE: 252

Asp Ile Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Asn Asp Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Ser Ser Trp Asp Arg Ala Asp
                85                  90                  95

Gly Ser Tyr Val Phe Gly Gly Gly Thr Lys Leu Thr Val Leu Gly Gln
            100                 105                 110

<210> SEQ ID NO 253
<211> LENGTH: 113
<212> TYPE: PRT
<213> ORGANISM: Homo sapiens

<400> SEQUENCE: 253

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Ser Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ala Trp Ala His Met
                85                  90                  95

Ser Leu Gly Lys Val Phe Gly Gly Gly Thr Lys Leu Thr Val Leu Gly
            100                 105                 110

Gln

<210> SEQ ID NO 254
<211> LENGTH: 113
<212> TYPE: PRT
<213> ORGANISM: Homo sapiens

<400> SEQUENCE: 254

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30
```

Asn Tyr Val Ser Trp Tyr Gln Gln His Pro Gly Lys Ala Pro Lys Leu
            35                  40                  45

Met Ile Tyr Ser Val Ser Lys Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ala Thr Trp Asp His Ser
                85                  90                  95

Gln Met Gly Lys Val Phe Gly Gly Gly Thr Lys Leu Thr Val Leu Gly
            100                 105                 110

Gln

<210> SEQ ID NO 255
<211> LENGTH: 224
<212> TYPE: PRT
<213> ORGANISM: Homo sapiens

<400> SEQUENCE: 255

Asp Ile Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Ile Gly Gly Tyr
            20                  25                  30

Asn Ser Val Ser Trp Tyr Gln Gln His Pro Gly Lys Ala Pro Lys Leu
            35                  40                  45

Met Ile Tyr Gly Val Asn Asn Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Asp Ile Glu
                85                  90                  95

Ser Ala Thr Pro Val Phe Gly Gly Gly Thr Lys Leu Thr Val Leu Gly
            100                 105                 110

Gln Asp Ile Val Leu Thr Gln Pro Pro Ser Val Ser Gly Ala Pro Gly
            115                 120                 125

Gln Arg Val Thr Ile Ser Cys Ser Gly Ser Ser Asn Ile Gly Ser
            130                 135                 140

Asn Tyr Val Ser Trp Tyr Gln Gln Leu Pro Gly Thr Ala Pro Lys Leu
145                 150                 155                 160

Leu Ile Tyr Asn Asp Asn Gln Arg Pro Ser Gly Val Pro Asp Arg Phe
                165                 170                 175

Ser Gly Ser Lys Ser Gly Thr Ser Ala Ser Leu Ala Ile Thr Gly Leu
            180                 185                 190

Gln Ser Glu Asp Glu Ala Asp Tyr Tyr Cys Ser Thr Tyr Asp Arg Arg
        195                 200                 205

Thr Phe Ser Val Phe Gly Gly Gly Thr Lys Leu Thr Val Leu Gly Gln
210                 215                 220

<210> SEQ ID NO 256
<211> LENGTH: 109
<212> TYPE: PRT
<213> ORGANISM: Homo sapiens

<400> SEQUENCE: 256

Asp Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ile Val Ser Gly Tyr

```
                20                  25                  30
Leu Ala Trp Tyr Gln Gln Lys Pro Gly Gln Ala Pro Arg Leu Leu Ile
                35                  40                  45

Tyr Gly Ala Ser Ser Arg Ala Thr Gly Val Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Thr Tyr Tyr Cys Gln Gln Tyr Tyr Asn Phe Ser Phe
                85                  90                  95

Thr Phe Gly Gln Gly Thr Lys Val Glu Ile Lys Arg Thr
                100                 105
```

<210> SEQ ID NO 257
<211> LENGTH: 109
<212> TYPE: PRT
<213> ORGANISM: Homo sapiens

<400> SEQUENCE: 257

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Gly Ser Tyr
                20                  25                  30

Leu Asn Trp Tyr Gln Gln Lys Pro Gly Lys Ala Pro Lys Leu Leu Ile
                35                  40                  45

Tyr Asn Ser Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Ser Asn Met Pro Ile
                85                  90                  95

Thr Phe Gly Gln Gly Thr Lys Val Glu Ile Lys Arg Thr
                100                 105
```

<210> SEQ ID NO 258
<211> LENGTH: 111
<212> TYPE: PRT
<213> ORGANISM: Homo sapiens

<400> SEQUENCE: 258

```
Asp Ile Ala Leu Thr Gln Pro Ala Ser Val Ser Gly Ala Pro Gly Gln
1               5                   10                  15

Arg Val Thr Ile Ser Cys Thr Gly Thr Ser Ser Asp Val Gly Ala Ser
                20                  25                  30

Asp Thr Val Thr Trp Tyr Gln Gln His Pro Gly Lys Ala Pro Lys Leu
                35                  40                  45

Met Ile Tyr Ala Val Asn Lys Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Arg Asp Ser Ser
                85                  90                  95

Ser Met Val Phe Gly Gly Gly Thr Lys Leu Thr Val Leu Gly Gln
                100                 105                 110
```

<210> SEQ ID NO 259
<211> LENGTH: 114
<212> TYPE: PRT

<213> ORGANISM: Homo sapiens

<400> SEQUENCE: 259

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Thr Tyr Leu Ser Trp Tyr Leu Gln Lys Pro Gly Gln Ser
        35                  40                  45

Pro Gln Leu Leu Ile Tyr Leu Gly Ser Lys Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Tyr Asp Ser Ser Ser Thr Phe Gly Gln Gly Thr Lys Val Glu Ile Lys
            100                 105                 110

Arg Thr

<210> SEQ ID NO 260
<211> LENGTH: 112
<212> TYPE: PRT
<213> ORGANISM: Homo sapiens

<400> SEQUENCE: 260

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Pro Asn
            20                  25                  30

Tyr Val Ser Trp Tyr Gln Gln Leu Pro Gly Thr Ala Pro Lys Leu Leu
        35                  40                  45

Ile His Gly Asn Ala Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Tyr Asp Phe Phe Thr
                85                  90                  95

Asn Ser Ser Val Phe Gly Gly Gly Thr Lys Leu Thr Val Leu Gly Gln
            100                 105                 110

<210> SEQ ID NO 261
<211> LENGTH: 110
<212> TYPE: PRT
<213> ORGANISM: Homo sapiens

<400> SEQUENCE: 261

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Leu Thr Ser Asn
            20                  25                  30

Gln Leu Ala Trp Tyr Gln Gln Lys Pro Gly Gln Ala Pro Arg Leu Leu
        35                  40                  45

Ile Tyr Asp Ser Ser Asn Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Gly Ser Phe Pro
            85                  90                  95

Ala Thr Phe Gly Gln Gly Thr Lys Val Glu Ile Lys Arg Thr
            100                 105                 110

<210> SEQ ID NO 262
<211> LENGTH: 113
<212> TYPE: PRT
<213> ORGANISM: Homo sapiens

<400> SEQUENCE: 262

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Asn
            20                  25                  30

Asn Phe Val Ser Trp Tyr Gln Gln His Pro Gly Lys Ala Pro Lys Leu
        35                  40                  45

Met Ile Tyr Tyr Gly Asp Ser Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Trp Asp Ala Pro
                85                  90                  95

Met Gly Met Trp Val Phe Gly Gly Gly Thr Lys Leu Thr Val Leu Gly
            100                 105                 110

Gln

<210> SEQ ID NO 263
<211> LENGTH: 109
<212> TYPE: PRT
<213> ORGANISM: Homo sapiens

<400> SEQUENCE: 263

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Ser Ala
            20                  25                  30

Leu Ala Trp Tyr Gln Gln Lys Pro Gly Lys Ala Pro Lys Leu Leu Ile
        35                  40                  45

Tyr Gly Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Ser Val
                85                  90                  95

Thr Phe Gly Gln Gly Thr Lys Val Glu Ile Lys Arg Thr
            100                 105

<210> SEQ ID NO 264
<211> LENGTH: 112
<212> TYPE: PRT
<213> ORGANISM: Homo sapiens

<400> SEQUENCE: 264

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asn Phe
            20                  25                  30

```
Asn Tyr Val Asn Trp Tyr Gln Gln His Pro Gly Lys Ala Pro Lys Leu
            35                  40                  45

Met Ile Tyr Ser Val Ser Ser Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gly Ala Tyr Thr Thr Asp
                 85                  90                  95

Thr Leu Ser Val Phe Gly Gly Gly Thr Lys Leu Thr Val Leu Gly Gln
                100                 105                 110
```

<210> SEQ ID NO 265
<211> LENGTH: 110
<212> TYPE: PRT
<213> ORGANISM: Homo sapiens

<400> SEQUENCE: 265

```
Asp Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Thr Ser Asn
                20                  25                  30

Tyr Leu Ala Trp Tyr Gln Gln Lys Pro Gly Gln Ala Pro Arg Leu Leu
            35                  40                  45

Ile Tyr Gly Ser Ser Ser Arg Ala Thr Gly Val Pro Ala Arg Phe Ser
 50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Gln Gln Tyr Ser Asp Ile Pro
                 85                  90                  95

Ala Thr Phe Gly Gln Gly Thr Lys Val Glu Ile Lys Arg Thr
                100                 105                 110
```

<210> SEQ ID NO 266
<211> LENGTH: 109
<212> TYPE: PRT
<213> ORGANISM: Homo sapiens

<400> SEQUENCE: 266

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Asn Arg Ser
                20                  25                  30

Leu Thr Trp Tyr Gln Gln Lys Pro Gly Lys Ala Pro Lys Leu Leu Ile
            35                  40                  45

Tyr Ala Ala Ser Asn Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Val Tyr Tyr Cys Leu Gln Val Tyr Asn Leu Pro Leu
                 85                  90                  95

Thr Phe Gly Gln Gly Thr Lys Val Glu Ile Lys Arg Thr
                100                 105
```

<210> SEQ ID NO 267
<211> LENGTH: 109
<212> TYPE: PRT
<213> ORGANISM: Homo sapiens

<400> SEQUENCE: 267

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Arg Ser
            20                  25                  30

Leu Thr Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Leu Gln Val Tyr Asn Leu Pro Leu
                85                  90                  95

Thr Phe Gly Gln Gly Thr Lys Val Glu Ile Lys Arg Thr
            100                 105

<210> SEQ ID NO 268
<211> LENGTH: 110
<212> TYPE: PRT
<213> ORGANISM: Homo sapiens

<400> SEQUENCE: 268

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Pro Asn Phe Tyr Val
            20                  25                  30

His Trp Tyr Gln Gln Lys Pro Gly Gln Ala Pro Val Leu Val Ile Tyr
        35                  40                  45

Glu Asp Ser Asp Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Lys Pro Thr Phe Ser
                85                  90                  95

Gly Val Phe Gly Gly Gly Thr Lys Leu Thr Val Leu Gly Gln
            100                 105                 110

<210> SEQ ID NO 269
<211> LENGTH: 113
<212> TYPE: PRT
<213> ORGANISM: Homo sapiens

<400> SEQUENCE: 269

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Arg Tyr
            20                  25                  30

His Tyr Val Ser Trp Tyr Gln Gln His Pro Gly Lys Ala Pro Lys Val
        35                  40                  45

Met Ile Tyr Ser Val Ser Lys Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ala Tyr Asp Thr Asn
                85                  90                  95

```
Asn Tyr Leu Ser Val Phe Gly Gly Gly Thr Lys Leu Thr Val Leu Gly
                100                 105                 110
Gln

<210> SEQ ID NO 270
<211> LENGTH: 108
<212> TYPE: PRT
<213> ORGANISM: Homo sapiens

<400> SEQUENCE: 270

Asp Ile Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Asn Asn
            20                  25                  30

Ser Val Asn Trp Tyr Gln Gln Leu Pro Gly Thr Ala Pro Lys Leu Leu
        35                  40                  45

Ile Tyr Asn Asn Gln Arg Pro Ser Gly Val Pro Asp Arg Phe Ser Gly
    50                  55                  60

Ser Lys Ser Gly Thr Ser Ala Ser Leu Ala Ile Thr Gly Leu Gln Ser
65                  70                  75                  80

Glu Asp Glu Ala Asp Tyr Tyr Cys Gln Ala Tyr Ala Ser Asn Ile Val
                85                  90                  95

Phe Gly Gly Gly Thr Lys Leu Thr Val Leu Gly Gln
                100                 105

<210> SEQ ID NO 271
<211> LENGTH: 111
<212> TYPE: PRT
<213> ORGANISM: Homo sapiens

<400> SEQUENCE: 271

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asp Tyr
            20                  25                  30

Asn Tyr Val Ser Trp Tyr Gln Gln His Pro Gly Lys Ala Pro Lys Leu
        35                  40                  45

Met Ile Tyr Arg Val Asp Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Trp Val Gly Pro
                85                  90                  95

Ser Thr Val Phe Gly Gly Gly Thr Lys Leu Thr Val Leu Gly Gln
                100                 105                 110

<210> SEQ ID NO 272
<211> LENGTH: 111
<212> TYPE: PRT
<213> ORGANISM: Homo sapiens

<400> SEQUENCE: 272

Asp Ile Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45
```

```
Ile Tyr Ser Asn Ser Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
 65                  70                  75                  80

Ser Glu Asp Glu Ala Asp Tyr Tyr Cys Gln Ser Tyr Asp His Asn Ser
                 85                  90                  95

Tyr Thr Val Phe Gly Gly Gly Thr Lys Leu Thr Val Leu Gly Gln
                100                 105                 110
```

<210> SEQ ID NO 273
<211> LENGTH: 108
<212> TYPE: PRT
<213> ORGANISM: Homo sapiens

<400> SEQUENCE: 273

```
Asp Ile Glu Leu Thr Gln Pro Pro Ser Val Ser Val Ala Pro Gly Gln
 1               5                  10                  15

Thr Ala Arg Ile Ser Cys Ser Gly Asp Asn Leu Arg Ser Lys Tyr Ala
                20                  25                  30

His Trp Tyr Gln Gln Lys Pro Gly Gln Ala Pro Val Leu Val Ile Tyr
            35                  40                  45

Ser Lys Asp Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Ser Ser Trp Ala His Asp His Lys Val
                 85                  90                  95

Phe Gly Gly Gly Thr Lys Leu Thr Val Leu Gly Gln
                100                 105
```

<210> SEQ ID NO 274
<211> LENGTH: 110
<212> TYPE: PRT
<213> ORGANISM: Homo sapiens

<400> SEQUENCE: 274

```
Asp Ile Glu Leu Thr Gln Pro Pro Ser Val Ser Val Ala Pro Gly Gln
 1               5                  10                  15

Thr Ala Arg Ile Ser Cys Ser Gly Asp Asn Ile Gly Ser Lys Val Ala
                20                  25                  30

Thr Trp Tyr Gln Gln Lys Pro Gly Gln Ala Pro Val Leu Val Ile Tyr
            35                  40                  45

Tyr Asp Asn Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Ser Tyr Asp Gly Gln Met Ser Thr
                 85                  90                  95

Ser Val Phe Gly Gly Gly Thr Lys Leu Thr Val Leu Gly Gln
                100                 105                 110
```

<210> SEQ ID NO 275
<211> LENGTH: 113
<212> TYPE: PRT
<213> ORGANISM: Homo sapiens

<400> SEQUENCE: 275

-continued

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Ser Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Thr Tyr Asp His Thr
                85                  90                  95

Ser Ser Gly Phe Val Phe Gly Gly Gly Thr Lys Leu Thr Val Leu Gly
            100                 105                 110

Gln

<210> SEQ ID NO 276
<211> LENGTH: 111
<212> TYPE: PRT
<213> ORGANISM: Homo sapiens

<400> SEQUENCE: 276

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly His Phe
            20                  25                  30

Asn Tyr Val Ser Trp Tyr Gln Gln His Pro Gly Lys Ala Pro Lys Leu
        35                  40                  45

Met Ile Tyr Ser Val Ile Ser Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Phe Thr Phe Pro
                85                  90                  95

Ser Leu Val Phe Gly Gly Gly Thr Lys Leu Thr Val Leu Gly Gln
            100                 105                 110

<210> SEQ ID NO 277
<211> LENGTH: 112
<212> TYPE: PRT
<213> ORGANISM: Homo sapiens

<400> SEQUENCE: 277

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser His
            20                  25                  30

Thr Val Asn Trp Tyr Gln Gln Leu Pro Gly Thr Ala Pro Lys Leu Leu
        35                  40                  45

Ile Tyr Asp Val Asn Lys Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Ala Ser Trp Asp Ser Val Gln
                85                  90                  95

Val Ser Pro Val Phe Gly Gly Gly Thr Lys Leu Thr Val Leu Gly Gln

<210> SEQ ID NO 278
<211> LENGTH: 111
<212> TYPE: PRT
<213> ORGANISM: Homo sapiens

<400> SEQUENCE: 278

Asp Ile Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Asn Asn
            20                  25                  30

Arg Val Ser Trp Tyr Gln Gln Leu Pro Gly Thr Ala Pro Lys Leu Leu
        35                  40                  45

Ile Tyr Gly Asn Asn Lys Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Ser Ala Trp Asp Leu Leu Glu
                85                  90                  95

Val Tyr Val Phe Gly Gly Gly Thr Lys Leu Thr Val Leu Gly Gln
            100                 105                 110

<210> SEQ ID NO 279
<211> LENGTH: 111
<212> TYPE: PRT
<213> ORGANISM: Homo sapiens

<400> SEQUENCE: 279

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Thr Tyr
            20                  25                  30

Asn His Val Ser Trp Tyr Gln Gln His Pro Gly Lys Ala Pro Lys Leu
        35                  40                  45

Met Ile Tyr Asn Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ala Tyr Ala Pro Ser
                85                  90                  95

Ala Val Val Phe Gly Gly Gly Thr Lys Leu Thr Val Leu Gly Gln
            100                 105                 110

<210> SEQ ID NO 280
<211> LENGTH: 113
<212> TYPE: PRT
<213> ORGANISM: Homo sapiens

<400> SEQUENCE: 280

Asp Ile Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ile Gly
            20                  25                  30

Tyr Asp Val Asn Trp Tyr Gln Gln Leu Pro Gly Thr Ala Pro Lys Leu
        35                  40                  45

Leu Ile Tyr Lys Asn Thr Asn Arg Pro Ser Gly Val Pro Asp Arg Phe
    50                  55                  60

```
Ser Gly Ser Lys Ser Gly Thr Ser Ala Ser Leu Ala Ile Thr Gly Leu
 65                  70                  75                  80

Gln Ser Glu Asp Glu Ala Asp Tyr Tyr Cys Ser Ser Tyr Asp Ser Phe
                 85                  90                  95

His His Gly Ile Val Phe Gly Gly Gly Thr Lys Leu Thr Val Leu Gly
            100                 105                 110

Gln

<210> SEQ ID NO 281
<211> LENGTH: 113
<212> TYPE: PRT
<213> ORGANISM: Homo sapiens

<400> SEQUENCE: 281

Asp Ile Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Leu Gly Gly Tyr
                20                  25                  30

Ser Tyr Val Ser Trp Tyr Gln Gln His Pro Gly Lys Ala Pro Lys Leu
            35                  40                  45

Met Ile Tyr Asn Val Asn Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Asp Tyr Val
                 85                  90                  95

Ser Ser Asp Thr Val Phe Gly Gly Gly Thr Lys Leu Thr Val Leu Gly
            100                 105                 110

Gln

<210> SEQ ID NO 282
<211> LENGTH: 113
<212> TYPE: PRT
<213> ORGANISM: Homo sapiens

<400> SEQUENCE: 282

Asp Ile Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Val
            35                  40                  45

Met Ile Tyr Gly Val Thr Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gly Thr Tyr Asp Glu His
                 85                  90                  95

Gly Phe His Ile Val Phe Gly Gly Gly Thr Lys Leu Thr Val Leu Gly
            100                 105                 110

Gln

<210> SEQ ID NO 283
<211> LENGTH: 112
<212> TYPE: PRT
<213> ORGANISM: Homo sapiens
```

<400> SEQUENCE: 283

Asp Ile Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Asn Tyr
            20                  25                  30

Arg Val Ser Trp Tyr Gln Gln Leu Pro Gly Thr Ala Pro Lys Leu Leu
        35                  40                  45

Ile Tyr Gly Asn Asn Lys Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Ser Thr Tyr Thr Gly Leu Pro
                85                  90                  95

Phe Thr Thr Val Phe Gly Gly Gly Thr Lys Leu Thr Val Leu Gly Gln
                100                 105                 110

<210> SEQ ID NO 284
<211> LENGTH: 363
<212> TYPE: DNA
<213> ORGANISM: Homo sapiens

<400> SEQUENCE: 284
caggtggaat tggttcagag cggcgcggaa gtgaaaaaac cgggcgaaag cctgaaaatt      60
agctgcaaag gttccggata ttcctttact aattattgga ttggttgggt gcgccagatg     120
cctgggaagg gtctcgagtg gatgggcgtt atcatgccgt ctgatagcta tacccgttat     180
tctccgagct ttcagggcca ggtgaccatt agcgcggata aaagcattag caccgcgtat     240
cttcaatgga gcagcctgaa agcgagcgat acggccatgt attattgcgc gcgttatggt     300
catggtatgt atggtggtgc tcttgatgtt tggggccaag caccctggt gacggttagc     360
tca                                                                   363

<210> SEQ ID NO 285
<211> LENGTH: 363
<212> TYPE: DNA
<213> ORGANISM: Homo sapiens

<400> SEQUENCE: 285
caggtgcaat tggttcagag cggcgcggaa gtgaaaaaac cgggcgaaag cctgaaaatt      60
agctgcaaag gttccggata ttcctttact aattattgga ttggttgggt gcgccagatg     120
cctgggaagg gtctcgagtg gatgggcttt atttggcctg ttgattcttg gactcagtat     180
tctccttctt ttcagggtca ggtcaccatt agcgcggata aaagcattag caccgcgtat     240
cttcaatgga gcagcctgaa agcgagcgat acggccatgt attattgcgc gcgttatggt     300
catggtatgt atggtggtgc tcttgatgtt tggggccaag caccctggt gacggttagc     360
tca                                                                   363

<210> SEQ ID NO 286
<211> LENGTH: 363
<212> TYPE: DNA
<213> ORGANISM: Homo sapiens

<400> SEQUENCE: 286
caggtgcaat tggttcagag cggcgcggaa gtgaaaaaac cgggcgaaag cctgaaaatt      60
agctgcaaag gttccggata ttcctttact aattattgga ttggttgggt gcgccagatg     120

```
cctgggaagg gtctcgagtg gatgggcttt atttggcctg ttgattcttg gactcagtat    180
tctccttctt ttcagggtca ggtcaccatt agcgcggata aaagcattag caccgcgtat    240
cttcaatgga gcagcctgaa agcgagcgat acggccatgt attattgcgc gcgttatggt    300
catggtatgt atggtggtgc tcttgatgtt tggggccaag gcaccctggt gacggttagc    360
tca                                                                  363

<210> SEQ ID NO 287
<211> LENGTH: 363
<212> TYPE: DNA
<213> ORGANISM: Homo sapiens

<400> SEQUENCE: 287
caggtgcaat tggttcagag cggcgcggaa gtgaaaaaac cgggcgaaag cctgaaaatt    60
agctgcaaag gttccggata ttcctttact aattattgga ttggttgggt gcgccagatg    120
cctgggaagg gtctcgagtg gatgggcatt atttggccta ttgattcttt tactcagtat    180
tctccttctt ttcagggtca ggtgaccatt agcgcggata aaagcattag caccgcgtat    240
cttcaatgga gcagcctgaa agcgagcgat acggccatgt attattgcgc gcgttatggt    300
catggtatgt atggtggtgc tcttgatgtt tggggccaag gcaccctggt gacggttagc    360
tca                                                                  363

<210> SEQ ID NO 288
<211> LENGTH: 363
<212> TYPE: DNA
<213> ORGANISM: Homo sapiens

<400> SEQUENCE: 288
caggtgcaat tggttcagag cggcgcggaa gtgaaaaaac cgggcgaaag cctgaaaatt    60
agctgcaaag gttccggata ttcctttact aattattgga ttggttgggt gcgccagatg    120
cctgggaagg gtctcgagtg gatgggcgtt atcatgccgt ctgatagcta tacccgttat    180
tctccgagct ttcagggcca ggtgaccatt agcgcggata aaagcattag caccgcgtat    240
cttcaatgga gcagcctgaa agcgagcgat acggccatgt attattgcgc gcgttatggt    300
catggtatgt atggtggtgc tcttgatgtt tggggccaag gcaccctggt gacggttagc    360
tca                                                                  363

<210> SEQ ID NO 289
<211> LENGTH: 363
<212> TYPE: DNA
<213> ORGANISM: Homo sapiens

<400> SEQUENCE: 289
caggtgcaat tggttcagag cggcgcggaa gtgaaaaaac cgggcgaaag cctgaaaatt    60
agctgcaaag gttccggata ttcctttact aattattgga ttggttgggt gcgccagatg    120
cctgggaagg gtctcgagtg gatgggcgtt atcatgccgt ctgatagcta tacccgttat    180
tctccgagct ttcagggcca ggtgaccatt agcgcggata aaagcattag caccgcgtat    240
cttcaatgga gcagcctgaa agcgagcgat acggccatgt attattgcgc gcgttatggt    300
catggtatgt atggtggtgc tcttgatgtt tggggccaag gcaccctggt gacggttagc    360
tca                                                                  363

<210> SEQ ID NO 290
```

```
<211> LENGTH: 363
<212> TYPE: DNA
<213> ORGANISM: Homo sapiens

<400> SEQUENCE: 290
caggtgcaat tggttcagag cggcgcggaa gtgaaaaaac cgggcgaaag cctgaaaatt      60
agctgcaaag gttccggata ttcctttact aattattgga ttggttgggt gcgccagatg     120
cctgggaagg gtctcgagtg gatgggcgtt atcatgccgt ctgatagcta tacccgttat     180
tctccgagct ttcagggcca ggtgaccatt agcgcggata aaagcattag caccgcgtat     240
cttcaatgga gcagcctgaa agcgagcgat acggccatgt attattgcgc gcgttatggt     300
catggtatgt atggtggtgc tcttgatgtt tggggccaag gcaccctggt gacggttagc     360
tca                                                                  363

<210> SEQ ID NO 291
<211> LENGTH: 363
<212> TYPE: DNA
<213> ORGANISM: Homo sapiens

<400> SEQUENCE: 291
caggtgcaat tggtggaaag cggcggcggc ctggtgcaac cgggcggcag cctgcgtctg      60
agctgcgcgg cctccggatt tacctttttct gattatgcta tgtcttgggt gcgccaagcc    120
cctgggaagg gtctcgagtg ggtgagcgct atcatgtatg attctagctc tacctttttat    180 gcggatagcg tgaaaggccg ttttaccatt tcacgtgata attcgaaaaa caccctgtat     240
ctgcaaatga acagcctgcg tgcggaagat acggccgtgt attattgcgc gcgtattaat     300
tatatttata agggtgttca ttttgattat tggggccaag gcaccctggt gacggttagc    360
tca                                                                  363

<210> SEQ ID NO 292
<211> LENGTH: 357
<212> TYPE: DNA
<213> ORGANISM: Homo sapiens

<400> SEQUENCE: 292
caggtggaat tggttcagag cggcgcggaa gtgaaaaaac cgggcgcgag cgtgaaagtg      60
agctgcaaag cctccggata tacctttact ggtaattata ttaattgggt ccgccaagcc    120
cctgggcagg gtctcgagtg gatgggcatt atcaatccgc atggtggcga tacgaagtac    180
gcgcagaagt ttcagggccg ggtgaccatg acccgtgata ccagcattag caccgcgtat    240
atggaactga gcagcctgcg tagcgaagat acggccgtgt attattgcgc gcgttggcat    300
catggtactt ggatttttga ttattggggc caaggcaccc tggtgacggt tagctca      357

<210> SEQ ID NO 293
<211> LENGTH: 357
<212> TYPE: DNA
<213> ORGANISM: Homo sapiens

<400> SEQUENCE: 293
caggtgcaat tggttcagag cggcgcggaa gtgaaaaaac cgggcgcgag cgtgaaagtg      60
agctgcaaag cctccggata tacctttact ggtaattata ttaattgggt ccgccaagcc    120
cctgggcagg gtctcgagtg gatgggcatt attaatccta ctaagggttg gactcttttat   180 gctcagaagt ttcagggtcg ggtcaccatg acccgtgata ccagcattag caccgcgtat    240
atggaactga gcagcctgcg tagcgaagat acggccgtgt attattgcgc gcgttggcat    300
```

```
catggtactt ggattttga ttattggggc caaggcaccc tggtgacggt tagctca       357
```

<210> SEQ ID NO 294
<211> LENGTH: 363
<212> TYPE: DNA
<213> ORGANISM: Homo sapiens

<400> SEQUENCE: 294

```
caggtgcaat tggttcagag cggcgcggaa gtgaaaaaac cgggcgaaag cctgaaaatt    60
agctgcaaag gttccggata ttccttact aattattgga ttggttgggt gcgccagatg   120
cctgggaagg gtctcgagtg gatgggcttt atttggcctt ctgattcttg gacttcttat   180
tctccttctt ttcagggtca ggtgaccatt agcgcggata aaagcattag caccgcgtat   240
cttcaatgga gcagcctgaa agcgagcgat acggccatgt attattgcgc gcgttatggt   300
catggtatgt atggtggtgc tcttgatgtt tggggccaag cacctggt gacggttagc   360
tca                                                                363
```

<210> SEQ ID NO 295
<211> LENGTH: 357
<212> TYPE: DNA
<213> ORGANISM: Homo sapiens

<400> SEQUENCE: 295

```
caggtgcaat tggttcagag cggcgcggaa gtgaaaaaac cgggcgcgag cgtgaaagtg    60
agctgcaaag cctccggata tacctttact ggtaattata ttaattgggt ccgccaagcc   120
cctgggcagg gtctcgagtg gatgggcatt atcaatccgc atggtggcga tacgaagtac   180
gcgcagaagt ttcagggccg ggtgaccatg acccgtgata ccagcattag caccgcgtat   240
atggaactga gcagcctgcg tagcgaagat acggccgtgt attattgcgc gcgttggcat   300
catggtactt ggattttga ttattggggc caaggcaccc tggtgacggt tagctca       357
```

<210> SEQ ID NO 296
<211> LENGTH: 345
<212> TYPE: DNA
<213> ORGANISM: Homo sapiens

<400> SEQUENCE: 296

```
caggtgcaat tggttcagtc tggcgcggaa gtgaaaaaac cgggcagcag cgtgaaagtg    60
agctgcaaag cctccggagg cacttttct tcttattatt tttcttgggt gcgccaagcc   120
cctgggcagg gtctcgagtg gatgggcggt atcattccga agtttggctc tgcgaattac   180
gcgcagaagt ttcagggccg ggtgaccatt accgcggatg aaagcaccag caccgcgtat   240
atggaactga gcagcctgcg tagcgaagat acggccgtgt attattgcgc gcgtcgtact   300
tctatggatt attggggcca aggcaccctg gtgacggtta gctca                  345
```

<210> SEQ ID NO 297
<211> LENGTH: 345
<212> TYPE: DNA
<213> ORGANISM: Homo sapiens

<400> SEQUENCE: 297

```
caggtgcaat tggttcagtc tggcgcggaa gtgaaaaaac cgggcagcag cgtgaaagtg    60
agctgcaaag cctccggagg cacttttct tcttattatt tttcttgggt gcgccaagcc   120
cctgggcagg gtctcgagtg gatgggcggt atcattccga agtttggctc tgcgaattac   180
```

```
gcgcagaagt tcagggccg ggtgaccatt accgcggatg aaagcaccag caccgcgtat    240
atggaactga gcagcctgcg tagcgaagat acggccgtgt attattgcgc gcgtcgtact    300
tctatggatt attggggcca aggcaccctg gtgacggtta gctca                   345

<210> SEQ ID NO 298
<211> LENGTH: 360
<212> TYPE: DNA
<213> ORGANISM: Homo sapiens

<400> SEQUENCE: 298
caggtggaat tggttcagag cggcgcggaa gtgaaaaaac cgggcgaaag cctgaaaatt    60
agctgcaaag gttccggata ttcctttact tcttattgga ttggttgggt gcgccaggcc   120
cctgggaagg gtctcgagtg gatgggcatt atcgatccgg gtgatagccg taccgttat   180 tctccgagct ttcagggcca ggtgaccatt agcgcggata aaagcattag caccgcgtat   240
cttcaatgga gcagcctgaa agcgagcgat acggccatgt attattgcgc gcgtggtcag   300
ctttatggtg gtacttatat ggatggttgg ggccaaggca cctggtgac ggttagctca    360

<210> SEQ ID NO 299
<211> LENGTH: 363
<212> TYPE: DNA
<213> ORGANISM: Homo sapiens

<400> SEQUENCE: 299
caggtgcaat tggtggaaag cggcggcggc ctggtgcaac cgggcggcag cctgcgtctg    60
agctgcgcgg cctccggatt taccttttct gattatgcta tgtcttgggt gcgccaagcc   120
cctgggaagg gtctcgagtg ggtgagcgct atcatgtatg attctagctc tacctttat   180 gcggatagcg tgaaaggccg ttttaccatt tcacgtgata attcgaaaaa cacccctgtat  240 ctgcaaatga acagcctgcg tgcggaagat acggccgtgt attattgcgc gcgtattaat   300
tatatttata agggtgttca ttttgattat tggggccaag gcaccctggt gacggttagc   360
tca                                                                 363

<210> SEQ ID NO 300
<211> LENGTH: 348
<212> TYPE: DNA
<213> ORGANISM: Homo sapiens

<400> SEQUENCE: 300
caggtgcaat tgcaagaaag tggtccgggc ctggtgaaac cgggcgaaac cctgagcctg    60
acctgcaccg tttccggagg cagcatttct aattattatt ggtcttggat tcgccaggcc   120
cctgggaagg gtctcgagtg gattggcgag atctatcatt ctggcggtac ctattataat   180
ccgagcctga aaggccgggt gaccattagc gttgatactt cgaaaaacca gtttagcctg   240
aaactgagca gcgtgacggc ggaagatacg gccgtgtatt attgcgcgcg tcctatggat   300
aatcttcctg atatttgggg ccaaggcacc ctggtgacgg ttagctca                348

<210> SEQ ID NO 301
<211> LENGTH: 348
<212> TYPE: DNA
<213> ORGANISM: Homo sapiens

<400> SEQUENCE: 301
caggtgcaat tggtggaaag cggcggcggc ctggtgcaac cgggcggcag cctgcgtctg    60
agctgcgcgg cctccggatt tacctttct tcttatggta tgtcttgggt gcgccaagcc   120
```

```
cctgggaagg gtctcgagtg ggtgagcggt atctcttatt cttctagcgc tacctattat    180
gcggatagcg tgaaaggccg ttttaccatt tcacgtgata attcgaaaaa caccctgtat    240
ctgcaaatga acagcctgcg tgcggaagat acggccgtgt attattgcgc gcgttatctt    300
tattattttg atgtttgggg ccaaggcacc ctggtgacgg ttagctca                 348
```

<210> SEQ ID NO 302
<211> LENGTH: 345
<212> TYPE: DNA
<213> ORGANISM: Homo sapiens

<400> SEQUENCE: 302

```
caggtgcaat tggtggaaag cggcggcggc ctggtgcaac cgggcggcag cctgcgtctg    60
agctgcgcgg cctccggatt tacctttcct aattcttgga tgtcttgggt gcgccaagcc   120
cctgggaagg gtctcgagtg ggtgagcgct atcacttatt ggggtagcaa tacctattat   180
gcggatagcg tgaaaggccg ttttaccatt tcacgtgata attcgaaaaa caccctgtat   240
ctgcaaatga acagcctgcg tgcggaagat acggccgtgt attattgcgc gcgtactaag   300 tttttttgcta attggggcca aggcaccctg gtgacggtta gctca                  345
```

<210> SEQ ID NO 303
<211> LENGTH: 345
<212> TYPE: DNA
<213> ORGANISM: Homo sapiens

<400> SEQUENCE: 303

```
caggtgcaat tggttcagtc tggcgcggaa gtgaaaaaac cgggcagcag cgtgaaagtg    60
agctgcaaag cctccggagg cacttttttct aattattcta tttcttgggt gcgccaagcc  120
cctgggcagg gtctcgagtg gatgggccgt atcattccga attttggcac tgcgaattac   180
gcgcagaagt tcagggccg ggtgaccatt accgcgatg aaagcaccag caccgcgtat     240
atggaactga gcagcctgcg tagcgaagat acggccgtgt attattgcgc gcgtggtatt   300
tattttgctt tttggggcca aggcaccctg gtgacggtta gctca                   345
```

<210> SEQ ID NO 304
<211> LENGTH: 360
<212> TYPE: DNA
<213> ORGANISM: Homo sapiens

<400> SEQUENCE: 304

```
caggtgcaat tggttcagag cggcgcggaa gtgaaaaaac cgggcgcgag cgtgaaagtg    60
agctgcaaag cctccggata ccctttact tcttatgctc ttcattgggt ccgccaagcc    120
cctgggcagg gtctcgagtg gatgggcatt atcaatccgc agaatggcgg tacgaattac   180
gcgcagaagt tcagggccg ggtgaccatg acccgtgata ccagcattag caccgcgtat    240
atggaactga gcagcctgcg tagcgaagat acggccgtgt attattgcgc gcgtaagcat   300
aagtatcgta ttggttctat ggatgtttgg ggccaaggca ccctggtgac ggttagctca   360
```

<210> SEQ ID NO 305
<211> LENGTH: 351
<212> TYPE: DNA
<213> ORGANISM: Homo sapiens

<400> SEQUENCE: 305

```
caggtgcaat tggttcagag cggcgcggaa gtgaaaaaac cgggcgaaag cctgaaaatt    60
```

```
agctgcaaag gttccggata ttcctttact aattattgga ttggttgggt gcgccagatg    120
cctgggaagg gtctcgagtg gatgggcatt atcgatccgc gtgagagctt tacccgttat    180
tctccgagct ttcagggcca ggtgaccatt agcgcggata aaagcattag caccgcgtat    240
cttcaatgga gcagcctgaa agcgagcgat acggccatgt attattgcgc gcgttatatg    300
aagggtggtt atgattattg gggccaaggc accctggtga cggttagctc a             351

<210> SEQ ID NO 306
<211> LENGTH: 360
<212> TYPE: DNA
<213> ORGANISM: Homo sapiens

<400> SEQUENCE: 306
caggtgcaat tgcaacagtc tggtccgggc ctggtgaaaac cgagccaaac cctgagcctg    60
acctgtgcga tttccggaga tagcgtgagc tctcgttctg ctgcttgggg ttggattcgc    120
cagtctcctg ggcgtggcct cgagtggctg ggccgtatcg gttatcgtag caagtggatg    180
aacgattatg cggtgagcgt gaaaagccgg attaccatca cccggatac ttcgaaaaac     240 cagtttagcc tgcaactgaa cagcgtgacc ccggaagata cggccgtgta ttattgcgcg    300
cgtatgcagg gttttcagct tgattattgg ggccaaggca ccctggtgac ggttagctca    360

<210> SEQ ID NO 307
<211> LENGTH: 345
<212> TYPE: DNA
<213> ORGANISM: Homo sapiens

<400> SEQUENCE: 307
caggtgcaat tggttcagtc tggcgcggaa gtgaaaaaac cgggcagcag cgtgaaagtg    60
agctgcaaag cctccggagg cacttttcct aattattctc ttcattgggt gcgccaagcc   120
cctgggcagg gtctcgagtg gatgggcggt atcgttccga ttttggcac tgcgaattac    180 gcgcagaagt ttcagggccg ggtgaccatt accgcggatg aaagcaccag caccgcgtat    240
atggaactga gcagcctgcg tagcgaagat acggccgtgt attattgcgc gcgtacttat    300
acttttgctg tttggggcca aggcaccctg gtgacggtta gctca                    345

<210> SEQ ID NO 308
<211> LENGTH: 345
<212> TYPE: DNA
<213> ORGANISM: Homo sapiens

<400> SEQUENCE: 308
caggtgcaat tggttcagtc tggcgcggaa gtgaaaaaac cgggcagcag cgtgaaagtg    60
agctgcaaag cctccggagg cacttttcct aattattctc ttcattgggt gcgccaagcc   120
cctgggcagg gtctcgagtg gatgggcggt atcgttccga ttttggcac tgcgaattac    180 gcgcagaagt ttcagggccg ggtgaccatt accgcggatg aaagcaccag caccgcgtat    240
atggaactga gcagcctgcg tagcgaagat acggccgtgt attattgcgc gcgtacttat    300
acttttgctg tttggggcca aggcaccctg gtgacggtta gctca                    345

<210> SEQ ID NO 309
<211> LENGTH: 342
<212> TYPE: DNA
<213> ORGANISM: Homo sapiens

<400> SEQUENCE: 309
caggtgcaat tggttcagag cggcgcggaa gtgaaaaaac cgggcgcgag cgtgaaagtg    60
```

```
agctgcaaag cctccggata tacctttact atttatgata tgcattgggt ccgccaagcc    120
cctgggcagg gtctcgagtg gatgggctat atctctccgt attctggcga tacgaattac    180
gcgcagaagt ttcagggccg ggtgaccatg acccgtgata ccagcattag caccgcgtat    240
atggaactga gcagcctgcg tagcgaagat acggccgtgt attattgcgc gcgtggttgg    300
caggattttt ggggccaagg caccctggtg acggttagct ca                      342

<210> SEQ ID NO 310
<211> LENGTH: 378
<212> TYPE: DNA
<213> ORGANISM: Homo sapiens

<400> SEQUENCE: 310
caggtgcaat tgcaacagtc tggtccgggc ctggtgaaac cgagccaaac cctgagcctg     60
acctgtgcga tttccggaga tagcgtgagc tctaattctg ctgcttgggg ttggattcgc    120
cagtctcctg ggcgtggcct cgagtggctg ggccgtatct cttatcgtag ccgttggtat    180
aacaattatg cggtgagcgt gaaaagccgg attaccatca acccggatac ttcgaaaaac    240
cagtttagcc tgcaactgaa cagcgtgacc ccggaagata cggccgtgta ttattgcgcg    300
cgttattatt ctgatcattt tggtctttat ccttattttg attattgggg ccaaggcacc    360
ctggtgacgg ttagctca                                                  378

<210> SEQ ID NO 311
<211> LENGTH: 378
<212> TYPE: DNA
<213> ORGANISM: Homo sapiens

<400> SEQUENCE: 311
caggtgcaat tggttcagag cggcgcggaa gtgaaaaaac cgggcgaaag cctgaaaatt     60
agctgcaaag gttccggata ttcctttaat acttcttgga tttgggtgcg ccagatgcct    120
gggaagggtc tcgagtggat gggcattatc catccgggtc atagctatac ccgttattct    180
ccgagctttc agggccaggt gaccattagc gcggataaaa gcattagcac cgcgtatctt    240
caatggagca gcctgaaagc gagcgatacg gccatgtatt attgcgcgcg tggtgatggt    300
ggtccttctt ctcagggtaa ttattttggt tgggtttatg atgtttgggg ccaaggcacc    360
ctggtgacgg ttagctca                                                  378

<210> SEQ ID NO 312
<211> LENGTH: 375
<212> TYPE: DNA
<213> ORGANISM: Homo sapiens

<400> SEQUENCE: 312
caggtgcaat tgcaacagtc tggtccgggc ctggtgaaac cgagccaaac cctgagcctg     60
acctgtgcga tttccggaga tagcgtgagc tctaattctg ctgcttggtc ttggattcgc    120
cagtctcctg ggcgtggcct cgagtggctg ggccgtatct attatcgtag caagaagtgg    180
tataacgatt atgcggtgag cgtgaaaagc cggattacca tcaacccgga tacttcgaaa    240
aaccagttta gcctgcaact gaacagcgtg accccggaag atacgccgt gtattattgc     300 gcgcgtaatt attctggtcc tatgtattat tatggtgatg tttggggcca aggcaccctg    360
gtgacggtta gctca                                                     375

<210> SEQ ID NO 313
```

```
<211> LENGTH: 369
<212> TYPE: DNA
<213> ORGANISM: Homo sapiens

<400> SEQUENCE: 313
caggtgcaat tgcaacagtc tggtccgggc ctggtgaaac cgagccaaac cctgagcctg      60
acctgtgcga tttccggaga tagcgtgagc tctaattctg ctgcttggtc ttggattcgc     120
cagtctcctg ggcgtggcct cgagtggctg ggccgtatcc agtatcgtag caagtggtat     180
aacgcttatg cggtgagcgt gaaaagccgg attaccatca acccggatac ttcgaaaaac     240
cagtttagcc tgcaactgaa cagcgtgacc ccggaagata cggccgtgta ttattgcgcg     300
cgtggttttc atggttctac tatgtatttt gatgtttggg gccaaggcac cctggtgacg     360
gttagctca                                                             369

<210> SEQ ID NO 314
<211> LENGTH: 351
<212> TYPE: DNA
<213> ORGANISM: Homo sapiens

<400> SEQUENCE: 314
caggtgcaat tggttcagag cggcgcggaa gtgaaaaaac cgggcgaaag cctgaaaatt      60
agctgcaaag gttccggata ttcctttact acttattgga ttggttgggt gcgccaagcc     120
cctgggaagg gtctcgagtg gatgggcttt atctatccgg ataagagcta taccaattat     180
tctccgagct ttcagggcca ggtgaccatt agcgcggata aaagcattag caccgcgtat     240
cttcaatgga gcagcctgaa agcgagcgat acggccatgt attattgcgc gcgtggtctt     300
ggtggttctt ttgatgtttg gggccaaggc accctggtga cggttagctc a              351

<210> SEQ ID NO 315
<211> LENGTH: 369
<212> TYPE: DNA
<213> ORGANISM: Homo sapiens

<400> SEQUENCE: 315
caggtgcaat tgcaacagtc tggtccgggc ctggtgaaac cgagccaaac cctgagcctg      60
acctgtgcga tttccggaga tagcgtgagc tctaattctg cttcttggtc ttggattcgc     120
cagtctcctg ggcgtggcct cgagtggctg ggccgtatct attatcgtag ccagtggtat     180
aacgattatg cggtgagcgt gaaaagccgg attaccatca acccggatac ttcgaaaaac     240
cagtttagcc tgcaactgaa cagcgtgacc ccggaagata cggccgtgta ttattgcgcg     300
cgtggttgga ttactggttg gcgtattttt gattattggg gccaaggcac cctggtgacg     360
gttagctca                                                             369

<210> SEQ ID NO 316
<211> LENGTH: 360
<212> TYPE: DNA
<213> ORGANISM: Homo sapiens

<400> SEQUENCE: 316
caggtgcaat tggtggaaag cggcggcggc ctggtgcaac gggcggcag cctgcgtctg       60 agctgcgcgg cctccggatt tacctttttct acttatgcta tgtcttgggt gcgccaagcc    120
cctgggaagg gtctcgagtg ggtgagcttt atctctggtt atggtagctc tacctattat    180
gcggatagcg tgaaaggccg ttttaccatt tcacgtgata attcgaaaaa cacccctgtat   240 ctgcaaatga acagcctgcg tgcggaagat acggccgtgt attattgcgc gcgtaagatg     300
```

```
tattggtggt ctgatggttt tgattattgg ggccaaggca ccctggtgac ggttagctca    360

<210> SEQ ID NO 317
<211> LENGTH: 363
<212> TYPE: DNA
<213> ORGANISM: Homo sapiens

<400> SEQUENCE: 317
caggtgcaat tggtggaaag cggcggcggc ctggtgcaac cgggcggcag cctgcgtctg     60
agctgcgcgg cctccggatt tacctttttct cgttatgcta tttcttgggt gcgccaagcc   120
cctgggaagg gtctcgagtg ggtgagctct atctctggtg gtggtagcaa gaccttttat    180
gcggatagcg tgaaaggccg ttttaccatt tcacgtgata attcgaaaaa caccctgtat    240
ctgcaaatga acagcctgcg tgcggaagat acggccgtgt attattgcgc gcgttatcct    300
ggtcctactg gtcatgtttt ttttgatatt tggggccaag cacccctggt gacggttagc    360
tca                                                                  363

<210> SEQ ID NO 318
<211> LENGTH: 348
<212> TYPE: DNA
<213> ORGANISM: Homo sapiens

<400> SEQUENCE: 318
caggtgcaat tggttcagtc tggcgcggaa gtgaaaaaac cgggcagcag cgtgaaagtg     60
agctgcaaag cctccggagg cacttttttct tcttattata tttcttgggt gcgccaagcc   120
cctgggcagg gtctcgagtg gatgggcggt atcattccga agtttggcac tgcgaattac    180
gcgcagaagt tcagggccg ggtgaccatt accgcggatg aaagcaccag caccgcgtat     240
atggaactga gcagcctgcg tagcgaagat acggccgtgt attattgcgc gcgtactatt    300
ggtatttatg attcttgggg ccaaggcacc ctggtgacgg ttagctca                 348

<210> SEQ ID NO 319
<211> LENGTH: 345
<212> TYPE: DNA
<213> ORGANISM: Homo sapiens

<400> SEQUENCE: 319
caggtgcaat tggttcagtc tggcgcggaa gtgaaaaaac cgggcagcag cgtgaaagtg     60
agctgcaaag cctccggagg cacttttttct tctcatgcta tttcttgggt gcgccaagcc   120
cctgggcagg gtctcgagtg gatgggcaat atcatgccga tttttggcgt tgcgaattac    180
gcgcagaagt tcagggccg ggtgaccatt accgcggatg aaagcaccag caccgcgtat     240
atggaactga gcagcctgcg tagcgaagat acggccgtgt attattgcgc gcgtgagatg    300
cgtcttgctt attggggcca aggcacccctg gtgacggtta gctca                   345

<210> SEQ ID NO 320
<211> LENGTH: 378
<212> TYPE: DNA
<213> ORGANISM: Homo sapiens

<400> SEQUENCE: 320
caggtgcaat tgcaacagtc tggtccgggc ctggtgaaac cgagccaaac cctgagcctg     60
acctgtgcga tttccggaga tagcgtgagc tctaatactg ctgcttggtc ttggattcgc    120
cagtctcctg ggcgtggcct cgagtggctg ggccgtatcc gttatcgtag caagtggtat    180
```

```
aacgattatg cggtgagcgt gaaaagccgg attaccatca acccggatac ttcgaaaaac      240
cagtttagcc tgcaactgaa cagcgtgacc ccggaagata cggccgtgta ttattgcgcg      300
cgtggttatc atcagggtct ttatggtaat catatgtttg atgtttgggg ccaaggcacc      360
ctggtgacgg ttagctca                                                   378
```

<210> SEQ ID NO 321
<211> LENGTH: 354
<212> TYPE: DNA
<213> ORGANISM: Homo sapiens

<400> SEQUENCE: 321

```
caggtgcaat tgaaagaaag cggcccggcc ctggtgaaac cgacccaaac cctgaccctg       60
acctgtacct tttccggatt tagcctgtct tcttctggtg ttggtgtgtc ttggattcgc      120
cagccgcctg ggaaagccct cgagtggctg gctcttatcg attgggatga tgataagtct      180
tatagcacca gcctgaaaac gcgtctgacc attagcaaag atacttcgaa aaatcaggtg      240
gtgctgacta tgaccaacat ggacccggtg gatacggcca cctattattg cgcgcgtatt      300
cagggttgga attatgatgt ttggggccaa ggcaccctgg tgacggttag ctca            354
```

<210> SEQ ID NO 322
<211> LENGTH: 360
<212> TYPE: DNA
<213> ORGANISM: Homo sapiens

<400> SEQUENCE: 322

```
caggtgcaat tgcaacagtc tggtccgggc ctggtgaaac cgagccaaac cctgagcctg       60
acctgtgcga tttccggaga tagcgtgagc tcttcttctg ctgcttggtc ttggattcgc      120
cagtctcctg ggcgtggcct cgagtggctg ggccgtatcg gtcagcgtag caagtggtat      180
aacgattatg cggtgagcgt gaaaagccgg attaccatca acccggatac ttcgaaaaac      240
cagtttagcc tgcaactgaa cagcgtgacc ccggaagata cggccgtgta ttattgcgcg      300
cgttctcgtt ttggttattt tgatgtttgg ggccaaggca ccctggtgac ggttagctca      360
```

<210> SEQ ID NO 323
<211> LENGTH: 354
<212> TYPE: DNA
<213> ORGANISM: Homo sapiens

<400> SEQUENCE: 323

```
caggtgcaat tggtggaaag cggcggcggc ctggtgcaac cgggcggcag cctgcgtctg       60
agctgcgcgg cctccggatt tacctttctct tctcattatt cttgggtgcg ccaagcccct     120
gggaagggtc tcgagtgggt gagcactatc tcttctaatg gtagctatac ctattatgcg      180
gatagcgtga aaggccgttt taccatttca cgtgataatt cgaaaaacac cctgtatctg      240
caaatgaaca gcctgcgtgc ggaagatacg gccgtgtatt attgcgcgcg ttttgttgct      300
cgtcttaatg tttttgatta ttggggccaa ggcaccctgg tgacggttag ctca            354
```

<210> SEQ ID NO 324
<211> LENGTH: 345
<212> TYPE: DNA
<213> ORGANISM: Homo sapiens

<400> SEQUENCE: 324

```
caggtgcaat tggttcagtc tggcgcggaa gtgaaaaaac cgggcagcag cgtgaaagtg       60
agctgcaaag cctccggagg cacttttttct aattatacta tttcttgggt gcgccaagcc     120
```

```
cctgggcagg gtctcgagtg gatgggcaat atcattccgg cttttggcta tgcgaattac    180
gcgcagaagt tcagggccg ggtgaccatt accgcgatg aaagcaccag caccgcgtat      240
atggaactga gcagcctgcg tagcgaagat acggccgtgt attattgcgc gcgtaagttt   300
acttttgatg tttggggcca aggcaccctg gtgacggtta gctca                  345
```

<210> SEQ ID NO 325
<211> LENGTH: 354
<212> TYPE: DNA
<213> ORGANISM: Homo sapiens

<400> SEQUENCE: 325

```
caggtgcaat tggtggaaag cggcggcggc ctggtgcaac cgggcggcag cctgcgtctg    60
agctgcgcgg cctccggatt tacctttctc tcttattatt cttgggtgcg ccaagcccct    120
gggaagggtc tcgagtgggt gagcaatatc tctggtaatg gtagctctac ctattatgcg    180
gatagcgtga aaggccgttt taccatttca cgtgataatt cgaaaaacac cctgtatctg    240
caaatgaaca gcctgcgtgc ggaagatacg gccgtgtatt attgcgcgcg tcttattgct    300
actcttggta cttttgatta ttggggccaa ggcaccctgg tgacggttag ctca           354
```

<210> SEQ ID NO 326
<211> LENGTH: 360
<212> TYPE: DNA
<213> ORGANISM: Homo sapiens

<400> SEQUENCE: 326

```
caggtgcaat tggtggaaag cggcggcggc ctggtgcaac cgggcggcag cctgcgtctg    60
agctgcgcgg cctccggatt tacctttctc aattatggta ttcattgggt gcgccaagcc    120
cctgggaagg gtctcgagtg ggtgagctat atccgttctg gttctagcga taccta ttat    180 gcggatagcg tgaaaggccg ttttaccatt tcacgtgata attcgaaaaa accctgtat     240 ctgcaaatga acagcctgcg tgcggaagat acggccgtgt attattgcgc gcgtactgct    300
cctgctggtc atggtgttttt tgctaattgg ggccaaggca ccctggtgac ggttagctca   360
```

<210> SEQ ID NO 327
<211> LENGTH: 330
<212> TYPE: DNA
<213> ORGANISM: Homo sapiens

<400> SEQUENCE: 327

```
gatatcgtgc tgacccagag cccggcgacc ctgagcctgt ctccgggcga acgtgcgacc    60
ctgagctgca gagcgagcca gtctgttcgt tcttctcgtc tggcttggta ccagcagaaa    120
ccaggtcaag caccgcgtct attaatttat ggtgcttcta gcgtgcaac tggggtcccg    180 gcgcgtttta gcggctctgg atccggcacg gattttaccc tgaccattag cagcctggaa    240
cctgaagact tgcgactta ttattgccag cagtattatg attttcctcc tacctttggc    300
cagggtacga aagttgaaat taaacgtacg                                      330
```

<210> SEQ ID NO 328
<211> LENGTH: 333
<212> TYPE: DNA
<213> ORGANISM: Homo sapiens

<400> SEQUENCE: 328

```
gatatcgtgc tgacccagag cccggcgacc ctgagcctgt ctccgggcga acgtgcgacc    60
```

```
ctgagctgca gagcgagcca gtctgttcgt tcttctcgtc tggcttggta ccagcagaaa    120
ccaggtcaag caccgcgtct attaatttat ggtgcttcta agcgtgcaac tggggtcccg    180
gcgcgtttta gcggctctgg atccggcacg gattttaccc tgaccattag cagcctggaa    240
cctgaagact ttgcggtgta ttattgccag cagtattctc atgatccttc tggtaccttt    300
ggccagggta cgaaagttga aattaaacgt acg                                 333

<210> SEQ ID NO 329
<211> LENGTH: 330
<212> TYPE: DNA
<213> ORGANISM: Homo sapiens

<400> SEQUENCE: 329
gatatcgtgc tgacccagag cccggcgacc ctgagcctgt ctccgggcga acgtgcgacc     60
ctgagctgca gagcgagcca gtctgttcgt tcttctcgtc tggcttggta ccagcagaaa    120
ccaggtcaag caccgcgtct attaatttat ggtgcttcta agcgtgcaac tggggtcccg    180
gcgcgtttta gcggctctgg atccggcacg gattttaccc tgaccattag cagcctggaa    240
cctgaagact ttgcgactta ttattgccag cagtattatg attttcctcc tacctttggc    300
cagggtacga agttgaaat taaacgtacg                                      330

<210> SEQ ID NO 330
<211> LENGTH: 330
<212> TYPE: DNA
<213> ORGANISM: Homo sapiens

<400> SEQUENCE: 330
gatatcgtgc tgacccagag cccggcgacc ctgagcctgt ctccgggcga acgtgcgacc     60
ctgagctgca gagcgagcca gtctgttcgt tcttctcgtc tggcttggta ccagcagaaa    120
ccaggtcaag caccgcgtct attaatttat ggtgcttcta agcgtgcaac tggggtcccg    180
gcgcgtttta gcggctctgg atccggcacg gattttaccc tgaccattag cagcctggaa    240
cctgaagact ttgcgactta ttattgccag cagtattatg attttcctcc tacctttggc    300
cagggtacga agttgaaat taaacgtacg                                      330

<210> SEQ ID NO 331
<211> LENGTH: 330
<212> TYPE: DNA
<213> ORGANISM: Homo sapiens

<400> SEQUENCE: 331
gatatcgtgc tgacccagag cccggcgacc ctgagcctgt ctccgggcga acgtgcgacc     60
ctgagctgca gagcgagcca gtctgttcgt tcttctcgtc tggcttggta ccagcagaaa    120
ccaggtcaag caccgcgtct attaatttat ggtgcttcta agcgtgcaac tggggtcccg    180
gcgcgtttta gcggctctgg atccggcacg gattttaccc tgaccattag cagcctggaa    240
cctgaagact ttgcggtgta ttattgccag cagttttatt ctaagcctat tacctttggc    300
cagggtacga agttgaaat taaacgtacg                                      330

<210> SEQ ID NO 332
<211> LENGTH: 333
<212> TYPE: DNA
<213> ORGANISM: Homo sapiens

<400> SEQUENCE: 332
gatatcgtgc tgacccagag cccggcgacc ctgagcctgt ctccgggcga acgtgcgacc     60
```

```
ctgagctgca gagcgagcca gtctgttcgt tcttctcgtc tggcttggta ccagcagaaa    120
ccaggtcaag caccgcgtct attaatttat ggtgcttcta agcgtgcaac tggggtcccg    180
gcgcgtttta gcggctctgg atccggcacg gattttaccc tgaccattag cagcctggaa    240
cctgaagact ttgcggtgta ttattgccag cagtattctc atgatccttc tggtaccttt    300
ggccagggta cgaaagttga aattaaacgt acg                                 333

<210> SEQ ID NO 333
<211> LENGTH: 333
<212> TYPE: DNA
<213> ORGANISM: Homo sapiens

<400> SEQUENCE: 333
gatatcgtgc tgacccagag cccggcgacc ctgagcctgt ctccgggcga acgtgcgacc    60
ctgagctgca gagcgagcca gtctgttcgt tcttctcgtc tggcttggta ccagcagaaa    120
ccaggtcaag caccgcgtct attaatttat ggtgcttcta agcgtgcaac tggggtcccg    180
gcgcgtttta gcggctctgg atccggcacg gattttaccc tgaccattag cagcctggaa    240
cctgaagact ttgcggtgta ttattgccag cagtattctc aggatccttc ttctaccttt    300
ggccagggta cgaaagttga aattaaacgt acg                                 333

<210> SEQ ID NO 334
<211> LENGTH: 330
<212> TYPE: DNA
<213> ORGANISM: Homo sapiens

<400> SEQUENCE: 334
gatatcgtgc tgacccagag cccggcgacc ctgagcctgt ctccgggcga acgtgcgacc    60
ctgagctgca gagcgagcca gattgtttcc ggttatctgg cttggtacca gcagaaacca    120
ggtcaagcac cgcgtctatt aatttatggt gcttcttctc gtgcaactgg ggtcccggcg    180
cgttttagcg gctctggatc cggcacggat tttaccctga ccattagcag cctggaacct    240
gaagactttg cggtgtatta ttgccagcag tggtctcttc gttctccttt tacctttggc    300
cagggtacga aagttgaaat taaacgtacg                                     330

<210> SEQ ID NO 335
<211> LENGTH: 333
<212> TYPE: DNA
<213> ORGANISM: Homo sapiens

<400> SEQUENCE: 335
gatatcgtgc tgacccagcc gccttcagtg agtggcgcac caggtcagcg tgtgaccatc    60
tcgtgtagcg gcagcagcag caacattggt tctaattatg tgtcttggta ccagcagttg    120
cccgggacgg cgccgaaaac tctgatttat aatgataatc agcgtccctc aggcgtgccg    180
gatcgtttta gcggatccaa aagcggcacc agcgcgagcc ttgcgattac gggcctgcaa    240
agcgaagacg aagcggatta ttattgctct acttatgatc gtcgtacttt ttctgtgttt    300
ggcggcggca cgaagttaac cgtcctaggt cag                                 333

<210> SEQ ID NO 336
<211> LENGTH: 333
<212> TYPE: DNA
<213> ORGANISM: Homo sapiens

<400> SEQUENCE: 336
```

```
gatatcgtgc tgacccagcc gccttcagtg agtggcgcac caggtcagcg tgtgaccatc    60
tcgtgtagcg gcagcagcag caacattggt tctaattatg tgtcttggta ccagcagttg   120
cccgggacgg cgccgaaact tctgatttat aatgataatc agcgtccctc aggcgtgccg   180
gatcgtttta gcggatccaa aagcggcacc agcgcgagcc ttgcgattac gggcctgcaa   240
agcgaagacg aagcggatta ttattgctct acttatgatc gtcgtacttt ttctgtgttt   300
ggcggcggca cgaagttaac cgtcctaggt cag                                333

<210> SEQ ID NO 337
<211> LENGTH: 330
<212> TYPE: DNA
<213> ORGANISM: Homo sapiens

<400> SEQUENCE: 337
gatatcgtgc tgacccagag cccggcgacc ctgagcctgt ctccgggcga acgtgcgacc    60
ctgagctgca gcgagcca gtctgttcgt tcttctcgtc tggcttggta ccagcagaaa   120
ccaggtcaag caccgcgtct attaatttat ggtgcttcta agcgtgcaac tggggtcccg   180
gcgcgtttta gcggctctgg atccggcacg gattttaccc tgaccattag cagcctggaa   240
cctgaagact ttgcgactta ttattgccag cagtattatg attttcctcc tacctttggc   300
cagggtacga agttgaaat taaacgtacg                                    330

<210> SEQ ID NO 338
<211> LENGTH: 336
<212> TYPE: DNA
<213> ORGANISM: Homo sapiens

<400> SEQUENCE: 338
gatatcgtgc tgacccagcc gccttcagtg agtggcgcac caggtcagcg tgtgaccatc    60
tcgtgtagcg gcagcagcag caacattggt tctaattatg tgtcttggta ccagcagttg   120
cccgggacgg cgccgaaact tctgatttat aatgataatc agcgtccctc aggcgtgccg   180
gatcgtttta gcggatccaa aagcggcacc agcgcgagcc ttgcgattac gggcctgcaa   240
agcgaagacg aagcggatta ttattgctct tcttgggatc gtgctgatgg ttcttatgtg   300
tttggcggcg gcacgaagtt aaccgtccta ggtcag                             336

<210> SEQ ID NO 339
<211> LENGTH: 339
<212> TYPE: DNA
<213> ORGANISM: Homo sapiens

<400> SEQUENCE: 339
gatatcgcac tgacccagcc agcttcagtg agcggctcac caggtcagag cattaccatc    60
tcgtgtacgg gtactagcag cgatgttggt ggttataatt atgtgtcttg gtaccagcag   120
catcccggga aggcgccgaa acttatgatt tattctgttt ctaagcgtcc ctcaggcgtg   180
agcaaccgtt ttagcggatc caaaagcggc aacaccgcga gcctgaccat tagcggcctg   240
caagcggaag acgaagcgga ttattattgc ggtgcttggg ctcatatgtc tcttggtaag   300
gtgtttggcg gcggcacgaa gttaaccgtt cttggccag                          339

<210> SEQ ID NO 340
<211> LENGTH: 339
<212> TYPE: DNA
<213> ORGANISM: Homo sapiens

<400> SEQUENCE: 340
```

```
gatatcgcac tgacccagcc agcttcagtg agcggctcac caggtcagag cattaccatc    60
tcgtgtacgg gtactagcag cgatgttggt ggttataatt atgtgtcttg gtaccagcag   120
catcccggga aggcgccgaa acttatgatt tattctgttt ctaagcgtcc ctcaggcgtg   180
agcaaccgtt ttagcggatc caaaagcggc aacaccgcga gcctgaccat tagcggcctg   240
caagcggaag acgaagcgga ttattattgc gctacttggg atcattctca gatgggtaag   300
gtgtttggcg gcggcacgaa gttaaccgtc ctaggtcag                          339
```

<210> SEQ ID NO 341
<211> LENGTH: 339
<212> TYPE: DNA
<213> ORGANISM: Homo sapiens

<400> SEQUENCE: 341

```
gatatcgcac tgacccagcc agcttcagtg agcggctcac caggtcagag cattaccatc    60
tcgtgtacgg gtactagcag cgatgttggt ggttataatt atgtgtcttg gtaccagcag   120
catcccggga aggcgccgaa acttatgatt tattctgttt ctaagcgtcc ctcaggcgtg   180
agcaaccgtt ttagcggatc caaaagcggc aacaccgcga gcctgaccat tagcggcctg   240
caagcggaag acgaagcgga ttattattgc gctacttggg atcattctca gatgggtaag   300
gtgtttggcg gcggcacgaa gttaaccgtc ctaggtcag                          339
```

<210> SEQ ID NO 342
<211> LENGTH: 327
<212> TYPE: DNA
<213> ORGANISM: Homo sapiens

<400> SEQUENCE: 342

```
gatatcgtgc tgacccagag cccggcgacc ctgagcctgt ctccgggcga acgtgcgacc    60
ctgagctgca gcgagccca gattgtttcc ggttatctgg cttggtacca gcagaaacca   120
ggtcaagcac cgcgtctatt aatttatggt gcttcttctc gtgcaactgg ggtcccggcg   180
cgttttagcg gctctggatc cggcacggat tttaccctga ccattagcag cctggaacct   240
gaagactttg cgacttatta ttgccagcag tattataatt tttcttttac ctttggccag   300
ggtacgaaag ttgaaattaa acgtacg                                       327
```

<210> SEQ ID NO 343
<211> LENGTH: 327
<212> TYPE: DNA
<213> ORGANISM: Homo sapiens

<400> SEQUENCE: 343

```
gatatccaga tgacccagag cccgtctagc ctgagcgcga gcgtgggtga tcgtgtgacc    60
attacctgca gcgcagcca gaatattggt tcttatctga attggtacca gcagaaacca   120
ggtaaagcac cgaaactatt aatttataat tcttctactt tgcaaagcgg ggtcccgtcc   180
cgttttagcg gctctggatc cggcactgat tttaccctga ccattagcag cctgcaacct   240
gaagactttg cgacttatta ttgccagcag cgttctaata tgcctattac ctttggccag   300
ggtacgaaag ttgaaattaa acgtacg                                       327
```

<210> SEQ ID NO 344
<211> LENGTH: 333
<212> TYPE: DNA
<213> ORGANISM: Homo sapiens

```
<400> SEQUENCE: 344
gatatcgcac tgacccagcc agcttcagtg agtggcgcac caggtcagcg tgtgaccatc    60
tcgtgtacgg gtactagcag cgatgttggt gcttctgata ctgtgacttg gtaccagcag   120
catcccggga aggcgccgaa acttatgatt tatgctgtta ataagcgtcc ctcaggcgtg   180
agcaaccgtt ttagcggatc caaaagcggc aacaccgcga gcctgaccat tagcggcctg   240
caagcggaag acgaagcgga ttattattgc gcttctcgtg attcttcttc tatggtgttt   300
ggcggcggca cgaagttaac cgttcttggc cag                                333

<210> SEQ ID NO 345
<211> LENGTH: 342
<212> TYPE: DNA
<213> ORGANISM: Homo sapiens

<400> SEQUENCE: 345
gatatcgtga tgacccagag cccactgagc ctgccagtga ctccgggcga gcctgcgagc    60
attagctgca gaagcagcca aagcctgctt cattctaatg gctatactta tctgtcttgg   120
taccttcaaa aaccaggtca agcccgcag ctattaattt atcttggttc taagcgtgcc   180
agtggggtcc cggatcgttt tagcggctct ggatccggca ccgattttac cctgaaaatt   240
agccgtgtgg aagctgaaga cgtgggcgtg tattattgcc agcagtatta tgattcttct   300
tctacctttg gccagggtac gaaagttgaa attaaacgta cg                     342

<210> SEQ ID NO 346
<211> LENGTH: 336
<212> TYPE: DNA
<213> ORGANISM: Homo sapiens

<400> SEQUENCE: 346
gatatcgtgc tgacccagcc gccttcagtg agtggcgcac caggtcagcg tgtgaccatc    60
tcgtgtagcg gcagcagcag caacattggt cctaattatg tgtcttggta ccagcagttg   120
cccgggacgg cgccgaaact tctgattcat ggtaatgcta atcgtccctc aggcgtgccg   180
gatcgtttta gcggatccaa aagcggcacc agcgcgagcc ttgcgattac gggcctgcaa   240
agcgaagacg aagcggatta ttattgccag tcttatgatt ttttactaa ttcttctgtg   300 tttggcggcg gcacgaagtt aaccgttctt ggccag                             336

<210> SEQ ID NO 347
<211> LENGTH: 330
<212> TYPE: DNA
<213> ORGANISM: Homo sapiens

<400> SEQUENCE: 347
gatatcgtgc tgacccagag cccggcgacc ctgagcctgt ctccgggcga acgtgcgacc    60
ctgagctgca gagcgagcca gtctcttact tctaatcagc tggcttggta ccagcagaaa   120
ccaggtcaag caccgcgtct attaattat gattcttcta tcgtgcaac tggggtcccg   180 gcgcgtttta gcggctctgg atccggcacg gattttaccc tgaccattag cagcctggaa   240
cctgaagact ttgcggttta ttattgccag cagtatggtt cttttcctgc tacctttggc   300
cagggtacga aagttgaaat taaacgtacg                                    330

<210> SEQ ID NO 348
<211> LENGTH: 339
<212> TYPE: DNA
<213> ORGANISM: Homo sapiens
```

<400> SEQUENCE: 348

```
gatatcgcac tgacccagcc agcttcagtg agcggctcac caggtcagag cattaccatc    60
tcgtgtacgg gtactagcag cgatgttggt ggtaataatt ttgtgtcttg gtaccagcag   120
catcccggga aggcgccgaa acttatgatt tattatggtg attctcgtcc ctcaggcgtg   180
agcaaccgtt ttagcggatc caaaagcggc aacaccgcga gcctgaccat tagcggcctg   240
caagcggaag acgaagcgga ttattattgc cagtcttggg atgctcctat gggtatgtgg   300
gtgtttggcg gcggcacgaa gttaaccgtt cttggccag                          339
```

<210> SEQ ID NO 349
<211> LENGTH: 339
<212> TYPE: DNA
<213> ORGANISM: Homo sapiens

<400> SEQUENCE: 349

```
gatatcgcac tgacccagcc agcttcagtg agcggctcac caggtcagag cattaccatc    60
tcgtgtacgg gtactagcag cgatgttggt ggtaataatt ttgtgtcttg gtaccagcag   120
catcccggga aggcgccgaa acttatgatt tattatggtg attctcgtcc ctcaggcgtg   180
agcaaccgtt ttagcggatc caaaagcggc aacaccgcga gcctgaccat tagcggcctg   240
caagcggaag acgaagcgga ttattattgc cagtcttggg atgctcctat gggtatgtgg   300
gtgtttggcg gcggcacgaa gttaaccgtt cttggccag                          339
```

<210> SEQ ID NO 350
<211> LENGTH: 336
<212> TYPE: DNA
<213> ORGANISM: Homo sapiens

<400> SEQUENCE: 350

```
gatatcgcac tgacccagcc agcttcagtg agcggctcac caggtcagag cattaccatc    60
tcgtgtacgg gtactagcag cgatgttggt aattttaatt atgtgaattg gtaccagcag   120
catcccggga aggcgccgaa acttatgatt tattctgttt cttctcgtcc ctcaggcgtg   180
agcaaccgtt ttagcggatc caaaagcggc aacaccgcga gcctgaccat tagcggcctg   240
caagcggaag acgaagcgga ttattattgc ggtgcttata ctactgatac tctttctgtg   300
tttggcggcg gcacgaagtt aaccgttctt ggccag                             336
```

<210> SEQ ID NO 351
<211> LENGTH: 330
<212> TYPE: DNA
<213> ORGANISM: Homo sapiens

<400> SEQUENCE: 351

```
gatatcgtgc tgacccagag cccggcgacc ctgagcctgt ctccgggcga acgtgcgacc    60
ctgagctgca gagcgagcca gtctgttact tctaattatc tggcttggta ccagcagaaa   120
ccaggtcaag caccgcgtct attaatttat ggttcttctt ctcgtgcaac tggggtcccg   180
gcgcgtttta gcggctctgg atccggcacg gatttacccc tgaccattag cagcctggaa   240
cctgaagact ttgcggttta ttattgccag cagtattctg atattcctgc tacctttggc   300
cagggtacga agttgaaat  taaacgtacg                                    330
```

<210> SEQ ID NO 352
<211> LENGTH: 327
<212> TYPE: DNA

<213> ORGANISM: Homo sapiens

<400> SEQUENCE: 352

| gatatccaga tgacccagag cccgtctagc ctgagcgcga gcgtgggtga tcgtgtgacc | 60 |
| attacctgca gagcgagcca gtctattaat cgttctctga cttggtacca gcagaaacca | 120 |
| ggtaaagcac cgaaactatt aatttatgct gcttctaatt tgcaaagcgg ggtcccgtcc | 180 |
| cgttttagcg gctctggatc cggcactgat tttacccctg accattagca gcctgcaacct | 240 |
| gaagactttg cggttttatta ttgccttcag gtttataatc ttcctcttac ctttggccag | 300 |
| ggtacgaaag ttgaaattaa acgtacg | 327 |

<210> SEQ ID NO 353
<211> LENGTH: 339
<212> TYPE: DNA
<213> ORGANISM: Homo sapiens

<400> SEQUENCE: 353

| gatatcgcac tgacccagcc agcttcagtg agcggctcac caggtcagag cattaccatc | 60 |
| tcgtgtacgg gtactagcag cgatattggt ggttttaatt atgtgtcttg gtaccagcag | 120 |
| catccccggga aggcgccgaa acttatgatt tatgatgttt ctaatcgtcc ctcaggcgtg | 180 |
| agcaaccgtt ttagcggatc caaaagcggc aacaccgcga gcctgaccat tagcggcctg | 240 |
| caagcggaag acgaagcgga ttattattgc tctacttatg atgatgatca gcaggatgct | 300 |
| gtgtttggcg gcggcacgaa gttaaccgtt cttggccag | 339 |

<210> SEQ ID NO 354
<211> LENGTH: 330
<212> TYPE: DNA
<213> ORGANISM: Homo sapiens

<400> SEQUENCE: 354

| gatatcgaac tgacccagcc gccttcagtg agcgttgcac caggtcagac cgcgcgtatc | 60 |
| tcgtgtagcg gcgataatat tcctaatttt tatgttcatt ggtaccagca gaaacccggg | 120 |
| caggcgccat tcttgtgat ttatgaggat tctgatcgtc cctcaggcat cccggaacgc | 180 |
| tttagcggat ccaacagcgg caacaccgcg accctgacca ttagcggcac tcaggcggaa | 240 |
| gacgaagcgg attattattg ccagtcttat gataagccta cttttttctgg tgtgtttggc | 300 |
| ggcggcacga agttaaccgt tcttggccag | 330 |

<210> SEQ ID NO 355
<211> LENGTH: 339
<212> TYPE: DNA
<213> ORGANISM: Homo sapiens

<400> SEQUENCE: 355

| gatatcgcac tgacccagcc agcttcagtg agcggctcac caggtcagag cattaccatc | 60 |
| tcgtgtacgg gtactagcag cgatattggt cgttatcatt atgtgtcttg gtaccagcag | 120 |
| catcccggga aggcgccgaa agttatgatt tattctgttt ctaagcgtcc ctcaggcgtg | 180 |
| agcaaccgtt ttagcggatc caaaagcggc aacaccgcga gcctgaccat tagcggcctg | 240 |
| caagcggaag acgaagcgga ttattattgc tctgcttatg atactaataa ttatctttct | 300 |
| gtgtttggcg gcggcacgaa gttaaccgtt cttggccag | 339 |

<210> SEQ ID NO 356
<211> LENGTH: 324

```
<212> TYPE: DNA
<213> ORGANISM: Homo sapiens

<400> SEQUENCE: 356
gatatcgtgc tgacccagcc gccttcagtg agtggcgcac caggtcagcg tgtgaccatc      60
tcgtgtagcg gcagcagcag caacattggt aataattctg tgaattggta ccagcagttg     120
cccgggacgg cgccgaaact tctgatttat aataatcagc gtccctcagg cgtgccggat     180
cgttttagcg gatccaaaag cggcaccagc gcgagccttg cgattacggg cctgcaaagc     240
gaagacgaag cggattatta ttgccaggct tatgcttcta atattgtgtt tggcggcggc     300
acgaagttaa ccgttcttgg ccag                                            324

<210> SEQ ID NO 357
<211> LENGTH: 333
<212> TYPE: DNA
<213> ORGANISM: Homo sapiens

<400> SEQUENCE: 357
gatatcgcac tgacccagcc agcttcagtg agcggctcac caggtcagag cattaccatc      60
tcgtgtacgg gtactagcag cgatgttggt gattataatt atgtgtcttg gtaccagcag     120
catcccggga aggcgccgaa acttatgatt tatcgtgttg ataatcgtcc ctcaggcgtg     180
agcaaccgtt ttagcggatc caaaagcggc aacaccgcga gcctgaccat tagcggcctg     240
caagcggaag acgaagcgga ttattattgc cagtcttggg ttggtccttc tactgtgttt     300
ggcggcggca cgaagttaac cgttcttggc cag                                  333

<210> SEQ ID NO 358
<211> LENGTH: 333
<212> TYPE: DNA
<213> ORGANISM: Homo sapiens

<400> SEQUENCE: 358
gatatcgtgc tgacccagcc gccttcagtg agtggcgcac caggtcagcg tgtgaccatc      60
tcgtgtagcg gcagcagcag caacattggt aataattatg tgtcttggta ccagcagttg     120
cccgggacgg cgccgaaact tctgatttat tctaattctc agcgtccctc aggcgtgccg     180
gatcgtttta gcggatccaa aagcggcacc agcgcgagcc ttgcgattac gggcctgcaa     240
agcgaagacg aagcggatta ttattgccag tcttatgatc ataattctta tactgtgttt     300
ggcggcggca cgaagttaac cgttcttggc cag                                  333

<210> SEQ ID NO 359
<211> LENGTH: 324
<212> TYPE: DNA
<213> ORGANISM: Homo sapiens

<400> SEQUENCE: 359
gatatcgaac tgacccagcc gccttcagtg agcgttgcac caggtcagac cgcgcgtatc      60
tcgtgtagcg gcgataatct tcgttctaag tatgctcatt ggtaccagca gaaacccggg     120
caggcgccag ttcttgtgat ttattctaag gataatcgtc cctcaggcat cccggaacgc     180
tttagcggat ccaacagcgg caacaccgcg accctgacca ttagcggcac tcaggcggaa     240
gacgaagcgg attattattg ctcttcttgg gctcatgatc ataaggtgtt tggcggcggc     300
acgaagttaa ccgttcttgg ccag                                            324

<210> SEQ ID NO 360
```

-continued

```
<211> LENGTH: 330
<212> TYPE: DNA
<213> ORGANISM: Homo sapiens

<400> SEQUENCE: 360
gatatcgaac tgacccagcc gccttcagtg agcgttgcac caggtcagac cgcgcgtatc      60
tcgtgtagcg gcgataatat tggttctaag gttgctactt ggtaccagca gaaacccggg     120
caggcgccag ttcttgtgat ttattatgat aatgatcgtc cctcaggcat cccggaacgc     180
tttagcggat ccaacagcgg caacaccgcg accctgacca ttagcggcac tcaggcggaa     240
gacgaagcgg attattattg ccagtcttat gatggtcaga tgtctacttc tgtgtttggc     300
ggcggcacga agttaaccgt tcttggccag                                      330

<210> SEQ ID NO 361
<211> LENGTH: 339
<212> TYPE: DNA
<213> ORGANISM: Homo sapiens

<400> SEQUENCE: 361
gatatcgcac tgacccagcc agcttcagtg agcggctcac caggtcagag cattaccatc      60
tcgtgtacgg gtactagcag cgatgttggt ggttataatt atgtgtcttg gtaccagcag     120
catcccggga aggcgccgaa acttatgatt tattctgtta ataatcgtcc ctcaggcgtg     180
agcaaccgtt ttagcggatc caaaagcggc aacaccgcga gcctgaccat tagcggcctg     240
caagcggaag acgaagcgga ttattattgc tctacttatg atcatacttc ttctggtttt     300
gtgtttggcg gcggcacgaa gttaaccgtt cttggccag                             339

<210> SEQ ID NO 362
<211> LENGTH: 333
<212> TYPE: DNA
<213> ORGANISM: Homo sapiens

<400> SEQUENCE: 362
gatatcgcac tgacccagcc agcttcagtg agcggctcac caggtcagag cattaccatc      60
tcgtgtacgg gtactagcag cgatattggt cattttaatt atgtgtcttg gtaccagcag     120
catcccggga aggcgccgaa acttatgatt tattctgtta tttctcgtcc ctcaggcgtg     180
agcaaccgtt ttagcggatc caaaagcggc aacaccgcga gcctgaccat tagcggcctg     240
caagcggaag acgaagcgga ttattattgc gcttctttta cttttccttc tcttgtgttt     300
ggcggcggca cgaagttaac cgttcttggc cag                                   333

<210> SEQ ID NO 363
<211> LENGTH: 336
<212> TYPE: DNA
<213> ORGANISM: Homo sapiens

<400> SEQUENCE: 363
gatatcgtgc tgacccagcc gccttcagtg agtggcgcac caggtcagcg tgtgaccatc      60
tcgtgtagcg gcagcagcag caacattggt tctcatactg tgaattggta ccagcagttg     120
cccgggacgg cgccgaaact tctgatttat gatgttaata gcgtccctc aggcgtgccg      180 gatcgtttta gcggatccaa aagcggcacc agcgcgagcc ttgcgattac gggcctgcaa     240
agcgaagacg aagcggatta ttattgcgct tctgggatt ctgttcaggt ttctcctgtg      300
tttggcggcg gcacgaagtt aaccgttctt ggccag                                336
```

<210> SEQ ID NO 364
<211> LENGTH: 333
<212> TYPE: DNA
<213> ORGANISM: Homo sapiens

<400> SEQUENCE: 364

```
gatatcgtgc tgacccagcc gccttcagtg agtggcgcac caggtcagcg tgtgaccatc     60
tcgtgtagcg gcagcagcag caacattggt aataatcgtg tgtcttggta ccagcagttg    120
cccgggacgg cgccgaaact tctgatttat ggtaataata agcgtccctc aggcgtgccg    180
gatcgtttta gcggatccaa agcggcacc agcgcgagcc ttgcgattac gggcctgcaa    240
agcgaagacg aagcggatta ttattgctct gcttgggatc ttcttgaggt ttatgtgttt    300
ggcggcggca cgaagttaac cgttcttggc cag                                  333
```

<210> SEQ ID NO 365
<211> LENGTH: 333
<212> TYPE: DNA
<213> ORGANISM: Homo sapiens

<400> SEQUENCE: 365

```
gatatcgcac tgacccagcc agcttcagtg agcggctcac caggtcagag cattaccatc     60
tcgtgtacgg gtactagcag cgatattggt acttataatc atgtgtcttg gtaccagcag    120
catcccggga aggcgccgaa acttatgatt tataatgtta ataagcgtcc ctcaggcgtg    180
agcaaccgtt ttagcggatc caaaagcggc aacaccgcga gcctgaccat tagcggcctg    240
caagcggaag acgaagcgga ttattattgc tctgcttatg ctccttctgc tgttgtgttt    300
ggcggcggca cgaagttaac cgttcttggc cag                                  333
```

<210> SEQ ID NO 366
<211> LENGTH: 339
<212> TYPE: DNA
<213> ORGANISM: Homo sapiens

<400> SEQUENCE: 366

```
gatatcgtgc tgacccagcc gccttcagtg agtggcgcac caggtcagcg tgtgaccatc     60
tcgtgtacgg gcagcagcag caacattggt attggttatg atgtgaattg gtaccagcag    120
ttgcccggga cggcgccgaa acttctgatt tataagaata ctaatcgtcc ctcaggcgtg    180
ccggatcgtt ttagcggatc caaaagcggc accagcgcga ccttgcgat acgggcctg     240
caaagcgaag acgaagcgga ttattattgc tcttcttatg attcttttca tcatggtatt    300
gtgtttggcg gcggcacgaa gttaaccgtt cttggccag                            339
```

<210> SEQ ID NO 367
<211> LENGTH: 339
<212> TYPE: DNA
<213> ORGANISM: Homo sapiens

<400> SEQUENCE: 367

```
gatatcgcac tgacccagcc agcttcagtg agcggctcac caggtcagag cattaccatc     60
tcgtgtacgg gtactagcag cgatcttggt ggttattctt atgtgtcttg gtaccagcag    120
catcccggga aggcgccgaa acttatgatt tataatgtta ataatcgtcc ctcaggcgtg    180
agcaaccgtt ttagcggatc caaaagcggc aacaccgcga gcctgaccat tagcggcctg    240
caagcggaag acgaagcgga ttattattgc tcttcttatg attatgtttc ttctgatact    300
gtgtttggcg gcggcacgaa gttaaccgtt cttggccag                            339
```

<210> SEQ ID NO 368
<211> LENGTH: 339
<212> TYPE: DNA
<213> ORGANISM: Homo sapiens

<400> SEQUENCE: 368

```
gatatcgcac tgacccagcc agcttcagtg agcggctcac caggtcagag cattaccatc      60
tcgtgtacgg gtactagcag cgatgttggt ggttataatt atgtgtcttg gtaccagcag     120
catcccggga aggcgccgaa agttatgatt tatggtgtta ctaagcgtcc ctcaggcgtg     180
agcaaccgtt ttagcggatc caaaagcggc aacaccgcga gcctgaccat tagcggcctg     240
caagcggaag acgaagcgga ttattattgc cagacttatg atgagcatgg ttttcatatt     300
gtgtttggcg gcggcacgaa gttaaccgtt cttggccag                            339
```

<210> SEQ ID NO 369
<211> LENGTH: 336
<212> TYPE: DNA
<213> ORGANISM: Homo sapiens

<400> SEQUENCE: 369

```
gatatcgtgc tgacccagcc gccttcagtg agtggcgcac caggtcagcg tgtgaccatc      60
tcgtgtagcg gcagcagcag caacattggt aattatcgtg tgtcttggta ccagcagttg     120
cccgggacgg cgccgaaact tctgatttat ggtaataata gcgtccctc aggcgtgccg      180
gatcgtttta gcggatccaa aagcggcacc agcgcgagcc ttgcgattac gggcctgcaa     240
agcgaagacg aagcggatta ttattgctct acttatactg tcttcctttt tactactgtg     300
tttggcggcg gcacgaagtt aaccgttctt ggccag                               336
```

<210> SEQ ID NO 370
<211> LENGTH: 327
<212> TYPE: PRT
<213> ORGANISM: Homo sapiens

<400> SEQUENCE: 370

```
Glu Val Glu Lys Thr Ala Cys Pro Ser Gly Lys Lys Ala Arg Glu Ile
1               5                   10                  15

Asp Glu Ser Leu Ile Phe Tyr Lys Lys Trp Glu Leu Glu Ala Cys Val
            20                  25                  30

Asp Ala Ala Leu Leu Ala Thr Gln Met Asp Arg Val Asn Ala Ile Pro
        35                  40                  45

Phe Thr Tyr Glu Gln Leu Asp Val Leu Lys His Lys Leu Asp Glu Leu
    50                  55                  60

Tyr Pro Gln Gly Tyr Pro Glu Ser Val Ile Gln His Leu Gly Tyr Leu
65                  70                  75                  80

Phe Leu Lys Met Ser Pro Glu Asp Ile Arg Lys Trp Asn Val Thr Ser
                85                  90                  95

Leu Glu Thr Leu Lys Ala Leu Leu Glu Val Asn Lys Gly His Glu Met
            100                 105                 110

Ser Pro Gln Val Ala Thr Leu Ile Asp Arg Phe Val Lys Gly Arg Gly
        115                 120                 125

Gln Leu Asp Lys Asp Thr Leu Asp Thr Leu Thr Ala Phe Tyr Pro Gly
    130                 135                 140

Tyr Leu Cys Ser Leu Ser Pro Glu Glu Leu Ser Ser Val Pro Pro Ser
145                 150                 155                 160

Ser Ile Trp Ala Val Arg Pro Gln Asp Leu Asp Thr Cys Asp Pro Arg
```

```
                          165                 170                 175
        Gln Leu Asp Val Leu Tyr Pro Lys Ala Arg Leu Ala Phe Gln Asn Met
                        180                 185                 190

Asn Gly Ser Glu Tyr Phe Val Lys Ile Gln Ser Phe Leu Gly Gly Ala
                    195                 200                 205

Pro Thr Glu Asp Leu Lys Ala Leu Ser Gln Gln Asn Val Ser Met Asp
                210                 215                 220

Leu Ala Thr Phe Met Lys Leu Arg Thr Asp Ala Val Leu Pro Leu Thr
        225                 230                 235                 240

Val Ala Glu Val Gln Lys Leu Leu Gly Pro His Val Glu Gly Leu Lys
                        245                 250                 255

Ala Glu Glu Arg His Arg Pro Val Arg Asp Trp Ile Leu Arg Gln Arg
                    260                 265                 270

Gln Asp Asp Leu Asp Thr Leu Gly Leu Gly Leu Gln Gly Gly Ile Pro
                275                 280                 285

Asn Gly Tyr Leu Val Leu Asp Leu Ser Met Gln Glu Ala Leu Ser Gly
            290                 295                 300

Thr Pro Cys Leu Leu Gly Pro Gly Pro Val Leu Thr Val Leu Ala Leu
        305                 310                 315                 320

Leu Leu Ala Ser Thr Leu Ala
                        325

<210> SEQ ID NO 371
<211> LENGTH: 340
<212> TYPE: PRT
<213> ORGANISM: Homo sapiens

<400> SEQUENCE: 371

Gly Gly Ser Ser Thr Ile Leu Arg Pro Arg Phe Arg Arg Glu Val Glu
        1               5                   10                  15

Lys Thr Ala Cys Pro Ser Gly Lys Lys Ala Arg Glu Ile Asp Glu Ser
                        20                  25                  30

Leu Ile Phe Tyr Lys Lys Trp Glu Leu Glu Ala Cys Val Asp Ala Ala
                    35                  40                  45

Leu Leu Ala Thr Gln Met Asp Arg Val Asn Ala Ile Pro Phe Thr Tyr
                50                  55                  60

Glu Gln Leu Asp Val Leu Lys His Lys Leu Asp Glu Leu Tyr Pro Gln
        65                  70                  75                  80

Gly Tyr Pro Glu Ser Val Ile Gln His Leu Gly Tyr Leu Phe Leu Lys
                        85                  90                  95

Met Ser Pro Glu Asp Ile Arg Lys Trp Asn Val Thr Ser Leu Glu Thr
                    100                 105                 110

Leu Lys Ala Leu Leu Glu Val Asn Lys Gly His Glu Met Ser Pro Gln
                115                 120                 125

Val Ala Thr Leu Ile Asp Arg Phe Val Lys Gly Arg Gly Gln Leu Asp
        130                 135                 140

Lys Asp Thr Leu Asp Thr Leu Thr Ala Phe Tyr Pro Gly Tyr Leu Cys
        145                 150                 155                 160

Ser Leu Ser Pro Glu Glu Leu Ser Ser Val Pro Pro Ser Ser Ile Trp
                        165                 170                 175

Ala Val Arg Pro Gln Asp Leu Asp Thr Cys Asp Pro Arg Gln Leu Asp
                    180                 185                 190

Val Leu Tyr Pro Lys Ala Arg Leu Ala Phe Gln Asn Met Asn Gly Ser
                195                 200                 205
```

-continued

```
Glu Tyr Phe Val Lys Ile Gln Ser Phe Leu Gly Gly Ala Pro Thr Glu
    210             215             220

Asp Leu Lys Ala Leu Ser Gln Gln Asn Val Ser Met Asp Leu Ala Thr
225             230             235             240

Phe Met Lys Leu Arg Thr Asp Ala Val Leu Pro Leu Thr Val Ala Glu
            245             250             255

Val Gln Lys Leu Leu Gly Pro His Val Glu Gly Leu Lys Ala Glu Glu
            260             265             270

Arg His Arg Pro Val Arg Asp Trp Ile Leu Arg Gln Arg Gln Asp Asp
        275             280             285

Leu Asp Thr Leu Gly Leu Gly Leu Gln Gly Gly Ile Pro Asn Gly Tyr
    290             295             300

Leu Val Leu Asp Leu Ser Val Gln Glu Ala Leu Ser Gly Thr Pro Cys
305             310             315             320

Leu Leu Gly Pro Gly Pro Val Leu Thr Val Leu Ala Leu Leu Leu Ala
            325             330             335

Ser Thr Leu Ala
            340
```

US 9,023,351 B2

ANTI-MESOTHELIN ANTIBODIES AND USES THEREOF

The present invention provides recombinant antigen-binding regions and antibodies and functional fragments containing such antigen-binding regions that are specific for the membrane-anchored, 40 kDa mesothelin polypeptide, which which is overexpressed in several tumors, such as pancreatic and ovarian tumors, mesothelioma and lung cancer cells. These antibodies, accordingly, can be used to treat these and other disorders and conditions. Antibodies of the invention also can be used in the diagnostics field, as well as for further investigating the role of mesothelin in the progression of disorders associated with cancer. The invention also provides nucleic acid sequences encoding the foregoing antibodies, vectors containing the same, pharmaceutical compositions and kits with instructions for use.

BACKGROUND OF THE INVENTION

Antibody-based therapy is proving very effective in the treatment of various cancers, including solid tumors. For example, HERCEPTIN® has been used successfully to treat breast cancer. Central to the development of a successful antibody-based therapy is isolation of antibodies against cell-surface proteins found to be preferentially expressed on tumor cells. The mesothelin precursor polypeptide is a glycophosphatidylinositol (GPI)-anchored, glycosylated cell surface protein that is proteolytically cleaved to a 30 kDa N-terminal secreted polypeptide and a 40 kDa, C-terminal polypeptide, which predominantly occurs in the membrane-bound, GPI-anchored form (Chang, K. and I. Pastan, Proc. Natl. Acad. Sci. USA, (1996) 93(1):136), and which is named mesothelin herein. Mesothelin is preferentially expressed by certain tumor cells, particularly mesothelioma cells, pancreatic tumor cells and ovarian carcinoma cells, while its expression is limited in normal tissue, making it an ideal target for tumor therapy (Argani, P. et al., Clin. Cancer Res. (2001) 7(12): 3862; Hassan, R., et al., Clin. Cancer Res. (2004) 10(12 Pt 1):3937). The function of mesothelin is unknown, and no apparent reproductive, hematologic, or anatomic abnormalities were observed in mice deficient in mesothelin gene expression (Bera, T. K. and I. Pastan, Mol. Cell. Biol. (2000) 20(8):2902).

Antibody-based, targeted therapy against mesothelin-expressing cancer cells has been proposed for the treatment of lung, ovarian and pancreatic cancer. Mab K1 was the first antibody to membrane-bound mesothelin polypeptide which was described (Chang, K., et al., Int. J. Cancer, (1992) 50(3): 373). Mab K1 was generated by immunizing mice. Due to low affinity and poor internalization rates of the antibody, an immunotoxin consisting of Mab K1 linked to a chemically modified truncated form of *Pseudomonas* exotoxin A was not considered suitable for clinical development (Hassan, R., et al., J. Immunother. (2000) 23(4):473; Hassan, R., et al., Clin. Cancer Res. (2004) 10(12 Pt 1): 3937). Subsequently, single-chain antibodies with higher affinities were developed, including SS1-(dsFv)-PE38, which showed killing activity of tumor cells in vitro (Hassan, R., et al., Clin. Cancer Res. (2002) 8(11): 3520) as well as potency in a murine model of human mesothelin-expressing tumors (Fan, D., et al., Mol. Cancer. Ther. (2002) 1(8): 595). These data validate mesothelin as a suitable target for immunotherapy of multiple cancers. However, in clinical trials, SS1-(dsFv)-PE38 was immunogenic, preventing a second administration for the majority of patients. Furthermore, SS1-(dsFv)-PE38 has been shown to have a fast blood clearance and attempts are being reported to increase the molecular weight by pegylating the fusion protein (Filpula, D., et al., Bioconjugate Chem. (2007) 18(3): 773).

MS-1, MS-2 and MS-3 are mesothelin-binding antibodies which elicit immune effector activity at the cell surface due to their human IgG1 isotype and internalize into mesothelin expressing cells (WO 2006/099141 A2). One of these antibodies, the unconjugated IgG anti-mesothelin antibody MOR Ab 009 is currently being tested in a clinical trial for therapeutic effects in the treatment of pancreatic cancer.

The predictive value of xenograft murine cancer models for clinical outcome of immunotoxin cancer therapy is often limited by a lack of cross-reactivity of the therapeutic antibodies with their murine homologues, which leads to reduced unspecific binding to normal tissue. On the other hand, neutralizing anti-mouse Fv antibodies which are formed in patients being treated with murine or chimeric antibodies may result in either dose-limiting toxicity or diminished therapeutic potency. Thus, to fully exploit the potential of specific mesothelin expression in cancer therapy, targeting antibodies are required which combine the advantages of increased affinities and reduced dissociation rates with a fully human variable chain format, and with murine cross-reactivity.

A further necessary feature of novel antibodies is invariant affinity to different cancer cell lines expressing mesothelin on their surface. Mesothelin is a highly variable protein, undergoing post-translational proteolytic digestion as well as glycosylation at multiple sites (Hassan, R., et al., Clin. Cancer Res. (2004) 10(12 Pt 1): 3937). Variability extends to the transcriptional level, since three different splice variants have been detected, although transcript variant 1 (NM_005823) seems to represent the major species present in tumor cell lines tested so far (Muminova, Z. E., et al., BMC Cancer (2004) 4:19; Hellstrom, I., et al., Cancer Epidemiol. Biomarkers Prev. (2006) 15(5):1014). Thus, effective anti-mesothelin antibodies must bind to an epitope invariantly presented by tumor cells from different patients, independently of individual variance including, but not restricted to, variances in glycosylation patterns, which leads to the expression of different forms of mesothelin.

Provided herein are antibodies, antigen-binding antibody fragments thereof, or variants thereof, that bind to mesothelin with high and invariant affinity, internalize efficiently, and that are preferably cross-reactive to mesothelin from another species. Also provided are antibody-based therapies for cancer, in particular for mesothelin expressing tumors, for example pancreatic, ovarian, or lung cancer, using antibodies, antigen-binding antibody fragments thereof, or variants thereof, that facilitate delivery of therapeutically active agents to cancer cells.

SUMMARY OF THE INVENTION

It is an object of the invention to provide human and humanized antibodies, or antigen-binding antibody fragments thereof, or variants thereof, that are highly selective for the 40 kDa, C-terminal extracellular part of the mesothelin precursor polypeptide, and which may be employed in methods for detection of mesothelin expression, which is associated with disease states such as cancer of the pancreas, ovary, and lung, and in the treatment of such disease states. Toward these ends, it is an object of the invention to provide isolated human antibodies, or antigen binding antibody fragments thereof, that specifically bind to an epitope present in the mesothelin polypeptide (SEQ ID NO:370), which is invariantly presented by mesothelin-expressing cancer cell lines, and which is bound by these antibodies with comparable affinities. As used herein, the term 'invariant presentation' of the epitope refers to the presence of an epitope recognized by a particular antibody on a broad range of mesothelin expressing tumor cell lines which express different forms of mesothelin. As used herein, different 'forms' of mesothelin include, but are not restricted to, different glycoforms, different isoforms or mesothelin polypeptides which undergo different translational and posttranslational modifications. As used herein, the term 'comparable affinities' refers to half-maximal antibody potency ($EC_{50}$) values obtained by Scatchard Analysis of FACS data of antibody binding to cells expressing different forms of mesothelin, which do not differ by more than factor 10, or, preferably, factor 5, or, even preferably, factor 2.

It is another object of the invention to provide antibodies, or antigen-binding antibody fragments thereof, or variants thereof that are safe for human administration.

It is another object of the invention to provide antibodies, or antigen-binding antibody fragments thereof, or variants thereof, which bind to human mesothelin and are cross-reactive to mesothelin of another species. Preferably said other species is a rodent, such as for example mouse or rat. Most preferably the antibodies, or antigen-binding antibody fragments thereof, or variants thereof bind to human mesothelin and are cross-reactive to murine mesothelin.

It is another object of the invention to provide antibodies, or antigen-binding antibody fragments thereof, or variants thereof, which invariantly bind to different mesothelin-expressing cell lines with comparable affinity. As used herein, the term 'invariant binding' of a particular antibody to mesothelin refers to its ability to bind to mesothelin on a broad range of mesothelin-expressing cancer cell lines which express different forms of mesothelin. Invariant binding may be caused by, but is not restricted to, the fact that antibodies, or antigen-binding antibody fragments thereof, or variants thereof, recognize an epitope of mesothelin that is not masked by another extracellular antigen, such as cancer antigen 125 (CA125), which interacts with mesothelin.

It is another object of the invention to provide antibodies or variants thereof, which bind to different mesothelin-expressing cancer cells or tumor cells and elicit immune effector activity (e.g. ADCC or CDC) against mesothelin-expressing cancer cells, by using one or more antibodies or variants thereof, of the invention.

It is another object of the invention to provide antibodies, or antigen-binding antibody fragments thereof, or variants thereof, which are internalized following binding to a mesothelin expressing cell. It is also an object of the present invention to provide methods for treating disease by delivering cytotoxic drugs or drug-releasing enzymes to mesothelin-expressing cancer cells, by using one or more antibodies, or antigen-binding antibody fragments thereof, or variants thereof, of the invention.

It is another object of the invention to provide antibodies which constitute a tool for diagnosis of malignant or dysplastic conditions in which mesothelin expression is elevated compared to normal tissue. Provided are anti-mesothelin antibodies conjugated to a detectable marker. Preferred markers are a radiolabel, an enzyme, a chromophore or a fluorescer.

The invention is also related to polynucleotides encoding the antibodies of the invention, cells expressing the antibodies of the invention, methods for producing the antibodies of the invention, methods for inhibiting the growth of dysplastic cells using the antibodies, and methods for treating and detecting cancer using the antibodies.

The invention provides antibodies that are distinguished from Mab K1, SS1, MS-1, MS-2 and MS-3 in that they a) invariantly bind to mesothelin b) are cross-reactive to murine mesothelin c) bind to mesothelin with lower affinities d) internalize efficiently into mesothelin-expressing cells, and e) contain human variable regions.

These and other objects of the invention are more fully described herein.

In one aspect, the invention provides an isolated antibody or functional antibody fragment that contains an antigen-binding region that is specific for an epitope of the 40 kDa mesothelin polypeptide.

Such an antibody or functional fragment thereof may contain an antigen-binding region that contains an H-CDR3 region depicted in SEQ ID NO: 67-98; the antigen-binding region may further include an H-CDR2 region depicted in SEQ ID NO:31-66; and the antigen-binding region also may contain an H-CDR1 region depicted in SEQ ID NO:1-30. Such a mesothelin-specific antibody of the invention may contain an antigen-binding region that contains an L-CDR3 region depicted in SEQ ID NO:160-197; the antigen-binding region may further include an L-CDR1 region depicted in SEQ ID NO:99-128; and the antigen-binding region also may contain an L-CDR2 region depicted in SEQ ID NO:129-159.

Peptide variants of the sequences disclosed herein are also embraced by the present invention. Accordingly, the invention includes anti-mesothelin antibodies having a heavy chain amino acid sequence with: at least 60 percent sequence identity in the CDR regions with the CDR regions depicted in SEQ ID NO:1-197; and/or at least 80 percent sequence homology in the CDR regions with the CDR regions depicted in SEQ ID NO: 1-197. Further included are anti-mesothelin antibodies having a light chain amino acid sequence with: at least 60 percent sequence identity in the CDR regions with the CDR regions depicted in SEQ ID NO: 1-197; and/or at least 80 percent sequence homology in the CDR regions with the CDR regions depicted in SEQ ID NO: 1-197.

An antibody of the invention may be an IgG (e.g., $IgG_1$), while an antibody fragment may be a Fab or scFv, for example. An inventive antibody fragment, accordingly, may be, or may contain, an antigen-binding region that behaves in one or more ways as described herein.

The invention also is related to isolated nucleic acid sequences, each of which can encode an antigen-binding region of a human antibody or functional fragment thereof that is specific for an epitope of mesothelin. Such a nucleic acid sequence may encode a variable heavy chain of an antibody and include a sequence selected from the group consisting of SEQ ID NOS 284-326: or a nucleic acid sequence that hybridizes under high stringency conditions to the complementary strand of SEQ ID NO: 284-326. The nucleic acid might encode a variable light chain of an isolated antibody or functional fragment thereof, and may contain a sequence selected from the group consisting of SEQ ID NOS: 327-369, or a nucleic acid sequence that hybridizes under high stringency conditions to the complementary strand of SEQ ID NO: 327-369.

Nucleic acids of the invention are suitable for recombinant production. Thus, the invention also relates to vectors and host cells containing a nucleic acid sequence of the invention.

Compositions of the invention may be used for therapeutic or prophylactic applications. The invention, therefore, includes a pharmaceutical composition containing an inventive antibody (or functional antibody fragment) and a pharmaceutically acceptable carrier or excipient therefor. In a related aspect, the invention provides a method for treating a disorder or condition associated with the undesired presence of mesothelin expressing cells. Such method contains the steps of administering to a subject in need thereof an effective amount of the pharmaceutical composition that contains an inventive antibody as described or contemplated herein.

The invention also provides instructions for using the antibody library to isolate one or more members of such library that binds specifically and invariantly to mesothelin.

DETAILED DESCRIPTION OF THE INVENTION

Figure 1:
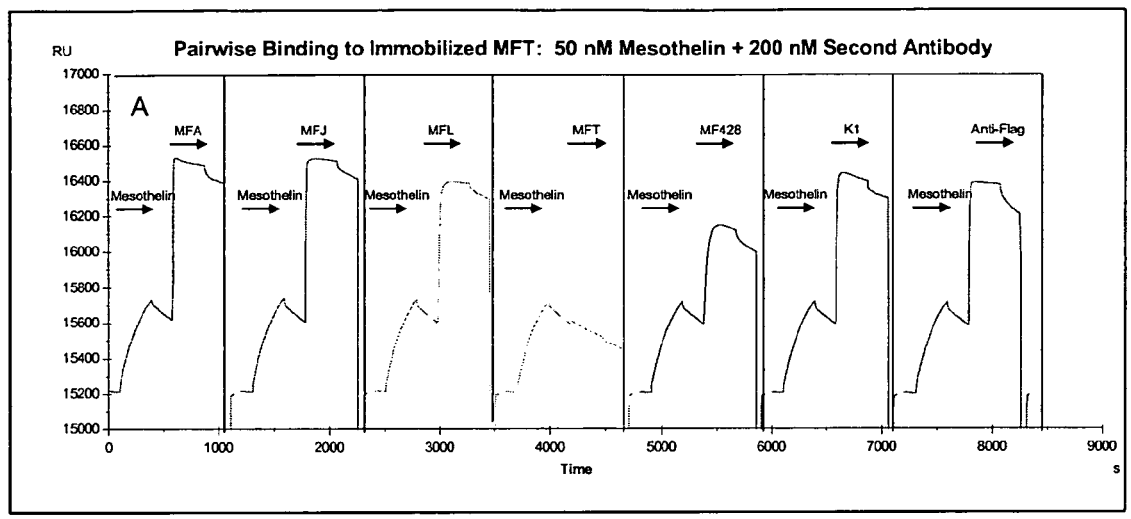
FIG. 1 shows anti-mesothelin antibody epitope grouping by Biacore pairwise binding analysis. Competitive binding of pairs of antibodies was determined by immobilizing one antibody to the sensor chip, binding soluble mesothelin to this antibody and immediately binding a second antibody to mesothelin. Pairs of antibodies which recognize the same or overlapping epitopes on mesothelin cannot bind simultaneously. All combinations of antibody pairs were tested. Representative data for MF-T are shown (A). Panel B depicts the relative positions of epitopes of seven anti-mesothelin antibodies, in which competition is depicted by overlapping circles.
Figure 1:
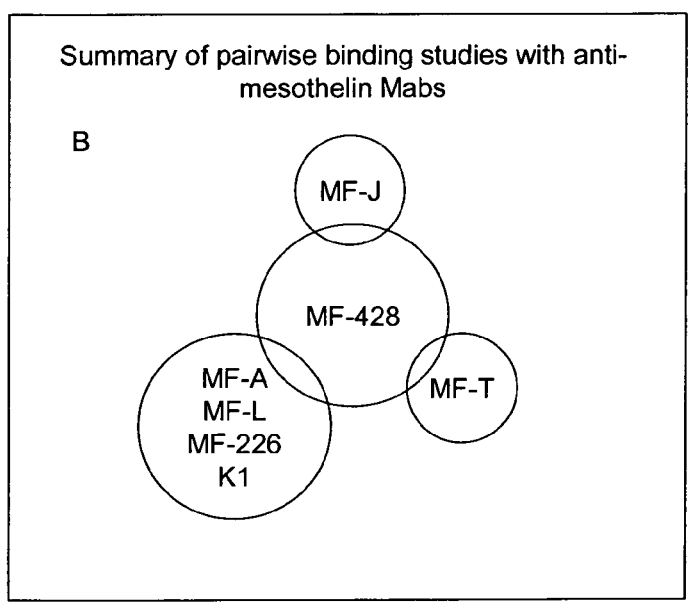

The present invention is based on the discovery of novel antibodies that are specific to or have a high affinity for mesothelin and can deliver a therapeutic benefit to a subject. The antibodies of the invention, which may be human or humanized, can be used in many contexts, which are more fully described herein.

DEFINITIONS

A "human" antibody or functional human antibody fragment is hereby defined as one that is not chimeric (e.g., not "humanized") and not from (either in whole or in part) a non-human species. A human antibody or functional antibody fragment can be derived from a human or can be a synthetic human antibody. A "synthetic human antibody" is defined herein as an antibody having a sequence derived, in whole or in part, in silico from synthetic sequences that are based on the analysis of known human antibody sequences. In silico design of a human antibody sequence or fragment thereof can be achieved, for example, by analyzing a database of human antibody or antibody fragment sequences and devising a polypeptide sequence utilizing the data obtained therefrom. Another example of a human antibody or functional antibody fragment is one that is encoded by a nucleic acid isolated from a library of antibody sequences of human origin (i.e., such library being based on antibodies taken from a human natural source). Examples of human antibodies include HuCAL antibodies as described in Knappik et al., J. Mol. Biol. (2000) 296:57 and U.S. Pat. No. 6,300,064.

A "humanized antibody" or functional humanized antibody fragment is defined herein as one that is (i) derived from a non-human source (e.g., a transgenic mouse which bears a heterologous immune system), which antibody is based on a human germline sequence; or (ii) chimeric, wherein the variable domain is derived from a non-human origin and the constant domain is derived from a human origin or (iii) CDR-grafted, wherein the CDRs of the variable domain are from a non-human origin, while one or more frameworks of the variable domain are of human origin and the constant domain (if any) is of human origin.

As used herein, an antibody "binds specifically to," is "specific to/for" or "specifically recognizes" an antigen (here, mesothelin) if such antibody is able to discriminate between such antigen and one or more reference antigen(s), since binding specificity is not an absolute, but a relative property. In its most general form (and when no defined reference is mentioned), "specific binding" is referring to the ability of the antibody to discriminate between the antigen of interest and an unrelated antigen, as determined, for example, in accordance with one of the following methods. Such methods comprise, but are not limited to Western blots, ELISA-, RIA-, ECL-, IRMA-tests and peptide scans. For example, a standard ELISA assay can be carried out. The scoring may be carried out by standard color development (e.g. secondary antibody with horseradish peroxide and tetramethyl benzidine with hydrogenperoxide). The reaction in certain wells is scored by the optical density, for example, at 450 nm. Typical background (=negative reaction) may be 0.1 OD; typical positive reaction may be 1 OD. This means the difference positive/negative can be more than 10-fold. Typically, determination of binding specificity is performed by using not a single reference antigen, but a set of about three to five unrelated antigens, such as milk powder, BSA, transferrin or the like.

However, "specific binding" also may refer to the ability of an antibody to discriminate between the target antigen and one or more closely related antigen(s), which are used as reference points. Additionally, "specific binding" may relate to the ability of an antibody to discriminate between different parts of its target antigen, e.g. different domains or regions of mesothelin, such as epitopes in the N-terminal or in the C-terminal region of mesothelin, or between one or more key amino acid residues or stretches of amino acid residues of mesothelin.

Also, as used herein, an "immunoglobulin" (Ig) hereby is defined as a protein belonging to the class IgG, IgM, IgE, IgA, or IgD (or any subclass thereof), and includes all conventionally known antibodies and functional fragments thereof. A "functional fragment" or "antigen-binding antibody fragment" of an antibody/immunoglobulin hereby is defined as a fragment of an antibody/immunoglobulin (e.g., a variable region of an IgG) that retains the antigen-binding region. An "antigen-binding region" of an antibody typically is found in one or more hypervariable region(s) of an antibody, i.e., the CDR-1, -2, and/or -3 regions; however, the variable "framework" regions can also play an important role in antigen binding, such as by providing a scaffold for the CDRs. Preferably, the "antigen-binding region" comprises at least amino acid residues 4 to 103 of the variable light (VL) chain and 5 to 109 of the variable heavy (VH) chain, more preferably amino acid residues 3 to 107 of VL and 4 to 111 of VH, and particularly preferred are the complete VL and VH chains (amino acid positions 1 to 109 of VL and 1 to 113 of VH; numbering according to WO 97/08320). A preferred class of immunoglobulins for use in the present invention is IgG. "Functional fragments" of the invention include Fab, Fab', F(ab')$_2$, and Fv fragments; diabodies; linear antibodies; single-chain antibody molecules (scFv); and multispecific antibodies formed from antibody fragments (C. A. K Borrebaeck, editor (1995) Antibody Engineering (Breakthroughs in Molecular Biology), Oxford University Press; R. Kontermann & S. Duebel, editors (2001) Antibody Engineering (Springer Laboratory Manual), Springer Verlag). An antibody other than a "bispecific" or "bifunctional" antibody is understood to have each of its binding sites identical. The F(ab')$_2$ or Fab may be engineered to minimize or completely remove the intermolecular disulphide interactions that occur between the $C_{H1}$ and $C_L$ domains.

An antibody of the invention may be derived from a recombinant antibody library that is based on amino acid sequences that have been designed in silico and encoded by nucleic acids that are synthetically created. In silico design of an antibody sequence is achieved, for example, by analyzing a database of human sequences and devising a polypeptide sequence utilizing the data obtained therefrom. Methods for designing and obtaining in silico-created sequences are described, for example, in Knappik et al., J. Mol. Biol. (2000) 296:57; Krebs et al., J. Immunol. Methods. (2001) 254:67; and U.S. Pat. No. 6,300,064 issued to Knappik et al., which hereby are incorporated by reference in their entirety.

As used herein, different 'forms' of antigen, e.g. mesothelin, are hereby defined as different protein molecules resulting from different translational and posttranslational modifications, such as, but not limited to, differences in splicing of the primary mesothelin transcript, differences in glycosylation, and differences in posttranslational proteolytic cleavage.

As used herein, the term 'invariant binding' of a particular antibody to mesothelin refers to its ability to bind to mesothelin on a broad range of mesothelin-expressing cancer cell lines which express different forms of mesothelin. For invariantly binding antibodies, EC50 values determined by FACS titration on two distinct cancer cell lines might differ no more than 10 fold, or, preferably, 5 fold, and most preferably between 1 and 3 fold.

As used herein, the term 'epitope' includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. Two antibodies are said to 'bind the same epitope' if one antibody is shown to compete with the second antibody in a competitive binding assay, by any of the methods well known to those of skill in the art.

Antibodies of the Invention

The present invention relates to methods to inhibit growth of mesothelin-positive cancer cells and the progression of neoplastic disease by providing anti-mesothelin antibodies. Provided are human monoclonal antibodies, antigen-binding antibody fragments thereof, and variants of the antibodies and fragments, that specifically bind to the 40 kDa, C-terminal domain of the mesothelin precursor polypeptide (SEQ ID NO 370), which is named 'mesothelin' herein.

The antibodies, antigen-binding antibody fragments, and variants of the antibodies and fragments of the invention are comprised of a light chain variable region and a heavy chain variable region. Variants of the antibodies or antigen-binding antibody fragments contemplated in the invention are molecules in which the binding activity of the antibody or antigen-binding antibody fragment for mesothelin is maintained.

Throughout this document, reference is made to the following representative antibodies of the invention: "MF-J", "MOR07265", "MOR06631", "MOR 06635", "MOR06669", "MOR07111", "MOR06640", "MOR06642", "MOR06643", "MF-226", "MOR06626", "MOR06638", "MF-A", "MOR06657", "MF-T", "MF1", "MF-5", "MF-8", "MF-24", "MF-25", "MF-27", "MF-73", "MF-78", "MF-84", "MF-101", "MF-230", "MF-236", "MF-252", "MF-257", "MF-423", "MF-427", "MF-428", MF-C", "MF-I", "MF-L", "MF-M", "MF-P", "MF-Q", MF-S", "MF-V", "MF-W", and "MF-Y". MF-J represents an antibody having a variable heavy region corresponding to SEQ ID NO: 284 (DNA)/SEQ ID NO: 198 (protein) and a variable light region corresponding to SEQ ID NO: 327 (DNA)/SEQ ID NO: 241 (protein). MOR 07265 represents an antibody having a variable heavy region corresponding to SEQ ID NO: 285 (DNA)/SEQ ID NO: 199 (protein) and a variable light region corresponding to SEQ ID NO: 328 (DNA)/SEQ ID NO: 242 (protein). MOR 06631 represents an antibody having a variable heavy region corresponding to SEQ ID NO: 286 (DNA)/SEQ ID NO: 200 (protein) and a variable light region corresponding to SEQ ID NO: 329 (DNA)/SEQ ID NO: 243 (protein). MOR 06669 represents an antibody having a variable heavy region corresponding to SEQ ID NO: 287 (DNA)/SEQ ID NO: 201 (protein) and a variable light region corresponding to SEQ ID NO: 330 (DNA)/SEQ ID NO: 244 (protein). MOR 07111 represents an antibody having a variable heavy region corresponding to SEQ ID NO: 288 (DNA)/SEQ ID NO: 202 (protein) and a variable light region corresponding to SEQ ID NO: 331 (DNA)/SEQ ID NO: 245 (protein). MOR 06640 represents an antibody having a variable heavy region corresponding to SEQ ID NO: 289 (DNA)/SEQ ID NO: 203 (protein) and a variable light region corresponding to SEQ ID NO: 332 (DNA)/SEQ ID NO: 246 (protein). MOR 06642 represents an antibody having a variable heavy region corresponding to SEQ ID NO: 290 (DNA)/SEQ ID NO: 204 (protein) and a variable light region corresponding to SEQ ID NO: 333 (DNA)/SEQ ID NO: 247 (protein). MOR 06643 represents an antibody having a variable heavy region corresponding to SEQ ID NO: 291 (DNA)/SEQ ID NO: 205 (protein) and a variable light region corresponding to SEQ ID NO: 334 (DNA)/SEQ ID NO: 248 (protein). MF-226 represents an antibody having a variable heavy region corresponding to SEQ ID NO: 292 (DNA)/SEQ ID NO: 206 (protein) and a variable light region corresponding to SEQ ID NO: 335 (DNA)/SEQ ID NO: 249 (protein). MOR 06626 represents an antibody having a variable heavy region corresponding to SEQ ID NO: 293 (DNA)/SEQ ID NO: 207 (protein) and a variable light region corresponding to SEQ ID NO: 336 (DNA)/SEQ ID NO: 250 (protein). MOR 06635 represents an antibody having a variable heavy region corresponding to SEQ ID NO: 294 (DNA)/SEQ ID NO: 208 (protein) and a variable light region corresponding to SEQ ID NO: 337 (DNA)/SEQ ID NO: 251 (protein). MOR 06638 represents an antibody having a variable heavy region corresponding to SEQ ID NO: 295 (DNA)/SEQ ID NO: 209 (protein) and a variable light region corresponding to SEQ ID NO: 338 (DNA)/SEQ ID NO: 252 (protein). MF-A represents an antibody having a variable heavy region corresponding to SEQ ID NO: 296 (DNA)/SEQ ID NO: 210 (protein) and a variable light region corresponding to SEQ ID NO: 339 (DNA)/SEQ ID NO: 253 (protein). MOR 06657 represents an antibody having a variable heavy region corresponding to SEQ ID NO: 297 (DNA)/SEQ ID NO: 211 (protein) and a variable light region corresponding to SEQ ID NO: 340 (DNA)/SEQ ID NO: 254 (protein). MF-T represents an antibody having a variable heavy region corresponding to SEQ ID NO: 298 (DNA)/SEQ ID NO: 212 (protein) and a variable light region corresponding to SEQ ID NO: 341 (DNA)/SEQ ID NO: 255 (protein). MF-L represents an antibody having a variable heavy region corresponding to SEQ ID NO: 299 (DNA)/SEQ ID NO: 213 (protein) and a variable light region corresponding to SEQ ID NO: 342 (DNA)/SEQ ID NO: 256 (protein). MF-1 represents an antibody having a variable heavy region corresponding to SEQ ID NO: 300 (DNA)/SEQ ID NO: 214 (protein) and a variable light region corresponding to SEQ ID NO: 343 (DNA)/SEQ ID NO: 257 (protein). MF-5 represents an antibody having a variable heavy region corresponding to SEQ ID NO: 301 (DNA)/SEQ ID NO: 215 (protein) and a variable light region corresponding to SEQ ID NO: 344 (DNA)/SEQ ID NO: 258 (protein). MF-8 represents an antibody having a variable heavy region corresponding to SEQ ID NO: 302 (DNA)/SEQ ID NO: 216 (protein) and a variable light region corresponding to SEQ ID NO: 345 (DNA)/SEQ ID NO: 259 (protein). MF-24 represents an antibody having a variable heavy region corresponding to SEQ ID NO: 303 (DNA)/SEQ ID NO: 217 (protein) and a variable light region corresponding to SEQ ID NO: 346 (DNA)/SEQ ID NO: 260 (protein). MF-25 represents an antibody having a variable heavy region corresponding to SEQ ID NO: 304 (DNA)/SEQ ID NO: 218 (protein) and a variable light region corresponding to SEQ ID NO: 347 (DNA)/SEQ ID NO: 261 (protein). MF-27 represents an antibody having a variable heavy region corresponding to SEQ ID NO: 305 (DNA)/SEQ ID NO: 219 (protein) and a variable light region corresponding to SEQ ID NO: 348 (DNA)/SEQ ID NO: 262 (protein). MF-73 represents an antibody having a variable heavy region corresponding to SEQ ID NO: 306 (DNA)/SEQ ID NO: 220 (protein) and a variable light region corresponding to SEQ ID NO: 349 (DNA)/SEQ ID NO: 263 (protein). MF-78 represents an antibody having a variable heavy region corresponding to SEQ ID NO: 307 (DNA)/SEQ ID NO: 221 (protein) and a variable light region corresponding to SEQ ID NO: 350 (DNA)/SEQ ID NO: 264 (protein). MF-84 represents an antibody having a variable heavy region corresponding to SEQ ID NO: 308 (DNA)/SEQ ID NO: 222 (protein) and a variable light region corresponding to SEQ ID NO: 351 (DNA)/SEQ ID NO: 265 (protein). MF-101 represents an antibody having a variable heavy region corresponding to SEQ ID NO: 309 (DNA)/SEQ ID NO: 223 (protein) and a variable light region corresponding to SEQ ID NO: 352 (DNA)/SEQ ID NO: 266 (protein). MF-230 represents an antibody having a variable heavy region corresponding to SEQ ID NO: 310 (DNA)/SEQ ID NO: 224 (protein) and a variable light region corresponding to SEQ ID NO: 353 (DNA)/SEQ ID NO: 267 (protein). MF-236 represents an antibody having a variable heavy region corresponding to SEQ ID NO: 311 (DNA)/SEQ ID NO: 225 (protein) and a variable light region corresponding to SEQ ID NO: 354 (DNA)/SEQ ID NO: 268 (protein). MF-252 represents an antibody having a variable heavy region corresponding to SEQ ID NO: 312 (DNA)/SEQ ID NO: 226 (protein) and a variable light region corresponding to SEQ ID NO: 355 (DNA)/SEQ ID NO: 269 (protein). MF-275 represents an antibody having a variable heavy region corresponding to SEQ ID NO: 313 (DNA)/SEQ ID NO: 227 (protein) and a variable light region corresponding to SEQ ID NO: 356 (DNA)/SEQ ID NO: 270 (protein). MF-423 represents an antibody having a variable heavy region corresponding to SEQ ID NO: 314 (DNA)/SEQ ID NO: 228 (protein) and a variable light region corresponding to SEQ ID NO: 357 (DNA)/SEQ ID NO: 271 (protein). MF-427 represents an antibody having a variable heavy region corresponding to SEQ ID NO: 315 (DNA)/SEQ ID NO: 229 (protein) and a variable light region corresponding to SEQ ID NO: 358 (DNA)/SEQ ID NO: 272 (protein). MF-428 represents an antibody having a variable heavy region corresponding to SEQ ID NO: 316 (DNA)/SEQ ID NO: 230 (protein) and a variable light region corresponding to SEQ ID NO: 359 (DNA)/SEQ ID NO: 273 (protein). MF-C represents an antibody having a variable heavy region corresponding to SEQ ID NO: 317 (DNA)/SEQ ID NO: 231 (protein) and a variable light region corresponding to SEQ ID NO: 360 (DNA)/SEQ ID NO: 274 (protein). MF-I represents an antibody having a variable heavy region corresponding to SEQ ID NO: 318 (DNA)/SEQ ID NO: 232 (protein) and a variable light region corresponding to SEQ ID NO: 361 (DNA)/SEQ ID NO: 275 (protein). MF-M represents an antibody having a variable heavy region corresponding to SEQ ID NO: 319 (DNA)/SEQ ID NO: 233 (protein) and a variable light region corresponding to SEQ ID NO: 362 (DNA)/SEQ ID NO: 276 (protein). MF-P represents an antibody having a variable heavy region corresponding to SEQ ID NO: 320 (DNA)/SEQ ID NO: 234 (protein) and a variable light region corresponding to SEQ ID NO: 363 (DNA)/SEQ ID NO: 277 (protein). MF-Q represents an antibody having a variable heavy region corresponding to SEQ ID NO: 321 (DNA)/SEQ ID NO: 235 (protein) and a variable light region corresponding to SEQ ID NO: 364 (DNA)/SEQ ID NO: 278 (protein). MF-S represents an antibody having a variable heavy region corresponding to SEQ ID NO: 322 (DNA)/SEQ ID NO: 236 (protein) and a variable light region corresponding to SEQ ID NO: 365 (DNA)/SEQ ID NO: 279 (protein). MF-U represents an antibody having a variable heavy region corresponding to SEQ ID NO: 323 (DNA)/SEQ ID NO: 237 (protein) and a variable light region corresponding to SEQ ID NO: 366 (DNA)/SEQ ID NO: 280 (protein). MF-V represents an antibody having a variable heavy region corresponding to SEQ ID NO: 324 (DNA)/SEQ ID NO: 238 (protein) and a variable light region corresponding to SEQ ID NO: 367 (DNA)/SEQ ID NO: 281 (protein). MF-W represents an antibody having a variable heavy region corresponding to SEQ ID NO: 325 (DNA)/SEQ ID NO: 239 (protein) and a variable light region corresponding to SEQ ID NO: 368 (DNA)/SEQ ID NO: 282 (protein). MF-Y represents an antibody having a variable heavy region corresponding to SEQ ID NO: 326 (DNA)/SEQ ID NO: 240 (protein) and a variable light region corresponding to SEQ ID NO: 369 (DNA)/SEQ ID NO: 283 (protein).

In one aspect, the invention provides antibodies which bind to epitopes of mesothelin, whose amino acid sequence is depicted by SEQ ID NO: 370, that are distinct from the mesothelin epitope recognized by Mab K1.

In other aspects the invention provides antibodies which bind to one or more amino acids of the epitopes of antibodies MF-J or MF-T. In certain aspects said antibodies bind to at least to two, at least three, at least four, at least five or at least six amino acids of the epitopes of antibodies MF-J or MF-T. In certain aspects the antibodies of the present invention bind to one or more amino acids of the epitope recognized by the antibody MF-J. In alternative aspects the antibodies of the present invention bind to one or more amino acids of the epitope recognized by the antibody MF-T.

In another aspect, the invention provides antibodies having an antigen-binding region that can bind specifically to or has a high affinity for one or more regions of mesothelin, whose amino acid sequence is depicted by SEQ ID NO: 370. An antibody is said to have a "high affinity" for an antigen if the affinity measurement is at least 100 nM (monovalent affinity of Fab fragment). An inventive antibody or antigen-binding region preferably can bind to mesothelin with an affinity of less than about 100 nM, more preferably less than about 60 nM, and still more preferably less than about 30 nM. Further preferred are antibodies that bind to mesothelin with an affinity of less than about 10 nM, and more preferably less than about 3 nM. For instance, the affinity of an antibody of the invention against mesothelin may be about 10.0 nM or 0.19 nM (monovalent affinity of Fab fragment).

Table 1 provides a summary of dissociation constants and dissociation rates of representative antibodies of the invention, as determined by surface plasmon resonance (Biacore) on directly immobilized mesothelin.

TABLE 1

Monovalent dissociation constants and dissociation rates to mesothelin determined for anti-mesothelin Fabs by surface plasmon resonance

| Antibody | $K_D$ [M] | kd [1/s] |
|---|---|---|
| MF-A | $1.9 \times 10^{-8}$ | $7.9 \times 10^{-2}$ |
| MOR06657 | $9.5 \times 10^{-10}$ | $5.5 \times 10^{-3}$ |
| MF-J | $9.2 \times 10^{-9}$ | $2.9 \times 10^{-3}$ |
| MOR06631 | $9 \times 10^{-11}$ | $1.4 \times 10^{-5}$ |
| MOR06669 | $2.4 \times 10^{-10}$ | $8.1 \times 10^{-5}$ |
| MOR06643 | $3.6 \times 10^{-10}$ | $2.8 \times 10^{-4}$ |
| MF-226 | $5.8 \times 10^{-8}$ | $3.8 \times 10^{-2}$ |
| MOR06626 | $6.7 \times 10^{-10}$ | $1.2 \times 10^{-3}$ |
| MOR06638 | $1.6 \times 10^{-8}$ | $6.3 \times 10^{-3}$ |

The IgG1 format was used for the cell-based affinity determination, determined by fluorescence-activated cell sorting (FACS) combined with Scatchard analysis, and live cell enzyme-linked immunosorbed assay (ELISA). Table 2 denotes the binding strength of representative IgG antibodies on mesothelin-expressing CHO-A9 cells.

TABLE 2

Cell-based binding potency of anti-mesothelin antibodies as determined by cell ELISA and FACS on mesothelin-expressing CHO-A9 cells

| | EC50 | |
|---|---|---|
| Antibody (IgG) | FACS [nM] | Cell ELISA [nM] |
| MF-A | 0.05 | 0.8 |
| MF-J | 0.11 | 3.9 |
| MF-L | 0.07 | 0.8 |
| MF-T | 0.27 | 1.5 |
| MF-226 | 0.15 | 0.4 |

Antibody Generation

A synthetic antibody phage display library (Knappik, A., et al., J. Mol. Biol. (2000) 296(1): 57) was used to isolate high affinity, mesothelin-specific, human monoclonal antibodies, by a combination of whole cell and protein pannings and through the development of specific tools. These tools and methods include a mesothelin-expressing recombinant cell-line and the development of panning procedures and screening assays capable of identifying antibodies that preferentially bind to mesothelin displayed on the cell surface and that are crossreactive to mesothelin from other species.

Antibodies to the mesothelial cancer cell-surface marker, mesothelin, were discovered by a combination of three non-conventional approaches in phage-display technology (PDT). First, a recombinant cell line expressing the membrane-bound, 40 kDa domain of mesothelin was constructed by stable transfection of CHO-K1 cells with a plasmid encoding the GPI-anchored C-terminal part of the protein (SEQ ID 371), to give the CHO-A9 cell line. Second, dual-alternating cell-surface selections were performed with the latter recombinant cell line and the squamous cancer cell line NCI-H226. Pre-adsorption with CHO-K1 cells was included to avoid the selection of Fab fragments binding to epitopes of the parental cells. Additional selections were performed with recombinant, soluble purified human mesothelin (unique source of "MF-24", "MF-25", and "MF-27"), with recombinant, murine mesothelin, with purified deglycosylated mesothelin (unique source of "MF-5" and "MF-8"), and with biotinylated mesothelin in soluble phase. Third, screening methods were developed which allowed for successive screening of the phage outputs obtained in panning on whole NCI-H226 cells as well as CHO-A9 cells. The combination of these specific methods allowed the isolation of the unique antibodies "MF-J", "MF-226", "MF-A", "MF-T", "MF-1", "MF-5", "MF-8", "MF-24", "MF-25", "MF-27", "MF-73", "MF-78", "MF-84", "MF-101", "MF-230", "MF-236", "MF-252", "MF-275", "MF-423", "MF-427", "MF-428", MF-C", "MF-I", "MF-L", "MF-M", "MF-P", "MF-Q", MF-S", "MF-U", "MF-V", "MF-W", and "MF-Y". These unique antibodies were further characterized by their binding affinity in two cell based ELISA's, by BIAcore binding to soluble mesothelin, by their ability to recognize different epitopes on soluble mesothelin, and by their ability to cross react with murine mesothelin assessed by FACS and immunoblotting, and their ability to be internalized in three different cell based assays. Two of the internalization assays quantitatively measured the internalization of radiolabelled anti-mesothelin antibodies either in the absence of presence of a secondary antibody to human IgG. This data was used to select four antibodies for further affinity maturation.

In order to obtain antibodies with robust invariant binding to different forms of mesothelin displayed on different cancer cell lines, to increase species cross-reactivity, and to further increase affinity and decrease dissociation rates, a strategy for affinity maturation was designed. Affinity maturation was performed on antibodies 'MF-J', 'MF-226', 'MF-L' and 'MF-A'. Affinity maturation included generation of new antibody repertoires by the exchange of H-CDR2, L-CDR3, or a combination of both H-CDR2 and L-CDR3 regions of the parental antibodies. Alternating selections were performed with the two mesothelin-expressing cancer cell lines NCI-H226 and OVCAR-3, as well as recombinant purified and biotinylated human and murine meothelin in solution using magnetic beads. Increasing stringency was obtained by gradual reduction of antigen and extension of the washing procedure.

Screening was performed by first ranking the hits by decreasing affinity, as determined on antigen-coated beads in solution, by measuring an electrochemiluminescent signal in a M-384 Workstation (BioVeris). Subsequently, a resulting selection of high-affinity binders was submitted to solutionequilibrium titration (SET) screening (Haenel, C., et al., Anal. Biochem. (2005) 339(1): 182). The best binders were further screened by analysis of cross-reactivity to murine mesothelin, as well as for binding to mesothelin on NCI-H226 cells by FACS. The combination of these specific methods allowed the isolation of the unique antibodies 'MOR07265', 'MOR06631', 'MOR 06635', 'MOR06669', 'MOR07111', 'MOR06640', 'MOR06642', 'MOR06643', 'MOR06626', 'MOR06638' and 'MOR06657'.

Peptide Variants

Antibodies of the invention are not limited to the specific peptide sequences provided herein. Rather, the invention also embodies variants of these polypeptides. With reference to the instant disclosure and conventionally available technologies and references, the skilled worker will be able to prepare, test and utilize functional variants of the antibodies disclosed herein, while appreciating that variants having the ability to bind to mesothelin fall within the scope of the present invention.

A variant can include, for example, an antibody that has at least one altered complementary determining region (CDR) (hyper-variable) and/or framework (FR) (variable) domain/position, vis-à-vis a peptide sequence disclosed herein. To better illustrate this concept, a brief description of antibody structure follows.

An antibody is composed of two peptide chains, each containing one (light chain) or three (heavy chain) constant domains and a variable region (VL, VH), the latter of which is in each case made up of four FR regions and three interspaced CDRs. The antigen-binding site is formed by one or more CDRs, yet the FR regions provide the structural framework for the CDRs and, hence, play an important role in antigen binding. By altering one or more amino acid residues in a CDR or FR region, the skilled worker routinely can generate mutated or diversified antibody sequences, which can be screened against the antigen, for new or improved properties, for example.

Tables 3 (VH) and 4 (VL) delineate the CDR and FR regions for certain antibodies of the invention and compare amino acids at a given position to each other and to corresponding consensus or "master gene" sequences (as described in U.S. Pat. No. 6,300,064):

TABLE 3

VH Sequences

MF-226 HC  (1)
MF-A HC    (1)
MF-T HC    (1)
MF-J HC    (1)
MOR06640 HC (1)
Consensus  (1)  QVELVQSGAEVKKPGESLKISCKGSGYSFT YWIGWVRQAPGKGLEWMGI MF-226 HC  (51)
MF-A HC    (51)
MF-T HC    (51)
MF-J HC    (51)
MOR06640 HC (51)
Consensus  (51)  IMP DS TRYSPSFQGQVTISADKSISTAYLQWSSLKASDTAMYYCARYG MF-226 HC  (101)
MF-A HC    (101)
MF-T HC    (100)
MF-J HC    (101)
MOR06640 HC (101)
Consensus  (101)  HG YG LD WGQGTLVTVSS

TABLE 4

VL Sequences

MF-226 VL  (1)
MF-A VL    (1)
MF-T VL    (1)
MF-J VL    (1)
MOR06640 VL (1)
Consensus  (1)  DIVLTQ PASVSGSPGQRITISCTGSSS IG N VSWYQQ PG APKLL MF-226 VL  (49)
MF-A VL    (50)
MF-T VL    (50)
MF-J VL    (49)
MOR06640 VL (49)
Consensus  (51)  IYG SKRPSGVP RFSGSKSGTTASLTISGLQAEDEADYYC Y S TABLE 4-continued VL Sequences

```
                   CDR3
                   101          114
MF-226  VL  (99)  -█████████████
  MF-A  VL (100)  K█████████████
  MF-T  VL (100)  P█████████████
  MF-J  VL  (98)  -T█Q██VEIKRT
MOR06640 VL (99)  -T█Q██VEIKRT
Consensus  (101)   VFGGGTKLTVLGQ
```

In certain aspects the present invention provides antibodies wherein the HCDR1 region is selected from sequence ID's [all respective SEQ IDs of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30.

wherein the HCDR2 region is selected from sequence ID's 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65 or 66.

wherein the HCDR3 region is selected from sequence ID's 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97 or 98.

wherein the LCDR1 region is selected from sequence ID's 99, 100, 101, 102, 103, 104, 105, 106, 107, 108, 109, 110, 111, 112, 113, 114, 115, 116, 117, 118, 119, 120, 121, 122, 123, 124, 125, 126, 127, 102 or 128.

wherein the LCDR2 region is selected from sequence ID's 129, 130, 131 132, 133, 134, 135, 136, 137, 138, 139, 140, 141, 142, 143, 144, 145, 146, 147, 148, 149, 150, 151, 152, 153, 154, 155, 156, 157, 158, 159 or 155.

wherein the LCDR3 region is selected from sequence ID's 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196 or 197. or combinations of these CDR regions.

Preferred aspects are antibodies: in which the CDR sequences are selected from the MF-J series as shown in table 7 or other combinations of the CDR regions shown in table 7.

In certain aspects the present invention provides antibodies wherein the VH is selected from sequence ID 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239 or 240, wherein the VL is selected from sequence ID 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282 or 283.

As above, preferred aspects for MF-J series as shown in table 7 or other combinations of the VH and VL regions shown in table 7.

The skilled worker can use the data in Tables 3, 4 and 7 to design peptide variants that are within the scope of the present invention. It is preferred that variants are constructed by changing amino acids within one or more CDR regions; a variant might also have one or more altered framework regions. With reference to a comparison of the novel antibodies to each other, candidate residues that can be changed include e.g. residues 3 or 45 of the variable light and e.g. residues 16 or 43 of the variable heavy chains of MF-226 and MF-T, since these are positions of variance vis-à-vis each other. Alterations also may be made in the framework regions. For example, a peptide FR domain might be altered where there is a deviation in a residue compared to a germline sequence.

With reference to a comparison of the novel antibodies to the corresponding consensus or "master gene" sequence, which are listed in Knappik et al., 2000, candidate residues that can be changed include e.g. residues 29 or 52 of the variable light chain of MF-T compared to VLλ2 and e.g. residues 43 or 57 of the variable heavy chain of MF-A compared to VH1A (Knappik, A., et al., J. Mol. Biol. (2000) 296(1): 57). Alternatively, the skilled worker could make the same analysis by comparing the amino acid sequences disclosed herein to known sequences of the same class of such antibodies, using, for example, the procedure described by Knappik, A., et al. (2000) and U.S. Pat. No. 6,300,064 issued to Knappik et al.

Furthermore, variants may be obtained by using one antibody as starting point for optimization by diversifying one or more amino acid residues in the antibody, preferably amino acid residues in one or more CDRs, and by screening the resulting collection of antibody variants for variants with improved properties. Particularly preferred is diversification of one or more amino acid residues in CDR-3 of VL, CDR-3 of VH, CDR-1 of VL and/or CDR-2 of VH. Diversification can be done by synthesizing a collection of DNA molecules using trinucleotide mutagenesis (TRIM) technology (Virnekäs, B., Ge, L., Plückthun, A., Schneider, K. C., Wellnhofer, G., and Moroney S. E. (1994) Trinucleotide phosphoramidites: ideal reagents for the synthesis of mixed oligonucleotides for random mutagenesis. Nucl. Acids Res. 22, 5600.).

Conservative Amino Acid Variants

Polypeptide variants may be made that conserve the overall molecular structure of an antibody peptide sequence described herein. Given the properties of the individual amino acids, some rational substitutions will be recognized by the skilled worker. Amino acid substitutions, i.e., "conservative substitutions," may be made, for instance, on the basis of similarity in polarity, charge, solubility, hydrophobicity, hydrophilicity, and/or the amphipathic nature of the residues involved.

For example, (a) nonpolar (hydrophobic) amino acids include alanine, leucine, isoleucine, valine, proline, phenylalanine, tryptophan, and methionine; (b) polar neutral amino acids include glycine, serine, threonine, cysteine, tyrosine, asparagine, and glutamine; (c) positively charged (basic) amino acids include arginine, lysine, and histidine; and (d) negatively charged (acidic) amino acids include aspartic acid and glutamic acid. Substitutions typically may be made within groups (a)-(d). In addition, glycine and proline may be substituted for one another based on their ability to disrupt α-helices. Similarly, certain amino acids, such as alanine, cysteine, leucine, methionine, glutamic acid, glutamine, histidine and lysine are more commonly found in α-helices, while valine, isoleucine, phenylalanine, tyrosine, tryptophan and threonine are more commonly found in β-pleated sheets. Glycine, serine, aspartic acid, asparagine, and proline are commonly found in turns. Some preferred substitutions may be made among the following groups: (i) S and T; (ii) P and G; and (iii) A, V, L and I. Given the known genetic code, and recombinant and synthetic DNA techniques, the skilled scientist readily can construct DNAs encoding the conservative amino acid variants. In one particular example, amino acid position 3 in SEQ ID NOS: 199-205, 207-211 or 213-240 can be changed from a Q to an E.

As used herein, "sequence identity" between two polypeptide sequences, indicates the percentage of amino acids that are identical between the sequences. "Sequence homology" indicates the percentage of amino acids that either are identical or that represent conservative amino acid substitutions. Preferred polypeptide sequences of the invention have a sequence identity in the CDR regions of at least 60%, more preferably, at least 70% or 80%, still more preferably at least 90% and most preferably at least 95%. Preferred antibodies also have a sequence homology in the CDR regions of at least 80%, more preferably 90% and most preferably 95%.

DNA Molecules of the Invention

The present invention also relates to the DNA molecules that encode an antibody of the invention. These sequences include, but are not limited to, those DNA molecules set forth in SEQ IDs 284-369.

DNA molecules of the invention are not limited to the sequences disclosed herein, but also include variants thereof. DNA variants within the invention may be described by reference to their physical properties in hybridization. The skilled worker will recognize that DNA can be used to identify its complement and, since DNA is double stranded, its equivalent or homolog, using nucleic acid hybridization techniques. It also will be recognized that hybridization can occur with less than 100% complementarity. However, given appropriate choice of conditions, hybridization techniques can be used to differentiate among DNA sequences based on their structural relatedness to a particular probe. For guidance regarding such conditions see, Sambrook et al., 1989 (Sambrook, J., Fritsch, E. F. and Maniatis, T. (1989) Molecular Cloning: A laboratory manual, Cold Spring Harbor Laboratory Press, Cold Spring Harbor, USA) and Ausubel et al., 1995 (Ausubel, F. M., Brent, R., Kingston, R. E., Moore, D. D., Sedman, J. G., Smith, J. A., & Struhl, K. eds. (1995). Current Protocols in Molecular Biology. New York: John Wiley and Sons).

Structural similarity between two polynucleotide sequences can be expressed as a function of "stringency" of the conditions under which the two sequences will hybridize with one another. As used herein, the term "stringency" refers to the extent that the conditions disfavor hybridization. Stringent conditions strongly disfavor hybridization, and only the most structurally related molecules will hybridize to one another under such conditions. Conversely, non-stringent conditions favor hybridization of molecules displaying a lesser degree of structural relatedness. Hybridization stringency, therefore, directly correlates with the structural relationships of two nucleic acid sequences. The following relationships are useful in correlating hybridization and relatedness (where $T_m$, is the melting temperature of a nucleic acid duplex):

a. $T_m=69.3+0.41(G+C)\%$ b. The $T_m$ of a duplex DNA decreases by 1° C. with every increase of 1% in the number of mismatched base pairs.

c. $(T_m)_{\mu 2}-(T_m)_{\mu 1}=18.5 \log_{10}\mu 2/\mu$ where µ1 and µ2 are the ionic strengths of two solutions.

Hybridization stringency is a function of many factors, including overall DNA concentration, ionic strength, temperature, probe size and the presence of agents which disrupt hydrogen bonding. Factors promoting hybridization include high DNA concentrations, high ionic strengths, low temperatures, longer probe size and the absence of agents that disrupt hydrogen bonding. Hybridization typically is performed in two phases: the "binding" phase and the "washing" phase.

First, in the binding phase, the probe is bound to the target under conditions favoring hybridization. Stringency is usually controlled at this stage by altering the temperature. For high stringency, the temperature is usually between 65° C. and 70° C., unless short (<20 nt) oligonucleotide probes are used. A representative hybridization solution comprises 6×SSC, 0.5% SDS, 5×Denhardt's solution and 100 µg of nonspecific carrier DNA. See Ausubel et al., section 2.9, supplement 27 (1994). Of course, many different, yet functionally equivalent, buffer conditions are known. Where the degree of relatedness is lower, a lower temperature may be chosen. Low stringency binding temperatures are between about 25° C. and 40° C. Medium stringency is between at least about 40° C. to less than about 65° C. High stringency is at least about 65° C.

Second, the excess probe is removed by washing. It is at this phase that more stringent conditions usually are applied. Hence, it is this "washing" stage that is most important in determining relatedness via hybridization. Washing solutions typically contain lower salt concentrations. One exemplary medium stringency solution contains 2×SSC and 0.1% SDS. A high stringency wash solution contains the equivalent (in ionic strength) of less than about 0.2×SSC, with a preferred stringent solution containing about 0.1×SSC. The temperatures associated with various stringencies are the same as discussed above for "binding." The washing solution also typically is replaced a number of times during washing. For example, typical high stringency washing conditions comprise washing twice for 30 minutes at 55° C. and three times for 15 minutes at 60° C.

Accordingly, the present invention includes nucleic acid molecules that hybridize to the molecules of set forth in SEQ ID 284-369 under high stringency binding and washing conditions, where such nucleic molecules encode an antibody or functional fragment thereof having properties as described herein. Preferred molecules (from an mRNA perspective) are those that have at least 75% or 80% (preferably at least 85%, more preferably at least 90% and most preferably at least 95%) homology or sequence identity with one of the DNA molecules described herein. In one particular example of a variant of the invention, nucleic acid position 7 in SEQ ID NOS: 285-291, 293-297, or 299-326 can be substituted from a C to a G, thereby changing the codon from CAA to GAA.

Functionally Equivalent Variants

Yet another class of DNA variants within the scope of the invention may be described with reference to the product they encode. These functionally equivalent genes are characterized by the fact that they encode the same peptide sequences found in SEQ ID 284-369 due to the degeneracy of the genetic code.

It is recognized that variants of DNA molecules provided herein can be constructed in several different ways. For example, they may be constructed as completely synthetic DNAs. Methods of efficiently synthesizing oligonucleotides in the range of 20 to about 150 nucleotides are widely available. See Ausubel et al., section 2.11, Supplement 21 (1993). Overlapping oligonucleotides may be synthesized and assembled in a fashion first reported by Khorana et al., J. Mol. Biol. 72:209-217 (1971); see also Ausubel et al., supra, Section 8.2. Synthetic DNAs preferably are designed with convenient restriction sites engineered at the 5' and 3' ends of the gene to facilitate cloning into an appropriate vector.

As indicated, a method of generating variants is to start with one of the DNAs disclosed herein and then to conduct site-directed mutagenesis. See Ausubel et al., supra, chapter 8, Supplement 37 (1997). In a typical method, a target DNA is cloned into a single-stranded DNA bacteriophage vehicle. Single-stranded DNA is isolated and hybridized with an oligonucleotide containing the desired nucleotide alteration(s). The complementary strand is synthesized and the double stranded phage is introduced into a host. Some of the resulting progeny will contain the desired mutant, which can be confirmed using DNA sequencing. In addition, various methods are available that increase the probability that the progeny phage will be the desired mutant. These methods are well known to those in the field and kits are commercially available for generating such mutants.

Recombinant DNA Constructs and Expression

The present invention further provides recombinant DNA constructs comprising one or more of the nucleotide sequences of the present invention. The recombinant constructs of the present invention are used in connection with a vector, such as a plasmid, phagemid, phage or viral vector, into which a DNA molecule encoding an antibody of the invention is inserted.

The encoded gene may be produced by techniques described in Sambrook et al., 1989, and Ausubel et al., 1989. Alternatively, the DNA sequences may be chemically synthesized using, for example, synthesizers. See, for example, the techniques described in OLIGONUCLEOTIDE SYNTHESIS (1984, Gait, ed., IRL Press, Oxford), which is incorporated by reference herein in its entirety. Recombinant constructs of the invention are comprised with expression vectors that are capable of expressing the RNA and/or protein products of the encoded DNA(s). The vector may further comprise regulatory sequences, including a promoter operably linked to the open reading frame (ORF). The vector may further comprise a selectable marker sequence. Specific initiation and bacterial secretory signals also may be required for efficient translation of inserted target gene coding sequences.

The present invention further provides host cells containing at least one of the DNAs of the present invention. The host cell can be virtually any cell for which expression vectors are available. It may be, for example, a higher eukaryotic host cell, such as a mammalian cell, a lower eukaryotic host cell, such as a yeast cell, and may be a prokaryotic cell, such as a bacterial cell. Introduction of the recombinant construct into the host cell can be effected by calcium phosphate transfection, DEAE, dextran mediated transfection, electroporation or phage infection.

Bacterial Expression

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and, if desirable, to provide amplification within the host. Suitable prokaryotic hosts for transformation include *E. coli, Bacillus subtilis, Salmonella typhimurium* and various species within the genera *Pseudomonas, Streptomyces*, and *Staphylococcus*.

Bacterial vectors may be, for example, bacteriophage-, plasmid- or phagemid-based. These vectors can contain a selectable marker and bacterial origin of replication derived from commercially available plasmids typically containing elements of the well known cloning vector pBR322 (ATCC 37017). Following transformation of a suitable host strain and growth of the host strain to an appropriate cell density, the selected promoter is de-repressed/induced by appropriate means (e.g., temperature shift or chemical induction) and cells are cultured for an additional period. Cells are typically harvested by centrifugation, disrupted by physical or chemical means, and the resulting crude extract retained for further purification.

In bacterial systems, a number of expression vectors may be advantageously selected depending upon the use intended for the protein being expressed. For example, when a large quantity of such a protein is to be produced, for the generation of antibodies or to screen peptide libraries, for example, vectors which direct the expression of high levels of fusion protein products that are readily purified may be desirable.

Therapeutic Methods

Therapeutic methods involve administering to a subject in need of treatment a therapeutically effective amount of an antibody contemplated by the invention. A "therapeutically effective" amount hereby is defined as the amount of an antibody that is of sufficient quantity to deplete mesothelin-positive cells in a treated area of a subject—either as a single dose or according to a multiple dose regimen, alone or in combination with other agents, which leads to the alleviation of an adverse condition, yet which amount is toxicologically tolerable. The subject may be a human or non-human animal (e.g., rabbit, rat, mouse, monkey or other lower-order primate).

An antibody of the invention might be co-administered with known medicaments, and in some instances the antibody might itself be modified. For example, an antibody could be conjugated to an immunotoxin or radioisotope to potentially further increase efficacy.

The inventive antibodies can be used as a therapeutic or a diagnostic tool in a variety of situations where mesothelin undesirably expressed or found. Disorders and conditions particularly suitable for treatment with an antibody of the inventions are pancreatic cancer, ovarian cancer, mesothelioma and lung cancer.

To treat any of the foregoing disorders, pharmaceutical compositions for use in accordance with the present invention may be formulated in a conventional manner using one or more physiologically acceptable carriers or excipients. An antibody of the invention can be administered by any suitable means, which can vary, depending on the type of disorder being treated. Possible administration routes include parenteral (e.g., intramuscular, intravenous, intraarterial, intraperitoneal, or subcutaneous), intrapulmonary and intranasal, and, if desired for local immunosuppressive treatment, intralesional administration. In addition, an antibody of the invention might be administered by pulse infusion, with, e.g., declining doses of the antibody. Preferably, the dosing is given by injections, most preferably intravenous or subcutaneous injections, depending in part on whether the administration is brief or chronic. The amount to be administered will depend on a variety of factors such as the clinical symptoms, weight of the individual, whether other drugs are administered. The skilled artisan will recognize that the route of administration will vary depending on the disorder or condition to be treated.

Determining a therapeutically effective amount of the novel polypeptide, according to this invention, largely will depend on particular patient characteristics, route of administration, and the nature of the disorder being treated. General guidance can be found, for example, in the publications of the International Conference on Harmonisation and in REMING- TON'S PHARMACEUTICAL SCIENCES, chapters 27 and 28, pp. 484-528 (18th ed., Alfonso R. Gennaro, Ed., Easton, Pa.: Mack Pub. Co., 1990). More specifically, determining a therapeutically effective amount will depend on such factors as toxicity and efficacy of the medicament. Toxicity may be determined using methods well known in the art and found in the foregoing references. Efficacy may be determined utilizing the same guidance in conjunction with the methods described below in the Examples.

Diagnostic Methods

Mesothelin antibodies can be used for detecting the presence of mesothelin-expressing tumors. The presence of mesothelin-containing cells within various biological samples, including serum, prostate and other tissue biopsy specimens, may be detected with mesothelin antibodies. In addition, mesothelin antibodies may be used in various imaging methodologies such as immunoscintigraphy with a .sup.99mTc (or other isotope) conjugated antibody. For example, an imaging protocol similar to the one recently described using a .sup.111In conjugated anti-PSMA antibody may be used to detect pancreaetic or ovarian carcinomas (Sodee et al., Clin. Nuc. Med. 21: 759-766, 1997). Another method of detection that can be used is positron emitting tomography (see Herzog et al., J. Nucl. Med. 34:2222-2226, 1993).

Pharmaceutical Compositions and Administration

The present invention also relates to pharmaceutical compositions which may comprise mesothelin antibodies, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

The present invention also relates to the administration of pharmaceutical compositions. Such administration is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxilliaries which facilitate processing of the active compounds into preparations which can be used pharmaceutically. Further details on techniques for formulation and administration may be found in the latest edition of Remington's Pharmaceutical Sciences (Ed. Maack Publishing Co, Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxxilliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl, cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol and/or titanium dioxide, lacquer solutions, and suitable organic solvents or solvent mixtures. Dyestuffs or pigments may be added to the tablets or dragee coatings for product identification or to characterize the quantity of active compound, ie. dosage.

Pharmaceutical preparations that can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hank's solution, Ringer's solution, or physiologically buffered saline. Aqueous injection suspensions may contain substances that increase viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Kits

The invention further relates to pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

In another embodiment, the kits may contain DNA sequences encoding the antibodies of the invention. Preferably the DNA sequences encoding these antibodies are provided in a plasmid suitable for transfection into and expression by a host cell. The plasmid may contain a promoter (often an inducible promoter) to regulate expression of the DNA in the host cell. The plasmid may also contain appropriate restriction sites to facilitate the insertion of other DNA sequences into the plasmid to produce various antibodies. The plasmids may also contain numerous other elements to facilitate cloning and expression of the encoded proteins. Such elements are well known to those of skill in the art and include, for example, selectable markers, initiation codons, termination codons, and the like.

Manufacture and Storage.

The pharmaceutical compositions of the present invention may be manufactured in a manner that is known in the art, e.g., by means of conventional mixing, dissolving, granulating, dragee-making, levigating, emulsifying, encapsulating, entrapping or lyophilizing processes.

The pharmaceutical composition may be provided as a salt and can be formed with may acids, including by not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

After pharmaceutical compositions comprising a compound of the invention formulated in an acceptable carrier have been prepared, they can be placed in an appropriate container and labeled for treatment of an indicated condition. For administration of mesothelin antibodies, such labeling would include amount, frequency and method of administration.

Therapeutically Effective Dose.

Pharmaceutical compositions suitable for use in the present invention include compositions wherein the active ingredients are contained in an effective amount to achieve the intended purpose, i.e. treatment of a particular disease state characterized by mesothelin expression. The determination of an effective dose is well within the capability of those skilled in the art.

For any compound, the therapeutically effective dose can be estimated initially either in cell culture assays, e.g., neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors that ameliorate the symptoms or condition. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are preferred. The data obtained from cell culture assays and animal studies are used in formulating a range of dosage for human use. The dosage of such compounds lies preferably within a range of circulating concentrations what include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors that may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for polynucleotides than for proteins or their inhibitors. Similarly, delivery of polynucleotides or polypeptides will be specific to particular cells, conditions, locations, etc. Preferred specific activities for a radiolabeled antibody may range from 0.1 to 10 mCi/mg of protein (Riva et al., Clin. Cancer Res. 5:3275s-3280s, 1999; Wong et al., Clin. Cancer Res. 6:3855-3863, 2000; Wagner et al., J. Nuclear Med. 43:267-272, 2002).

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

All examples were carried out using standard techniques, which are well known and routine to those of skill in the art, except where otherwise described in detail. Routine molecular biology techniques of the following examples can be carried out as described in standard laboratory manuals, such as Sambrook et al., Molecular Cloning: A Laboratory Manual, 2nd Ed.; Cold Spring Harbor Laboratory Press, Cold Spring Harbor, N.Y., 1989.

EXAMPLES

Example 1

Antibody Generation from HuCAL Libraries

For the generation of therapeutic antibodies against mesothelin, selections with the MorphoSys HuCAL GOLD phage display library were carried out. HuCAL GOLD® is a Fab library based on the HuCAL® concept (Knappik, A., et al., J. Mol. Biol. (2000) 296(1): 57; Krebs, B., et al., J. Immunol. Methods. (2001) 254(1-2): 67), in which all six CDRs are diversified, and which employs the CysDisplay™ technology for linking Fab fragments to the phage surface (Löhning, 2001; WO 01/05950).

A. Phagemid Rescue, Phage Amplification and Purification

HuCAL GOLD® phagemid library was amplified in 2×TY medium containing 34 µg/ml chloramphenicol and 1% glucose (2×TY-CG). After helper phage infection (VCSM13) at an OD600 of 0.5 (30 min at 37° C. without shaking; 30 min at 37° C. shaking at 250 rpm), cells were spun down (4120 g; 5 min; 4° C.), resuspended in 2×TY/34 µg/ml chloramphenicol/50 µg/ml kanamycin and grown overnight at 22° C. Phages were PEG-precipitated from the supernatant, resuspended in PBS/20% glycerol and stored at −80° C. Phage amplification between two panning rounds was conducted as follows: mid-log phase TG1 cells were infected with eluted phages and plated onto LB-agar supplemented with 1% of glucose and 34 µg/ml of chloramphenicol (LB-CG). After overnight incubation at 30° C., colonies were scraped off, adjusted to an OD600 of 0.5 and helper phage added as described above.

B. Pannings with HuCAL GOLD®

For the selections HuCAL GOLD® antibody-phages were divided into three pools corresponding to different VH master genes (pool 1: VH1/5λκ, pool 2: VH3 λκ, pool 3: VH2/4/6 λκ). These pools were individually pre-absorbed on mesothelin-negative CHO-K1 cells for depletion of irrelevant antibody phages and subsequently subjected to 3 rounds of alternating whole cell panning on mesothelin-expressing CHO- A9 and NCI-H226 cells followed by pH-elution. Finally, the remaining antibody phages were used to infect E. coli TG1 cells. After centrifugation the bacterial pellet was resuspended in 2×TY medium, plated on agar plates and incubated overnight at 30° C. The selected clones were then scraped from the plates, phages were rescued and amplified. The second and the third round of selections were performed as the initial one.

The Fab encoding inserts of the selected HuCAL GOLD® phages were subcloned into the expression vector pMORPH®x9_Fab_FS (Rauchenberger, R., et al., J. Biol. Chem. (2003) 278(40): 38194) to facilitate rapid expression of soluble Fab. The DNA of the selected clones was digested with XbaI and EcoRI thereby cutting out the Fab encoding insert (ompA-VLCL and phoA-Fd), and cloned into the XbaI/EcoRI cut vector pMORPH®x9_Fab_FS. Fab expressed in this vector carry two C-terminal tags (FLAG™ and Strep-tag® II) for detection and purification.

C. Affinity Maturation Affinity Maturation of Selected Fab by Stepwise Exchange of CDR Cassettes To increase affinity and biological activity of selected antibody fragments (MF-L, MF-A, MF-J, MF-T and MF-226), L-CDR3 and H-CDR2 regions were optimized in parallel by cassette mutagenesis using trinucleotide directed mutagenesis (Virnekäs et al, Nucleic Acids Res. 22(25): 5600-7), while the framework regions were kept constant (WO2006122797). Pannings for selection of high affinity phage displayed Fab fragments were performed either on purified biotinylated recombinant mesothelin (human or murine mesothelin) or directly on mesothelin expressing cell lines (NCI-H226 or OVCAR-3). Combinations of these different panning strategies were also applied throughout the three panning rounds which were performed.

Example 2

Epitope Grouping

Epitope grouping experiments were performed using Biacore by monitoring simultaneous binding of pairs of anti-mesothelin antibodies to immobilized mesothelin. Briefly, the first antibody was covalently immobilized to the sensor chip through primary amine coupling using n-hydroxysuccinamide (NHC) and N-ethyl-N'-dimethylaminopropyl carbodiimide (EDC). Unoccupied binding sites on the surface were then blocked with ethanolamine. Soluble mesothelin was captured on the surface via the immobilized antibody, therefore, the epitope of the capture antibody is blocked for all bound mesothelin molecules. A second antibody was immediately passed over the surface to bind to the immobilized mesothelin. Two antibodies recognizing the same or overlapping epitopes cannot bind to the mesothelin, whereas antibodies with distinct epitopes are able to bind. The antibody surface was regenerated with glycine, pH 2.8, to remove bound proteins and then the process was repeated with other antibodies. All combinations of seven antibodies were tested. Representative results using MF-T and several other antibodies are shown in FIG. 1A. Use of MF-T as the second antibody served as a positive control and anti-FLAG served as a negative control. FIG. 1B depicts a summary of the pairwise binding results for seven anti-mesothelin antibodies in a Venn diagram with circles representing individual epitopes. Overlapping circles represent overlapping epitopes. MF428 competed for binding with all other antibodies tested. MF-J and MF-T bind to distinct epitopes compared to each other and to MF-A, MF-226 and MF-L, which seem to compete for the same epitope region. The commercially available mouse antibody K1 binds to an epitope region distinct from the one recognized by MF-J and MF-T, but seems to share a similar epitope region to MF-A, MF-L and MF-226.

Example 3

Cross-Reactivity to Murine Mesothelin

Shown in Table 5 are results of Biacore and ELISA studies showing cross-reactivity of antibodies of the invention to murine mesothelin. The kinetic constants $k_{on}$ and $k_{off}$ were determined with serial dilutions of the respective purified Fab fragment binding to covalently immobilized human or murine mesothelin using the Biacore 3000 instrument (Biacore, Uppsala, Sweden). Covalent antigen immobilization was achieved by a standard EDC-NHS coupling procedure. Kinetic measurements were done in PBS, pH 7.2 at a flow rate of 20 μl/min using Fab concentration ranging from 1.5-500 nM. Injection time for each concentration was 1 min, followed by 3 min dissociation phase. For regeneration 5 μl 10 mM glycine buffer, pH 1.8 was used. All sensograms were fitted using the BIA evaluation software 3.1 (Biacore).

TABLE 5

Monovalent anti-mesothelin antibody affinities to human and murine mesothelin (Fab formats)

| | Human mesothelin | | Murine mesothelin | |
|---|---|---|---|---|
| Antibody (Fab) | $K_D$ [M] | kd [1/s] | $K_D$ [M] | kd [1/s] |
| MF-226 | $5.8 \times 10^{-8}$ | $3.8 \times 10^{-2}$ | $1.28 \times 10^{-6}$ | $1.4 \times 10^{-1}$ |
| MOR 06626 | $6.7 \times 10^{-10}$ | $1.2 \times 10^{-3}$ | $6.7 \times 10^{-9}$ | $9.8 \times 10^{-3}$ |
| MOR 06638 | $1.6 \times 10^{-8}$ | $6.3 \times 10^{-3}$ | $3.2 \times 10^{-7}$ | $4.0 \times 10^{-2}$ |
| MF-A | $1.9 \times 10^{-8}$ | $7.9 \times 10^{-2}$ | $6.7 \times 10^{-7}$ | $2.7 \times 10^{-1}$ |
| MOR 06657 | $9.5 \times 10^{-10}$ | $5.5 \times 10^{-3}$ | $3.6 \times 10^{-7}$ | $1.6 \times 10^{-1}$ |

Example 4

Invariant Binding to Mesothelin on Different Cancer Cell Lines

Figure 2:
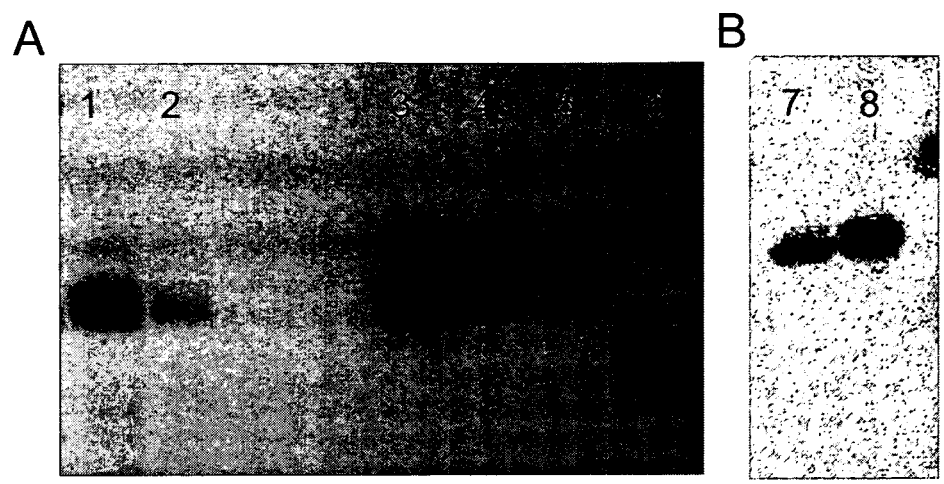
FIG. 2 shows different forms of mesothelin recognized by antibodies of the invention. 1. and 2: MF-J binding to mesothelin in OVCAR-3 cell extracts; 3. and 4: MF-J binding to mesothelin in CHO-A9 cell extracts; 5. MF-J binding to mesothelin in NCI-H226 cell extracts; 6. MF-J binding to recombinant, deglycosylated mesothelin; 7. MOR06635 binding to OVCAR-3 cell extracts; and 8. MOR06635 binding to NCI-H226 cell extracts.

FIG. 2 depicts immunoblots of mesothelin-expressing cell lines generated with anti-mesothelin antibody MF-J (A) and MOR 06635 (B). Briefly, cell extracts were generated by a standard lysis protocol by sonicating the cells for 3 min in the presence of DNAse and RNAse. Cell proteins were separated by SDS-PAGE under denaturing and reducing conditions, blotted onto nitrocellulose membranes and incubated with the appropriate primary antibody (MF-J-IgG or MOR 06635-Fab). Anti-human IgG peroxidase-coupled secondary antibody was used for detection, which was performed with ECL substrate. While only one band appeared when extracts of OVCAR-3 cells were blotted with mesothelin antibodies, multiple bands were observed in CHO-A9 and NCI-H226 cells. This indicates the presence of different isoforms of mesothelin in OVCAR-3, CHO-A9 and NCI-H226 cell lines. Since OVCAR-3 and CHO-A9 express the same, fully spliced transcript variant (Muminova, Z. E., et al., BMC Cancer (2004) 4:19), and SEQ ID 371, the multiple bands must be caused by translational or posttranslational modifications, which might consist in, but are not limited to, for example, differences in glycosylation patterns.

Table 6 shows that $EC_{50}$ values obtained by FACS titration of representative affinity matured antibodies of the invention on NCI-H226 and OVCAR-3 cells do not vary significantly for a subset of IgGs (i.e. MOR07265, -6631, -6669, -7111, -6640, -6642) while other IgGs show a more than eight fold higher $EC_{50}$ value on OVCAR-3 than NCI-H226 (i.e. MOR06626, -6638, -6657. -6643). Most notably IgGs MOR07265, -6631, -6635, -6669, -7111, -6640, -6642 are affinity matured derivatives of parental IgG MF-J, indicating that these IgGs bind to a related epitope which is invariably present on OVCAR-3 as well as NCI-H226 cells. Thus these data demonstrate the quality of invariant binding provided in the present invention.

FACS titration was performed in a 96 well microtiter plate, in which serial dilutions of the primary antibody in a volume of 80 μl of FACS buffer (3% FCS, 0.02% $NaN_3$ in PBS) were mixed with 20 μl of a cell suspension consisting of $10^6$ cells/ml which had been detached with accutase or trypsin/EDTA, and resuspended in FACS buffer. Incubation was performed at 4° C. for 1 hour with agitation. Cells were washed twice with FACS buffer and resuspended in 100 μl/well of anti-human PE conjugate solution in FACS buffer. Incubation and washing was performed as before. Analysis of cell-bound antibodies was done using the FACS Array device. $EC_{50}$ values were determined from fluorescence medians of duplicates using Prism 4.0 software (GraphPad) applying non-linear regression fit.

TABLE 6

FACS titration of IgG antibodies on NCI-H226 and OVCAR-3 cells

| Antibody (IgG) | $EC_{50}$ [nM] | | x-fold different $EC_{50}$ on |
|---|---|---|---|
| | NCI-H226 | OVCAR-3 | OVCAR-3 vs. NCI-H226 |
| MOR06626 | 0.44 | 9.68 | 22.0 |
| MOR06638 | 0.19 | 4.19 | 22.1 |
| MOR07265 | 1.11 | 1.06 | 1.0 |
| MOR06631 | 2.02 | 0.96 | 0.5 |
| MOR06669 | 0.41 | 1.40 | 3.4 |
| MOR07111 | 0.80 | 1.35 | 1.7 |
| MOR06640 | 0.63 | 0.53 | 0.8 |
| MOR06642 | 0.58 | 0.54 | 0.9 |
| MOR06657 | 0.14 | 0.53 | 14 |
| MOR06643 | 0.23 | 1.86 | 8.1 |

Example 5

Binding to Mesothelin in the Presence of Cancer Antigen 125 (CA125)

Figure 3:
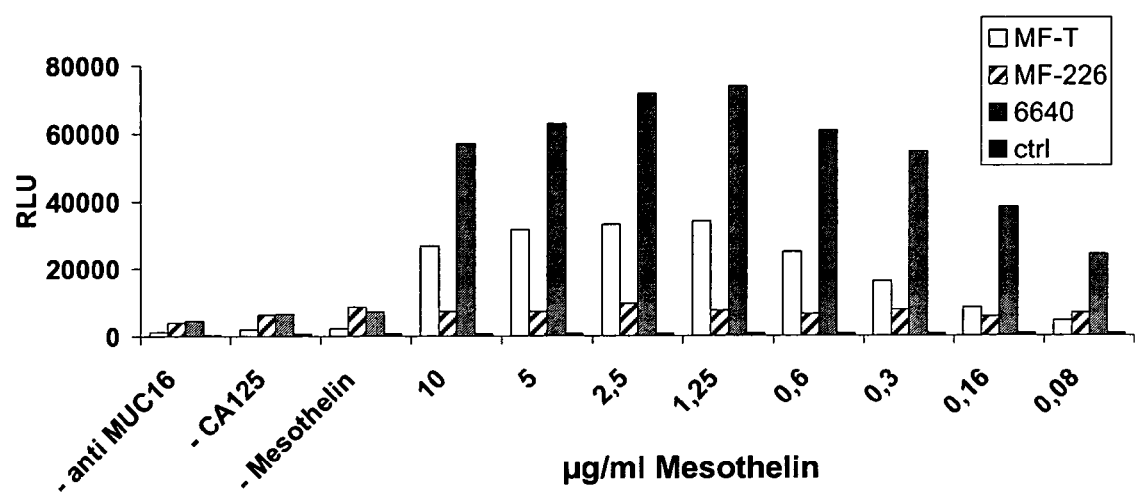
FIG. 3 shows that cancer antigen 125 (CA125) binds mesothelin when it is bound to a subset of mesothelin antibodies including MOR06640 and MF-T, while other antibodies, such as MF-226, compete with CA125 for mesothelin binding. Data shown are relative light units (RLU) detected by SECTOR Light Imager (Meso Scale Discovery). Plates were coated with the mesothelin antibody depicted. Mesothelin was added at the concentrations indicated and titrated down. CA125 was bound subsequently at a constant concentration. Detection was performed with a mouse anti-CA125 antibody and an MSD Sulfo tag labelled anti mouse FAB antibody.

FIG. 3 shows that cancer antigen 125 (CA125) binds to mesothelin which is in turn bound to a subset of mesothelin antibodies including MOR06640 and MF-T, while other antibodies, such as MF-226, compete with CA125 for mesothelin binding. Data shown are relative light units (RLU) detected by SECTOR Light Imager (Meso Scale Discovery). Plates were coated with the mesothelin antibody depicted at 15 μg/ml, and washed and blocked after each subsequent incubation. Mesothelin was added at the concentrations indicated and titrated down from 10 μg/ml to 0.08 μg/ml. Plates were subsequently incubated with CA125 (Lee Biosolutions, Cat #150-11, 50 000 U/ml diluted 1:300). Detection was performed with a mouse anti-CA125 antibody and an MSD Sulfo tag (Meso Scale Discovery) labelled anti mouse Fab antibody. An unspecific human control antibody was coated as a control. Further controls included the full assay setup with mesothelin at the highest concentrations tested (10 μg/ml) and omission of either CA125 or the mouse anti-CA125 antibody, or full assay setup without mesothelin. This example shows that antibodies, antigen-binding antibody fragments, or variants thereof, which invariantly bind mesothelin can be identified by in vitro testing.

Example 6

Internalization

Figure 4:
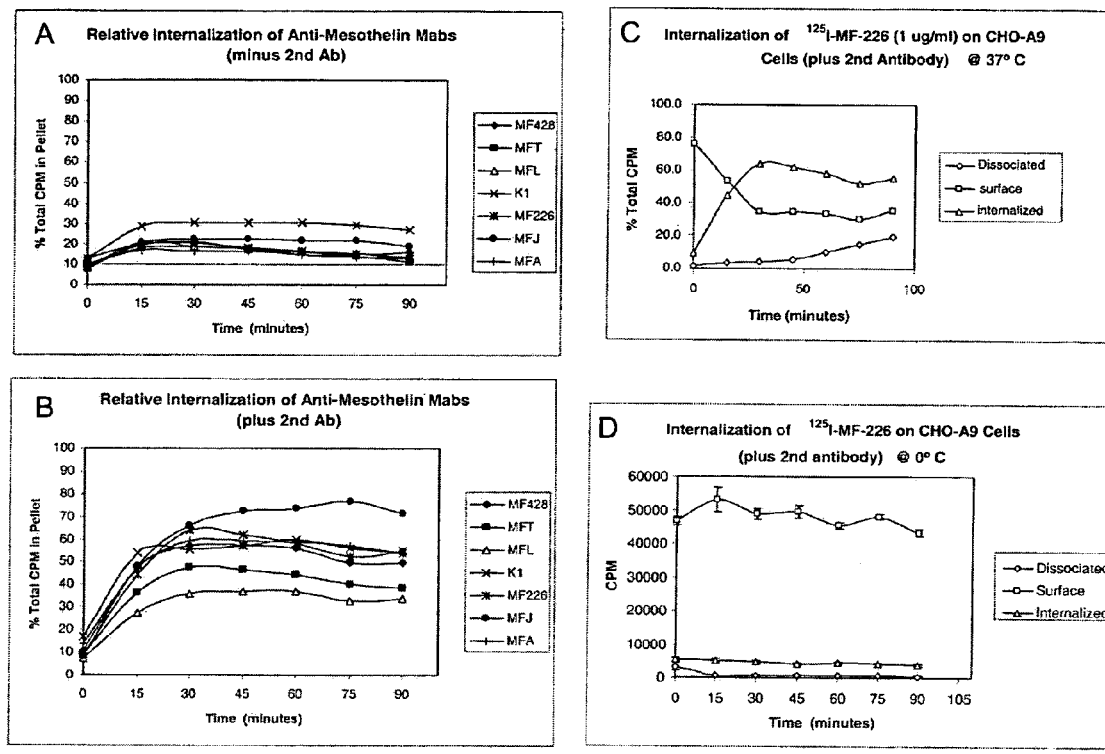
FIG. 4 provides data on internalization of 125I-anti-mesothelin antibodies on CHO-A9 cells expressing mesothelin. Relative internalization of seven anti-mesothelin mabs, including the commercial positive control K1, in the absence (A), and in the presence (B) of the stabilizing second antibody. Representative data using MF-226 plus second antibody, showing relative amounts of dissociated, surface-bound and internalized antibody at 37° C. over time (C) is compared with that at the non-permissive temperature of 0° C. (D).

Relative internalization of anti-mesothelin antibodies on CHO-A9 cells is shown in FIG. 4. Briefly, CHO-A9 cells expressing mesothelin protein were labeled with $^{125}$I-anti-mesothelin antibodies for 2 hours at 0° C., to bind the labeled antibody to cell surface mesothelin. The low temperature inhibited internalization. Unbound antibody was washed away using cold buffer and individual aliquots of labeled cells were placed in a 37° C. water bath to initiate internalization. A time course was run in which triplicate samples were collected at: 0, 15, 30, 45, 60, 75 and 90 minutes. At each time point, samples were centrifuged to pellet cells and the supernatant was collected, which contained antibody that had dissociated from the cells. The cell pellet was then briefly washed with acid (PBS+1% glucose pH1.0) in order to remove cell surface-bound labeled antibody, and then pelleted by centrifugation. The supernatant, containing antibody eluted from the cell surface was collected. The pellet fraction, containing internalized antibody, was collected separately. After completion of the time course, the radioactivity in each of the fractions from all time points was determined using a gamma counter. The percentage of total counts present in the fractions represents the percentage of the antibody that was dissociated, bound to the cell surface or internalized at each time point. In experiments in which a second antibody (goat anti-human IgG Fc, or goat anti-mouse IgG Fc, respectively) was added along with the primary labeled antibody to crosslink and thus stabilize the cell surface-bound antibody, much lower antibody dissociation rates were observed compared to cells only treated with the primary antibody. Correspondingly higher internalization levels were also achieved for all antibodies tested with the second antibody. In the absence of a second antibody, the relatively rapid off-rates of the antibodies, as seen in the Biacore studies, reduced the antibodies' residency time on the cell surface such that internalization was significantly reduced. Therefore, four candidate antibodies were chosen for affinity maturation to obtain progenitor antibodies with reduced dissociation rates.

TABLE 7

Sequences of the antibodies

| Antibody | HCDR1 SEQ ID | HCDR2 SEQ ID | HCDR3 SEQ ID | LCDR1 SEQ ID | LCDR2 SEQ ID | LCDR3 SEQ ID | VH Protein SEQ ID | VL Protein SEQ ID | VH Nucleotide SEQ ID | VL Nucleotide SEQ ID |
|---|---|---|---|---|---|---|---|---|---|---|
| MF-J | 1 | 31 | 67 | 99 | 129 | 160 | 198 | 241 | 284 | 327 |
| MOR 07265 | 1 | 32 | 67 | 99 | 129 | 161 | 199 | 242 | 285 | 328 |

TABLE 7-continued

Sequences of the antibodies

| Antibody | HCDR1 SEQ ID | HCDR2 SEQ ID | HCDR3 SEQ ID | LCDR1 SEQ ID | LCDR2 SEQ ID | LCDR3 SEQ ID | VH Protein SEQ ID | VL Protein SEQ ID | VH Nucleotide SEQ ID | VL Nucleotide SEQ ID |
|---|---|---|---|---|---|---|---|---|---|---|
| MOR 06631 | 1 | 32 | 67 | 99 | 129 | 160 | 200 | 243 | 286 | 329 |
| MOR 06669 | 1 | 33 | 67 | 99 | 129 | 160 | 201 | 244 | 287 | 330 |
| MOR 07111 | 1 | 31 | 67 | 99 | 129 | 162 | 202 | 245 | 288 | 331 |
| MOR 06640 | 1 | 31 | 67 | 99 | 129 | 161 | 203 | 246 | 289 | 332 |
| MOR 06642 | 1 | 31 | 67 | 99 | 129 | 163 | 204 | 247 | 290 | 333 |
| MOR 06643 | 2 | 34 | 68 | 100 | 130 | 164 | 205 | 248 | 291 | 334 |
| MF-226 | 3 | 35 | 69 | 101 | 131 | 165 | 206 | 249 | 292 | 335 |
| MOR 06626 | 3 | 36 | 69 | 101 | 131 | 165 | 207 | 250 | 293 | 336 |
| MOR 06635 | 1 | 37 | 67 | 99 | 129 | 160 | 208 | 251 | 294 | 337 |
| MOR 06638 | 3 | 35 | 69 | 101 | 131 | 166 | 209 | 252 | 295 | 338 |
| MF-A | 4 | 38 | 70 | 102 | 132 | 167 | 210 | 253 | 296 | 339 |
| MOR 06657 | 4 | 38 | 70 | 102 | 132 | 168 | 211 | 254 | 297 | 340 |
| MF-T | 5 | 39 | 71 | 103 | 133 | 169 | 212 | 255 | 298 | 341 |
| MF-L | 2 | 34 | 68 | 100 | 130 | 170 | 213 | 256 | 299 | 342 |
| MF-1 | 6 | 40 | 72 | 104 | 134 | 171 | 214 | 257 | 300 | 343 |
| MF-5 | 7 | 41 | 73 | 105 | 135 | 172 | 215 | 258 | 301 | 344 |
| MF-8 | 8 | 42 | 74 | 106 | 136 | 173 | 216 | 259 | 302 | 345 |
| MF-24 | 9 | 43 | 75 | 107 | 137 | 174 | 217 | 260 | 303 | 346 |
| MF-25 | 10 | 44 | 76 | 108 | 138 | 175 | 218 | 261 | 304 | 347 |
| MF-27 | 1 | 45 | 77 | 109 | 139 | 176 | 219 | 262 | 305 | 348 |
| MF-73 | 11 | 46 | 78 | 110 | 140 | 177 | 220 | 263 | 306 | 349 |
| MF-78 | 12 | 47 | 79 | 111 | 141 | 178 | 221 | 264 | 307 | 350 |
| MF-84 | 13 | 48 | 80 | 112 | 142 | 179 | 222 | 265 | 308 | 351 |
| MF-101 | 14 | 49 | 81 | 113 | 143 | 180 | 223 | 266 | 309 | 352 |
| MF-230 | 15 | 50 | 82 | 114 | 144 | 181 | 224 | 267 | 310 | 353 |
| MF-236 | 16 | 51 | 83 | 115 | 145 | 182 | 225 | 268 | 311 | 354 |
| MF-252 | 17 | 52 | 84 | 116 | 146 | 183 | 226 | 269 | 312 | 355 |
| MF-275 | 17 | 53 | 85 | 117 | 147 | 184 | 227 | 270 | 313 | 356 |
| MF-423 | 18 | 54 | 86 | 118 | 148 | 185 | 228 | 271 | 314 | 357 |
| MF-427 | 19 | 55 | 87 | 119 | 149 | 186 | 229 | 272 | 315 | 358 |
| MF-428 | 20 | 56 | 88 | 120 | 150 | 187 | 230 | 273 | 316 | 359 |
| MF-C | 21 | 57 | 89 | 121 | 151 | 188 | 231 | 274 | 317 | 360 |
| MF-I | 22 | 58 | 90 | 102 | 152 | 189 | 232 | 275 | 318 | 361 |
| MF-M | 23 | 59 | 91 | 122 | 153 | 190 | 233 | 276 | 319 | 362 |
| MF-P | 24 | 60 | 92 | 123 | 154 | 191 | 234 | 277 | 320 | 363 |
| MF-Q | 25 | 61 | 93 | 124 | 155 | 192 | 235 | 278 | 321 | 364 |
| MF-S | 26 | 62 | 94 | 125 | 156 | 193 | 236 | 279 | 322 | 365 |
| MF-U | 27 | 63 | 95 | 126 | 157 | 194 | 237 | 280 | 323 | 366 |
| MF-V | 28 | 64 | 96 | 127 | 158 | 195 | 238 | 281 | 324 | 367 |
| MF-W | 29 | 65 | 97 | 102 | 159 | 196 | 239 | 282 | 325 | 368 |
| MF-Y | 30 | 66 | 98 | 128 | 155 | 197 | 240 | 283 | 326 | 369 |

The invention claimed is:

1. An isolated human antibody or functional fragment thereof comprising an antigen-binding site that is specific for Mesothelin (SEQ ID NO:370), wherein said antibody or functional fragment thereof exhibits invariant binding of Mesothelin, and wherein the antigen-binding site comprises complementary determining regions SEQ ID NOS. 5, 39, 71, 103, 133, and 169.

2. An isolated antibody or functional fragment thereof to according to claim 1, which is an IgG.

3. An isolated antibody or functional fragment thereof according to claim 1, which is a Fab or scFv antibody fragment.

4. A pharmaceutical composition comprising an antibody or functional fragment thereof according to claim 1, and a pharmaceutically acceptable carrier or excipient therefore.

5. A human antibody or functional fragment thereof according to claim 1, wherein the human antibody is a synthetic human antibody.

* * * * *